(12) United States Patent
Arslan

(10) Patent No.: US 10,723,789 B2
(45) Date of Patent: *Jul. 28, 2020

(54) IMMUNOGLOBULIN-LIKE MOLECULES DIRECTED AGAINST FIBRONECTIN-EDA

(71) Applicant: UMC UTRECHT HOLDING B.V., Utrecht (NL)

(72) Inventor: Fatih Arslan, Utrecht (NL)

(73) Assignee: UMC UTRECHT HOLDING B.V., Utrecht (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/003,160

(22) Filed: Jun. 8, 2018

(65) Prior Publication Data
US 2018/0346557 A1 Dec. 6, 2018

Related U.S. Application Data

(62) Division of application No. 15/103,677, filed as application No. PCT/NL2014/050859 on Dec. 12, 2014, now Pat. No. 10,011,652.

(30) Foreign Application Priority Data

Dec. 12, 2013 (NL) ..................................... 2011943
Dec. 12, 2013 (NL) ..................................... 2011944

(51) Int. Cl.
*A61K 39/395* (2006.01)
*A61K 39/00* (2006.01)
*C07K 16/18* (2006.01)

(52) U.S. Cl.
CPC ........ *C07K 16/18* (2013.01); *A61K 2039/505* (2013.01); *A61K 2039/54* (2013.01); *A61K 2039/545* (2013.01); *C07K 2317/20* (2013.01); *C07K 2317/24* (2013.01); *C07K 2317/34* (2013.01)

(58) Field of Classification Search
None
See application file for complete search history.

(56) References Cited

U.S. PATENT DOCUMENTS

| | | | |
|---|---|---|---|
| 4,980,279 A | 12/1990 | Peters et al. | |
| 5,108,898 A | 4/1992 | Peters et al. | |
| 5,420,012 A | 5/1995 | Partanen et al. | |
| 5,530,101 A | 6/1996 | Queen et al. | |
| 5,571,679 A | 11/1996 | Sekiguchi et al. | |
| 5,585,089 A | 12/1996 | Queen et al. | |
| 5,639,641 A | 6/1997 | Pedersen et al. | |
| 5,693,762 A | 12/1997 | Queen et al. | |
| 5,843,708 A | 12/1998 | Hardman et al. | |
| 6,180,370 B1 | 1/2001 | Queen et al. | |
| 2009/0170751 A1 | 7/2009 | Hoeoek et al. | |
| 2013/0040361 A1* | 2/2013 | Rybak ................ | A61K 51/1093 435/188 |
| 2013/0171672 A1 | 7/2013 | Hussa et al. | |

FOREIGN PATENT DOCUMENTS

| | | |
|---|---|---|
| EP | 0603735 A2 | 6/1994 |
| KR | 1020100016094 A | 2/2010 |
| WO | 2006/037604 A1 | 4/2006 |
| WO | 2006/128690 A1 | 12/2006 |
| WO | 2008/120101 A2 | 10/2008 |
| WO | 2009/013619 A2 | 1/2009 |
| WO | 2012/057613 A1 | 5/2012 |
| WO | 2012/061637 A2 | 5/2012 |
| WO | 2015/088348 A1 | 6/2015 |
| WO | 2016/093700 A3 | 12/2016 |

OTHER PUBLICATIONS

ABCAM product datasheet for Anti-Fibronectin antibody[IST-9] (ab6328), Oct. 8, 2014, phage 1.
Arslan, F., et al. "Lack of the endogenous ligand for Toll-like receptor 2/4, fibronectin extra domain A, prevents adverse cardiac remodeling and preserves cardiac function after acute MI in mice.", Abstract presented at a conference from the Dutch Atherosclerosis Society, dated Mar. 12-13, 2009.
Arslan, F., et al. "Lack of the endogenous ligand for Toll-like receptor 2/4, fibronectin extra domain A, prevents adverse cardiac remodeling and preserves cardiac function after acute MI in mice.", Abstract presented at NVCC conference, dated Apr. 2-3, 2009.
Arslan, Fatih, et al. "Lack of Fibronectin EDA Prevents Adverse Cardiac Remodeling and Preserves Cardiac Function After Acute MI.", Abstract presented at NVCC conference dated Oct. 15-17, 2009.
Arslan, F., et al. "Lack of the endogenous ligand for Toll-like receptor 2/4, fibronectin extra domain A, prevents adverse cardiac remodeling and preserves cardiac function after acute MI in mice." European Heart Journal. vol. 30. Great Clarendon St, Oxford OX2 6DP, England: Oxford Univ Press, 2009.
Arslan, Fatih, et al. "Lack of Fibronectin EDA Prevents Adverse Cardiac Remodeling and Preserves Cardiac Function After Acute MI." (2009): S818-S819.
Arslan, Fatih, et al. "Lack of fibronectin-EDA promotes survival and prevents adverse remodeling and heart function deterioration after myocardial infarction." Circulation research (2011): CIRCRESAHA-110.
Astrof, Sophie, and Richard O. Hynes. "Fibronectins in vascular morphogenesis." Angiogenesis 12.2 (2009): 165-175.

(Continued)

*Primary Examiner* — Maher M Haddad
(74) *Attorney, Agent, or Firm* — Tarolli, Sundheim, Covell & Tummino LLP

(57) ABSTRACT

The present invention is concerned with immunoglobulin (Ig)-like molecules or fragments thereof for use in treatment, prevention, or prevention of progression of adverse cardiac remodelling and conditions resulting from or relating to myocardial infarction and pressure-overload, such as heart failure, aneurysm formation and remote myocardial fibrosis and for use in improving angiogenesis, preferably after ischemic injury. The invention also provides nucleic acid molecules encoding said Ig-like molecules, vectors comprising same, and host cells comprising same.

13 Claims, 23 Drawing Sheets

Specification includes a Sequence Listing.

(56) References Cited

OTHER PUBLICATIONS

Borsi, Laura, et al. "Preparation of phage antibodies to the ED-A domain of human fibronectin." Experimental cell research 240.2 (1998): 244-251.

Brown, McKay, et al. "Tolerance of single, but not multiple, amino acid replacements in antibody VH CDR 2: a means of minimizing B cell wastage from somatic hypermutation?." The Journal of Immunology 156.9 (1996): 3285-3291.

Chauhan, Anil K., et al. "Prothrombotic effects of fibronectin isoforms containing the EDA domain." Arteriosclerosis, thrombosis, and vascular biology 28.2 (2008): 296-301.

Franz, M., et al. "Analysis of ED-A+ fibronectin expression after heterotopic rat heart transplantation: association to cardiac allograft rejection and implications for targeted post-transplant therapy." The Thoracic and Cardiovascular Surgeon 58.S 01 (2010): P138.

Franz, Marcus, et al. "Changes in extra cellular matrix remodelling and re-expression of fibronectin and tenascin-C splicing variants in human myocardial tissue of the right atrial auricle: implications for a targeted therapy of cardiovascular diseases using human SIP format antibodies." Journal of molecular histology 41.1 (2010): 39-50.

Franz, Marcus, et al. "Extra cellular matrix remodelling after heterotopic rat heart transplantation: gene expression profiling and involvement of ED-A+ fibronectin, alpha-smooth muscle actin and B+ tenascin-C in chronic cardiac allograft rejection." Histochemistry and cell biology 134.5 (2010): 503-517.

Katsargyris, Athanasios, et al. "Toll-like receptor modulation: a novel therapeutic strategy in cardiovascular disease?." Expert opinion on therapeutic targets 12.11 (2008): 1329-1346.

Konstandin, Mathias H., et al. "Fibronectin contributes to pathological cardiac hypertrophy but not physiological growth." Basic research in cardiology 108.5 (2013): 375.

Liao, Yung-Feng, et al. "Identification of two amino acids within the EIIIA (ED-A) segment of fibronectin constituting the epitope for two function-blocking monoclonal antibodies." Journal of Biological Chemistry 274.25 (1999): 17876-17884.

Okamura, Yoshinori, et al. "The extra domain A of fibronectin activates Toll-like receptor 4." Journal of Biological Chemistry 276.13 (2001): 10229-10233.

Owens, Raymond J., and Robert J. Young. "The genetic engineering of monoclonal antibodies." Journal of immunological methods 168.2 (1994): 149-165.

Oyama, Fumitaka, et al. "Oncodevelopmental regulation of the alternative splicing of fibronectin pre-messenger RNA in human lung tissues." Cancer research 50.4 (1990): 1075-1078.

Peters, John H., et al. "Human endothelial cells synthesize, process, and secrete fibronectin molecules bearing an alternatively spliced type III homology (ED1)." Blood 75.9 (1990): 1801-1808.

Peters, John H., et al. "Release of Soluble Fibronectin Containing an Extra Type III Domain (ED1) during Acute Pulmonary Injury Mediated by Oxidants or Leukocytes in ViV01-4." Am Rev Respir Dis 138 (1988): 167-174.

Riad, Alexander, et al. "Toll-like receptor-4 modulates survival by induction of left ventricular remodeling after myocardial infarction in mice." The Journal of Immunology 180.10 (2008): 6954-6961.

Rybak, Jascha-N., et al. "The extra-domain A of fibronectin is a vascular marker of solid tumors and metastases." Cancer research 67.22 (2007): 10948-10957.

Shimamoto, Akira, et al. "Inhibition of Toll-like receptor 4 with eritoran attenuates myocardial ischemia-reperfusion injury." Circulation 114.1 suppl (2006): 1-270.

Timmers, Leo, et al. "Toll-like receptor 4 mediates maladaptive left ventricular remodeling and impairs cardiac function after myocardial infarction." Circulation research 102.2 (2008): 257-264.

Vartio, T., et al. "Differential expression of the ED sequence-containing form of cellular fibronectin in embryonic and adult human tissues." Journal of cell science 88.4 (1987): 419-430.

Villa, Alessandra, et al. "A high-affinity human monoclonal antibody specific to the alternatively spliced EDA domain of fibronectin efficiently targets tumor neo-vasculature in vivo." International journal of cancer 122.11 (2008): 2405-2413.

Zambrowicz, Brian P., and Arthur T. Sands. "Knockouts model the 100 best-selling drugs—will they model the next 100?." Nature reviews Drug discovery 2.1 (2003): 38.

U.S. Appl. No. 15/535,129, filed Jun. 12, 2017.

Rader, Christoph, David A. Cheresh, and Carlos F. Barbas. "A phage display approach for rapid antibody humanization: designed combinatorial V gene libraries." Proceedings of the National Academy of Sciences 95.15 (1998): 8910-8915.

Sambrook, Joseph, Edward F. Fritsch, and Tom Maniatis. Molecular cloning: a laboratory manual. No. Ed. 2. Cold spring harbor laboratory press, 1989.

Ausubel, F. M., et al. "Current protocols in molecular biology New York." NY: Wiley (1987).

The International Search Report in correspondence to the International Application No. PCT/NL2014/050859, dated May 6, 2015, 6 pages.

"Methods in Enzymology" Academic Press, San Diego.

Paul, William E. "Fundamental Immunology, Pub." 3rd Edition (1993): 292-293.

Colman, Peter M. "Effects of amino acid sequence changes on antibody-antigen interactions." Research in Immunology 145.1 (1994): 33-36.

Lefernan, Seth, et al. "A single amino acid substitution in a common African allele of the CD4 molecule ablates binding of the monoclonal antibody, OKT4." Molecular immunology 28.11 (1991): 1171-1181.

Li, Choh Hao, et al. "beta-Endorphin omission analogs: dissociation of immunoreactivity from other biological activities." Proceedings of the National Academy of Sciences 77.6 (1980): 3211-3214.

Abaza, Mohamed-Salah I., and M. Zouhair Atassi. "Effects of amino acid substitutions outside an antigenic site on protein binding to monoclonal antibodies of predetermined specificity obtained by peptide immunization: Demonstration with region 94-100 (antigenic site 3) of myoglobin." Journal of protein chemistry 11.5 (1992): 433-444.

Rudikoff, Stuart, et al. "Single amino acid substitution altering antigen-binding specificity." Proceedings of the National Academy of Sciences 79.6 (1982): 1979-1983.

Kussie, Paul H., et al. "A single engineered amino acid substitution changes antibody fine specificity." The Journal of Immunology 152.1 (1994): 146-152.

Chen, C. H. I. N. G., et al. "Enhancement and destruction of antibody function by somatic mutation: unequal occurrence is controlled by V gene combinatorial associations." The EMBO journal 14.12 (1995): 2784-2794.

Vassilev, Tchavdar L., et al. "Inhibition of cell adhesion by antibodies to Arg—Gly—Asp (RGD) in normal immunoglobulin for therapeutic use (intravenous immunoglobulin, IVIg)." Blood 93.11 (1999): 3624-3631.

Kaspar, Manuela, Luciano Zardi, and Dario Neri. "Fibronectin as target for tumor therapy." International journal of cancer 118.6 (2006): 1331-1339.

Shinde, Arti V., et al. "Identification of the peptide sequences within the EIIIA (EDA) segment of fibronectin that mediate integrin $\alpha 9\beta 1$-dependent cellular activities." Journal of Biological Chemistry 283.5 (2008): 2858-2870.

Chen, Ching, Victoria A. Roberts, and Marvin B. Rittenberg. "Generation and analysis of random point mutations in an antibody CDR2 sequence: many mutated antibodies lose their ability to bind antigen." Journal of Experimental Medicine 176.3 (1992): 855-866.

Ohno, Susumu, Nozomu Mori, and Takeshi Matsunaga. "Antigen-binding specificities of antibodies are primarily determined by seven residues of VH." Proceedings of the National Academy of Sciences 82.9 (1985): 2945-2949.

\* cited by examiner

Control

Anti-EDA

SEQUENCE LISTING

<160> NUMBER OF SEQ ID NOS: 63

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(5)

```
<223> OTHER INFORMATION: Any amino acid

<400> SEQUENCE: 1

Gly Ile Xaa Xaa Xaa Phe
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Ile His Glu Leu Phe
1               5

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Tyr Ser Ile Thr Ser Gly Tyr Ser Trp His
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Ile His Tyr Ser Gly Ile Ala Asn Tyr Asn Pro Ser Leu Lys Ser
1               5                   10                  15

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Lys Thr Gly Phe Phe Asp Tyr
1               5

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ser Ser Gln Ser Leu Val His Ser Asn Gly Asn Thr Tyr Leu His
1               5                   10                  15

<210> SEQ ID NO 7
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Val Ser Asn Arg Phe Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Gln Ser Ala His Val Pro Pro Thr
1               5

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Tyr Ser Ile Thr Ser Gly Tyr Ser Trp His
1               5                   10

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Ile His Tyr Ser Gly Ser Ala Asn Tyr Asn Pro Ser Leu Lys Ser
1               5                   10                  15

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Lys Thr Gly Phe Phe Asp Tyr
1               5

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12
```

-continued

```
Arg Ser Ser Gln Ser Leu Val His Ser Asn Gly Asn Thr Tyr Leu His
1               5                   10                  15
```

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

```
Lys Val Ser Asn Arg Phe Ser
1               5
```

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

```
Ser Gln Ser Ala His Val Pro Pro Thr
1               5
```

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Gly Tyr Ser Ile Ala Ser Gly Tyr Ser Trp His
1               5                   10
```

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Tyr Ile His Phe Ser Gly Ser Ala Asn Tyr Asn Pro Ser Leu Lys Ser
1               5                   10                  15
```

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Glu Ala Arg Gly Tyr Phe Asp Tyr
1               5
```

<210> SEQ ID NO 18
<211> LENGTH: 16
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 18

Arg Ser Ser Gln Ser Ile Val Arg Ser Asn Gly Asn Thr Tyr Leu Thr
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Val Ser Asn Arg Phe Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Phe Gln Gly Ser His Val Pro Pro Thr
1               5

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Thr or Ala

<400> SEQUENCE: 21

Gly Tyr Ser Ile Xaa Ser Gly Tyr Ser Trp His
1               5                   10

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Tyr or Phe
<220> FEATURE:
<221> NAME/KEY: MOD_RES
<222> LOCATION: (7)..(7)
<223> OTHER INFORMATION: Ser or Ile

<400> SEQUENCE: 22

Tyr Ile His Xaa Ser Gly Xaa Ala Asn Tyr Asn Pro Ser Leu Lys Ser
1               5                   10                  15

<210> SEQ ID NO 23
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys or Ala
<220> FEATURE:
<221> NAME/KEY: MOD_RES
<222> LOCATION: (3)..(3)
<223> OTHER INFORMATION: Thr or Arg
<220> FEATURE:
<221> NAME/KEY: MOD_RES
<222> LOCATION: (5)..(5)
<223> OTHER INFORMATION: Phe or Tyr

<400> SEQUENCE: 23

Glu Xaa Xaa Gly Xaa Phe Asp Tyr
1               5

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Leu or Ile
<220> FEATURE:
<221> NAME/KEY: MOD_RES
<222> LOCATION: (8)..(8)
<223> OTHER INFORMATION: His or Arg
<220> FEATURE:
<221> NAME/KEY: MOD_RES
<222> LOCATION: (16)..(16)
<223> OTHER INFORMATION: His or Thr

<400> SEQUENCE: 24

Arg Ser Ser Gln Ser Xaa Val Xaa Ser Asn Gly Asn Thr Tyr Leu Xaa
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Lys Val Ser Asn Arg Phe Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Phe
<220> FEATURE:
<221> NAME/KEY: MOD_RES
<222> LOCATION: (3)..(3)
<223> OTHER INFORMATION: Ser or Gly
```

```
<220> FEATURE:
<221> NAME/KEY: MOD_RES
<222> LOCATION: (4)..(4)
<223> OTHER INFORMATION: Ala or Ser

<400> SEQUENCE: 26

Xaa Gln Xaa Xaa His Val Pro Pro Thr
1               5

<210> SEQ ID NO 27
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Tyr Ser Ser Pro Glu Asp Gly Ile His Glu Leu Phe Pro Ala Pro
1               5                   10                  15

Asp Gly Glu Glu Asp Thr Ala Glu Leu Gln Gly Gly Cys
            20                  25

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Leu Phe Pro Ala Pro
1               5

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Phe Thr Phe Ser Asn Ser Ala Met Thr
1               5                   10

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Ile Ser Gly Gly Gly Thr Thr Tyr Tyr Pro Asp Ser Val Lys Gly
1               5                   10                  15

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31
```

```
Lys Ala Ser Gln Asn Val Val Thr Asn Val Ala
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Ala Ser Tyr Arg Tyr Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Gln Tyr Asn Ser Tyr Pro Tyr Thr
1               5

<210> SEQ ID NO 34
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln His Pro Gly Lys Lys Leu Glu Trp
        35                  40                  45

Met Gly Tyr Ile His Tyr Ser Gly Ile Ala Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Thr Glu Lys Thr Gly Phe Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190
```

```
Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
        210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 35
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Ala His Val Pro Pro Thr Phe Gly Gly Gly Thr Lys Val Glu Ile Lys
            100                 105                 110
```

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 36
<211> LENGTH: 438
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Ala Met Thr Trp Val Arg Gln Ala Pro Gly Lys Arg Leu Glu Trp Val
        35                  40                  45

Ala Ser Ile Ser Gly Gly Gly Thr Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Ser His Tyr Trp Gly Gln Gly Thr Leu Val Thr Val Ser Ser Ala
            100                 105                 110

Ser Thr Lys Gly Pro Ser Val Phe Pro Leu Ala Pro Cys Ser Arg Ser
            115                 120                 125

Thr Ser Glu Ser Thr Ala Ala Leu Gly Cys Leu Val Lys Asp Tyr Phe
            130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
            165                 170                 175

Ser Ser Val Val Thr Val Pro Ser Ser Ser Leu Gly Thr Lys Thr Tyr
            180                 185                 190

Thr Cys Asn Val Asp His Lys Pro Ser Asn Thr Lys Val Asp Lys Arg
            195                 200                 205

Val Glu Ser Lys Tyr Gly Pro Pro Cys Pro Pro Cys Pro Ala Pro Glu
            210                 215                 220

Ala Ala Gly Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp

```
                        245                 250                 255
Val Ser Gln Glu Asp Pro Glu Val Gln Phe Asn Trp Tyr Val Asp Gly
                260                 265                 270

Val Glu Val His Asn Ala Lys Thr Lys Pro Arg Glu Glu Gln Phe Asn
            275                 280                 285

Ser Thr Tyr Arg Val Val Ser Val Leu Thr Val Leu His Gln Asp Trp
        290                 295                 300

Leu Asn Gly Lys Glu Tyr Lys Cys Lys Val Ser Asn Lys Gly Leu Pro
305                 310                 315                 320

Ser Ser Ile Glu Lys Thr Ile Ser Lys Ala Lys Gly Gln Pro Arg Glu
                325                 330                 335

Pro Gln Val Tyr Thr Leu Pro Pro Ser Gln Glu Glu Met Thr Lys Asn
            340                 345                 350

Gln Val Ser Leu Thr Cys Leu Val Lys Gly Phe Tyr Pro Ser Asp Ile
        355                 360                 365

Ala Val Glu Trp Glu Ser Asn Gly Gln Pro Glu Asn Asn Tyr Lys Thr
    370                 375                 380

Thr Pro Pro Val Leu Asp Ser Asp Gly Ser Phe Phe Leu Tyr Ser Arg
385                 390                 395                 400

Leu Thr Val Asp Lys Ser Arg Trp Gln Glu Gly Asn Val Phe Ser Cys
                405                 410                 415

Ser Val Met His Glu Ala Leu His Asn His Tyr Thr Gln Lys Ser Leu
            420                 425                 430

Ser Leu Ser Leu Gly Lys
        435

<210> SEQ ID NO 37
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asn Val Val Thr Asn
            20                  25                  30

Val Ala Trp Tyr Gln Gln Lys Pro Gly Lys Ser Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asn Ser Tyr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 38
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile His Tyr Ser Gly Ile Ala Asn Tyr Asn Pro Ser Leu
    50                  55                  60

Lys Ser Arg Ile Ser Ile Thr Arg Asp Thr Ser Lys Asn His Phe Phe
65                  70                  75                  80

Leu Gln Leu Asn Ser Val Thr Thr Glu Asp Thr Ala Thr Tyr Tyr Cys
                85                  90                  95

Ala Thr Glu Lys Thr Gly Phe Phe Asp Tyr Trp Gly Gln Gly Thr Thr
            100                 105                 110

Leu Thr Val Ser Ser
        115

<210> SEQ ID NO 39
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Ala His Val Pro Pro Thr Phe Gly Gly Gly Thr Lys Leu Glu Ile Lys
            100                 105                 110
```

Arg

<210> SEQ ID NO 40
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ala Val Gln Leu Gln Glu Ser Gly Pro Asp Leu Val Lys Pro Ser His
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile His Tyr Ser Gly Ser Ala Asn Tyr Asn Pro Ser Leu
    50                  55                  60

Lys Ser Arg Phe Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Thr Glu Lys Thr Gly Phe Phe Asp Tyr Trp Gly Gln Gly Thr Thr
            100                 105                 110

Leu Thr Val Ser Ser
        115

<210> SEQ ID NO 41
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Ala His Val Pro Pro Thr Phe Gly Gly Gly Thr Lys Leu Glu Ile Lys
            100                 105                 110

Arg

<210> SEQ ID NO 42
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 42

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Ala Ser Gly
            20                  25                  30

Tyr Ser Trp His Trp Ile Arg Gln Phe Pro Gly Asn Lys Leu Glu Trp
        35                  40                  45

Met Gly Tyr Ile His Phe Ser Gly Ser Ala Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Ser Glu Ala Arg Gly Tyr Phe Asp Tyr Trp Gly Gln Gly Thr Thr
            100                 105                 110

Leu Thr Val Ser Ser
        115

<210> SEQ ID NO 43
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Arg Ser
            20                  25                  30

Asn Gly Asn Thr Tyr Leu Thr Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Ser His Val Pro Pro Thr Phe Gly Ser Gly Thr Lys Leu Glu Ile Lys
            100                 105                 110

Arg

<210> SEQ ID NO 44
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Ser
            20                  25                  30

Ala Met Thr Trp Val Arg Gln Thr Pro Glu Lys Arg Leu Glu Trp Val
```

```
            35                  40                  45
Ala Ser Ile Ser Gly Gly Thr Thr Tyr Tyr Pro Asp Ser Val Lys
 50                  55                  60

Gly Arg Phe Thr Ile Ser Arg Asp Asn Ala Arg Asn Ile Leu Tyr Leu
 65                  70                  75                  80

Gln Met Ser Ser Leu Arg Ser Glu Asp Thr Ala Ile Tyr Tyr Cys Ala
                     85                  90                  95

Arg Ser His Tyr Trp Gly Gln Gly Thr Thr Leu Thr Val Ser Ser
                100                 105                 110
```

<210> SEQ ID NO 45
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Asp Ile Val Met Thr Gln Ser Gln Lys Phe Met Ser Thr Ser Ile Gly
 1                   5                  10                  15

Asp Arg Val Ser Val Thr Cys Lys Ala Ser Gln Asn Val Thr Asn
                 20                  25                  30

Val Ala Trp Tyr Gln Gln Lys Pro Gly Gln Ser Pro Lys Ala Leu Ile
             35                  40                  45

Tyr Ser Ala Ser Tyr Arg Tyr Ser Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Asn Ser Tyr Pro Tyr
                     85                  90                  95

Thr Phe Gly Gly Gly Thr Lys Leu Glu Ile Lys Arg
                100                 105
```

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

```
Cys Pro Ser Cys
 1
```

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

```
Cys Pro Pro Cys
 1
```

<210> SEQ ID NO 48
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 48

Thr Tyr Ser Ser Pro Glu Asp Gly Ile His Glu Leu Phe Pro
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Tyr Ser Ser Pro Glu Asp Gly Ile His Glu Leu Phe Pro
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Thr Ala Ser Ser Pro Glu Asp Gly Ile His Glu Leu Phe Pro
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Tyr Ala Ser Pro Glu Asp Gly Ile His Glu Leu Phe Pro
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Tyr Ser Ala Pro Glu Asp Gly Ile His Glu Leu Phe Pro
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Tyr Ser Ser Ala Glu Asp Gly Ile His Glu Leu Phe Pro
1               5                   10
```

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Thr Tyr Ser Ser Pro Ala Asp Gly Ile His Glu Leu Phe Pro
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Tyr Ser Ser Pro Glu Ala Gly Ile His Glu Leu Phe Pro
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Tyr Ser Ser Pro Glu Asp Ala Ile His Glu Leu Phe Pro
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Tyr Ser Ser Pro Glu Asp Gly Ala His Glu Leu Phe Pro
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Thr Tyr Ser Ser Pro Glu Asp Gly Ile Ala Glu Leu Phe Pro
1               5                   10

<210> SEQ ID NO 59
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 59

Thr Tyr Ser Ser Pro Glu Asp Gly Ile His Ala Leu Phe Pro
1               5                   10

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Thr Tyr Ser Ser Pro Glu Asp Gly Ile His Glu Ala Phe Pro
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Tyr Ser Ser Pro Glu Asp Gly Ile His Glu Leu Ala Pro
1               5                   10

<210> SEQ ID NO 62
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Thr Tyr Ser Ser Pro Glu Asp Gly Ile His Glu Leu Phe Ala
1               5                   10

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Ile His Glu Leu
1               5
```

IMMUNOGLOBULIN-LIKE MOLECULES DIRECTED AGAINST FIBRONECTIN-EDA

FIELD OF THE INVENTION

The present invention is in the field of medicine, in particular in the field of cardiology and angiogenesis. The invention provides immunoglobulin (Ig)-like molecules, such as antibodies, and antigen-binding fragments thereof that bind specifically to the EDA-domain of fibronectin-EDA. These Ig-like molecules are particularly suited for treating, preventing or preventing the progression of adverse cardiac or vascular remodelling and myocardial infarction-related complications and for improving or stimulating angiogenesis. The invention also relates to pharmaceutical compositions comprising the Ig-like molecules, e.g., antibodies, or antigen-binding or fragments thereof and methods using the Ig-like molecules, e.g., antibodies, or antigen-binding or fragments thereof for treating, preventing or preventing the progression of myocardial infarction-related complications and adverse cardiac or vascular remodelling and for improving or stimulating angiogenesis.

BACKGROUND OF THE INVENTION

Ischemic heart disease is the largest socio-economic burden to Western societies. It becomes an even bigger problem in this era of rapid modernization of developing countries like China and India. The most severe and acute complication of ischemic heart disease is a heart attack, also known as myocardial infarction. In the USA, EU and Japan, 2.4 million patients suffer from a myocardial infarction each year. The amount of money spent in the USA and the EU only for the treatment of ischemic heart disease exceeds €150 billion every year. Unfortunately, myocardial infarction-related complications or conditions are increasing because more patients survive the initial life-threatening infarction, but have progressively worse cardiac function afterwards. Complications after myocardial infarction such as heart failure, fibrosis and arrhythmia result in high mortality rates and morbidity. The most important determinant of these complications is an improper cardiac repair response, referred to as adverse (cardiac) remodelling or adverse ventricular remodelling.

Heart failure (HF) has gained much attention, as it is the most severe and most frequent consequence of adverse remodelling after myocardial infarction. The European Society of Cardiology (ESC) stated that "HF is the epidemic of the 21$^{st}$ century in Western societies". In the USA, EU and Japan alone, at least 1.8 million patients are hospitalized with newly diagnosed infarction-related HF each year. The mortality rate is 20% within a year from diagnosis, while 50% die within 5 years. Quality of life of those that survive is severely affected as they suffer from progressively decreasing exercise tolerance and reduced capacity to conduct normal daily activities. The socio-economic burden is nearly €60 billion annually for the USA and EU only, as a consequence of 1) the reduced exercise tolerance and subsequent reduced productivity, 2) expensive medical treatments that are not preventive or curative but decrease symptoms and 3) rehospitalisation. Current therapy for myocardial infarction aims at restoring blood flow through the occluded coronary artery. Anti-thrombotics (i.e., agents preventing blood clot formation) together with stents are the most important drug and device classes to optimize blood flow restoration after myocardial infarction. Despite these advances in blood flow optimization, infarction-related complications still occur and are increasing. The main reason is the fact that adverse remodelling is a completely different pathophysiological process than is blood flow restoration.

The healing of the infarcted heart is a very complex process involving many types of cells. Myocardial infarction is an acute event in which part of the heart muscle dies resulting in loss of pump function. Immediately after this acute event, repair processes are induced in the blood and the heart muscle, characterized by enhanced inflammation. However, the type of inflammation determines whether the infarcted heart is repaired and remodelled properly. The key factor that drives improper healing and deleterious inflammation is the activation of innate immunity by molecules related to cardiac death and matrix degradation. In many patients, the immune system becomes activated in a detrimental way, resulting in inappropriate healing of the heart after myocardial infarction. In those cases, the heart will enter a process called adverse remodelling. Adverse remodelling has several deleterious consequences: heart failure, dilatation and fibrosis of the heart, disturbed contractility and relaxation, and disturbed electrical activation are known complications. The increasing incidence of infarction-related morbidity, like heart failure, emphasizes the need for novel therapeutics to enhance cardiac repair after infarction. Another factor contributing to healing of the infarcted heart, in particular in the early stage following myocardial infarction, is angiogenesis. De novo formation of microvessels has the potential to recover ischemic myocardium at early stages after myocardial information, contributes to prevent the transition to heart failure.

The main determinant for leukocytes to cause a deleterious inflammatory reaction is the deposition of fibronectin-EDA. After myocardial infarction, fibronectin-EDA is newly synthesized and transiently upregulated in the infarcted myocardium. Fibronectin-EDA can activate the immune system and other cells involved in matrix turnover, thereby inducing the migration and differentiation of cells involved in cardiac repair (e.g. leukocytes, lymphocytes and fibroblasts). Subsequently, cells activated by fibronectin-EDA induce detrimental inflammatory reactions in the healing heart.

Cellular fibronectin is a multifunctional adhesive glycoprotein present in the ECM and is produced by cells in response to tissue injury as occurs with MI. It contains an alternatively spliced exon encoding type III repeat extra domain A (EIIIA; EDA), that acts as an endogenous ligand for both TLR2 and TLR4 and integrin $\alpha 4\beta 1$, $\alpha 4\beta 7$ and $\alpha 9\beta 1$. In vitro, fibronectin-EDA induces pro-inflammatory gene expression and activates monocytes. In vivo injection of fibronectin-EDA in murine joints results in enhanced inflammation. Fibronectin-EDA is not normally expressed in healthy human tissue, but is highly upregulated in newly developing vasculature during embryogenesis and in several (pathological) conditions such as (cardiac) ischemic tissue, atherosclerotic lesions, fibrotic tissue, tumors, transplant rejection and wounds. Overexpression of EDA results in enhanced inflammation and injury after brain ischemia. Thus, fibronectin-EDA is capable of activating leukocytes and cause an upregulation of cytokines and chemokines. It was recently shown that fibronectin-EDA knockout mice exhibited reduced fibrosis, preserved cardiac function and reduced ventricular dilatation compared to wild-type mice after myocardial infarction (Arslan F. et al. Circ. Res., March 2011; 108: 582-592). WO2012/057613 describes that treatment of mice with antibodies directed to the EDA domain of fibronectin-EDA prevents left ventricular dilatation in said mice and improves survival after myocardial infarction.

There remains a need in the art for antibodies that are capable of treating, preventing, or preventing the progression of myocardial infarction-related conditions in a subject and that increase the chance of survival of a subject after myocardial infarction. It is an object of the present invention to provide for such antibodies.

SUMMARY OF THE INVENTION

The present invention provides an isolated immunoglobulin (Ig)-like molecule or antigen-binding fragment thereof specifically binding to an amino acid sequence GIXXXF (SEQ ID NO:1), wherein X may be any amino acid.

In an embodiment, the amino acid at position 3 of SEQ ID NO:1 is selected from histidine, arginine, lysine and alanine, and preferably is histidine.

In an embodiment, the amino acid at position 4 of SEQ ID NO: 1 is selected from glutamic acid and alanine, and preferably is glutamic acid.

In an embodiment, the amino acid at position 5 of SEQ ID NO:1 is selected from leucine and alanine, and preferably is leucine.

In an embodiment, the Ig-like molecule or fragment thereof specifically binds to an amino acid sequence GIHELF (SEQ ID NO:2).

The present invention further provides an isolated immunoglobulin (Ig)-like molecule or antigen-binding fragment thereof specifically binding to an amino acid sequence LFPAP (SEQ ID NO:28).

The Ig-like molecule or antigen-binding fragment thereof may be an antibody, e.g., a monoclonal antibody. The Ig-like molecule or antigen-binding fragment thereof may be of murine origin, e.g., may be derived from a mouse. The Ig-like molecule or antigen-binding fragment thereof may be chimeric, humanized or human.

The invention also pertains to an Ig-like molecule or antigen-binding fragment thereof comprising a heavy chain variable region comprising a complementarity determining region (CDR)1 having the amino acid sequence shown in SEQ ID NO:3 or an amino acid sequence as shown in SEQ ID NO:3, wherein at most 2, preferably at most 1 amino acid is substituted, a CDR2 having the amino acid sequence shown in SEQ ID NO:4 or an amino acid sequence as shown in SEQ ID NO:4, wherein at most 2, preferably at most 1 amino acid is substituted, and a CDR3 having the amino acid sequence shown in SEQ ID NO:5 or an amino acid sequence as shown in SEQ ID NO:5, wherein at most 3, preferably at most 2, more preferably at most 1 amino acid is substituted.

In an embodiment, the present invention relates to an Ig-like molecule or antigen-binding fragment thereof comprising a heavy chain variable region comprising:
  a CDR1 having the amino acid sequence GYSIX$_1$SGYSWH, wherein X$_1$ is selected from T and A;
  a CDR2 having the amino acid sequence YIHX$_2$SGX$_3$ANYNPSLKS, wherein X$_2$ is selected from Y and F, and wherein X$_3$ is selected from S and I;
  a CDR3 having the amino acid sequence EX$_4$X$_5$GXGFDY, wherein X$_4$ is selected from K and A, X$_5$ is selected from T and R, and X$_6$ is selected from F and Y.

The present invention also relates to an Ig-like molecule or antigen-binding fragment thereof comprising a light chain variable region comprising a CDR1 having the amino acid sequence shown in SEQ ID NO:6 or an amino acid sequence as shown in SEQ ID NO:6, wherein at most 3, preferably at most 2, more preferably at most 1 amino acid is substituted, a CDR2 having the amino acid sequence shown in SEQ ID NO:7 or an amino acid sequence as shown in SEQ ID NO:7, wherein at most 2, preferably at most 1 amino acid is substituted, and a CDR3 having the amino acid sequence shown in SEQ ID NO:8 or an amino acid sequence as shown in SEQ ID NO:8, wherein at most 3, preferably at most 2, more preferably at most 1 amino acid is substituted.

In an embodiment, the present invention provides an Ig-like molecule or antigen-binding fragment thereof comprising a light chain variable region comprising:
  a CDR1 having the amino acid sequence RSSQSX$_7$VX$_8$SNGNTYLX$_9$, wherein X$_7$ is selected from L and I, X$_8$ is selected from H and R, and X$_9$ is selected from H and T;
  a CDR2 having the amino acid sequence KVSNRFS;
  a CDR3 having the amino acid sequence X$_{10}$QX$_{11}$X$_{12}$HVPPT, wherein X$_{10}$ is selected from S and F, X$_{11}$ is selected from S and G, and X$_{12}$ is selected from A and S.

The present invention further relates to an Ig-like molecule or antigen-binding fragment thereof comprising a heavy chain variable region comprising a CDR1 having the amino acid sequence shown in SEQ ID NO:3 or an amino acid sequence as shown in SEQ ID NO:3, wherein at most 2, preferably at most 1 amino acid is substituted, a CDR2 having the amino acid sequence shown in SEQ ID NO:4 or an amino acid sequence as shown in SEQ ID NO:4, wherein at most 2, preferably at most 1 amino acid is substituted, and a CDR3 having the amino acid sequence shown in SEQ ID NO:5 or an amino acid sequence as shown in SEQ ID NO:5, wherein at most 3, preferably at most 2, more preferably at most 1 amino acid is substituted; and a light chain variable region comprising a CDR1 having the amino acid sequence shown in SEQ ID NO:6 or an amino acid sequence as shown in SEQ ID NO:6, wherein at most 3, preferably at most 2, more preferably at most 1 amino acid is substituted, a CDR2 having the amino acid sequence shown in SEQ ID NO:7 or an amino acid sequence as shown in SEQ ID NO:7, wherein at most 2, preferably at most 1 amino acid is substituted, and a CDR3 having the amino acid sequence shown in SEQ ID NO:8 or an amino acid sequence as shown in SEQ ID NO:8, wherein at most 3, preferably at most 2, more preferably at most 1 amino acid is substituted.

In an embodiment, such Ig-like molecule or antigen-binding fragment comprises a heavy chain variable region comprising
  a CDR1 having the amino acid sequence GYSIX$_1$SGYSWH, wherein X$_1$ is selected from T and A;
  a CDR2 having the amino acid sequence YIHX$_2$SGX$_3$ANYNPSLKS, wherein X$_2$ is selected from Y and F, and wherein X$_3$ is selected from S and I;
  a CDR3 having the amino acid sequence EX$_4$X$_5$GXGFDY, wherein X$_4$ is selected from K and A, X$_5$ is selected from T and R, and X$_6$ is selected from F and Y; and a light chain variable region comprising:

a CDR1 having the amino acid sequence RSSQSX$_7$VX$_8$SNGNTYLX$_9$, wherein X$_7$ is selected from L and I, X$_8$ is selected from H and R, and X$_9$ is selected from H and T;
a CDR2 having the amino acid sequence KVSNRFS;
a CDR3 having the amino acid sequence X$_{10}$QX$_{11}$X$_{12}$HVPPT, wherein X$_{10}$ is selected from S and F, X$_{11}$ is selected from S and G, and X$_{12}$ is selected from A and S.

In one embodiment, the Ig-like molecule, antibody or antigen-binding fragment thereof comprises a heavy chain variable region comprising:
a CDR1 having the amino acid sequence shown in SEQ ID NO:9;
a CDR2 having the amino acid sequence shown in SEQ ID NO:10; and
a CDR3 having the amino acid sequence shown in SEQ ID NO:11;
and a light chain variable region comprising:
a CDR1 having the amino acid sequence shown in SEQ ID NO:12;
a CDR2 having the amino acid sequence shown in SEQ ID NO:13; and
a CDR3 having the amino acid sequence shown in SEQ ID NO:14.

Preferably, said Ig-like molecule, antibody or antigen-binding fragment thereof comprises a humanized heavy chain variable region of the heavy chain variable region having the amino acid sequence of SEQ ID NO:40 and a humanized light chain variable region of the light chain variable region having the amino acid sequence of SEQ ID NO:41.

In another embodiment, the Ig-like molecule, antibody or antigen-binding fragment thereof comprises a heavy chain variable region comprising:
a CDR1 having the amino acid sequence shown in SEQ ID NO:3;
a CDR2 having the amino acid sequence shown in SEQ ID NO:4; and
a CDR3 having the amino acid sequence shown in SEQ ID NO:5;
and a light chain variable region comprising:
a CDR1 having the amino acid sequence shown in SEQ ID NO:6;
a CDR2 having the amino acid sequence shown in SEQ ID NO:7; and
a CDR3 having the amino acid sequence shown in SEQ ID NO:8.

Preferably, said Ig-like molecule, antibody or antigen-binding fragment thereof comprises a humanized heavy chain variable region of the heavy chain variable region having the amino acid sequence of SEQ ID NO:38 and a humanized light chain variable region of the light chain variable region having the amino acid sequence of SEQ ID NO:39.

In yet another embodiment, the Ig-like molecule, antibody or antigen-binding fragment thereof comprises a heavy chain variable region comprising:
a CDR1 having the amino acid sequence shown in SEQ ID NO:15;
a CDR2 having the amino acid sequence shown in SEQ ID NO:16; and
a CDR3 having the amino acid sequence shown in SEQ ID NO:17;
and a light chain variable region comprising:
a CDR1 having the amino acid sequence shown in SEQ ID NO:18;
a CDR2 having the amino acid sequence shown in SEQ ID NO:19; and
a CDR3 having the amino acid sequence shown in SEQ ID NO:20.

Preferably, said Ig-like molecule, antibody or antigen-binding fragment thereof comprises a humanized heavy chain variable region of the heavy chain variable region having the amino acid sequence of SEQ ID NO:42 and a humanized light chain variable region of the light chain variable region having the amino acid sequence of SEQ ID NO:43.

The present invention further provides an Ig-like molecule or antigen-binding fragment thereof comprising a heavy chain variable region comprising a complementarity determining region (CDR)1 having the amino acid sequence shown in SEQ ID NO:29 or an amino acid sequence as shown in SEQ ID NO:29 wherein at most 2, preferably at most 1 amino acid is substituted, a CDR2 having the amino acid sequence shown in SEQ ID NO:30 or an amino acid sequence as shown in SEQ ID NO:30, wherein at most 2, preferably at most 1 amino acid is substituted, and a CDR3 having the amino acid sequence SHY.

The invention also provides an Ig-like molecule or antigen-binding fragment thereof comprising a light chain variable region comprising a CDR1 having the amino acid sequence shown in SEQ ID NO:31 or an amino acid sequence as shown in SEQ ID NO:31, wherein at most 2, preferably at most 1 amino acid is substituted, a CDR2 having the amino acid sequence shown in SEQ ID NO:32 or an amino acid sequence as shown in SEQ ID NO:32, wherein at most 2, preferably at most 1 amino acid is substituted, and a CDR3 having the amino acid sequence shown in SEQ ID NO:33 or an amino acid sequence as shown in SEQ ID NO:33, wherein at most 2, preferably at most 1 amino acid is substituted.

In an embodiment, Ig-like molecule or antigen-binding fragment thereof comprises a heavy chain variable region comprising a CDR1 having the amino acid sequence shown in SEQ ID NO:29 or an amino acid sequence as shown in SEQ ID NO:29, wherein at most 2, preferably at most 1 amino acid is substituted, a CDR2 having the amino acid sequence shown in SEQ ID NO:30 or an amino acid sequence as shown in SEQ ID NO:30, wherein at most 2, preferably at most 1 amino acid is substituted, and a CDR3 having the amino acid sequence SHY, and further comprising a light chain variable region comprising a CDR1 having the amino acid sequence shown in SEQ ID NO:31 or an amino acid sequence as shown in SEQ ID NO:31, wherein at most 2, preferably at most 1 amino acid is substituted, a CDR2 having the amino acid sequence shown in SEQ ID NO:32 or an amino acid sequence as shown in SEQ ID NO:32, wherein at most 2, preferably at most 1 amino acid is substituted, and a CDR3 having the amino acid sequence shown in SEQ ID NO:33 or an amino acid sequence as shown in SEQ ID NO:33, wherein at most 2, preferably at most 1 amino acid is substituted. In one embodiment, the Ig-like molecule, antibody or antigen-binding fragment thereof comprises a heavy chain variable region comprising:
a CDR1 having the amino acid sequence shown in SEQ ID NO:29;
a CDR2 having the amino acid sequence shown in SEQ ID NO:30; and
a CDR3 having the amino acid sequence SHY;
and a light chain variable region comprising:
a CDR1 having the amino acid sequence shown in SEQ ID NO:31;

a CDR2 having the amino acid sequence shown in SEQ ID NO:32; and a CDR3 having the amino acid sequence shown in SEQ ID NO:33.

Preferably, said Ig-like molecule, antibody or antigen-binding fragment thereof comprises a humanized heavy chain variable region of the heavy chain variable region having the amino acid sequence of SEQ ID NO:44 and a humanized light chain variable region of the light chain variable region having the amino acid sequence of SEQ ID NO:45.

In an embodiment, the CDRs of the light chain and/or the heavy chain are integrated into human-derived framework regions.

The Ig-like molecule or antigen-binding fragment thereof may be an antibody, e.g., a chimeric antibody or a humanized antibody.

The invention also provides a nucleic acid molecule encoding the Ig-like molecule or antigen-binding fragment thereof taught herein, and a vector comprising such nucleic acid molecule. Such vector may be a gene therapy vector.

Additionally, the invention provides a host cell comprising the nucleic acid molecule taught herein or the vector taught herein. The host cell may be a mammalian host cell. The host cell may be a hybridoma.

The invention also provides a pharmaceutical composition comprising an agent selected from the group consisting of (a) the Ig-like molecule or antigen-binding fragment thereof as taught herein, (b) a nucleic acid molecule encoding the Ig-like molecule or antigen-binding fragment thereof, (c) a vector comprising such nucleic acid molecule and (d) a host cell comprising such nucleic acid molecule or such vector, and a pharmaceutically acceptable carrier.

The invention further provides an Ig-like molecule or antigen-binding fragment thereof or pharmaceutical composition as taught herein for use as a medicament, particularly for use in the treatment, prevention or prevention of the progression of adverse cardiac remodelling and conditions resulting from or relating to myocardial infarction and/or pressure overload, or for use in the treatment, prevention or prevention of the progression of adverse tissue remodelling, in particular fibronectin-EDA mediated adverse tissue remodelling.

The present invention further provides a method of treating, preventing or preventing progression of adverse cardiac remodelling and conditions resulting from or relating to myocardial infarction and/or pressure overload, which comprises administering to a subject in need thereof, a therapeutically effective amount of an agent selected from the group consisting of (a) the Ig-like molecule or antigen-binding fragment thereof as taught herein, a nucleic acid molecule encoding the Ig-like molecule or antigen-binding fragment thereof, (c) a vector comprising such nucleic acid molecule and (d) a host cell comprising such nucleic acid molecule or such vector. The subject may be human.

The present invention further provides an antibody that binds fibronectin-EDA or an antigen-binding fragment thereof for use in improving angiogenesis and a method for improving angiogenesis comprising administering to a subject in need thereof a therapeutically effective amount of an antibody that binds fibronectin-EDA or an antigen-binding fragment thereof. The subject may be human.

DETAILED DESCRIPTION OF THE INVENTION

Immunoglobulin-Like Molecules, Antibodies and Antigen-Binding Fragments Thereof.

In a first aspect, the invention relates to an isolated Ig-like molecule or antigen-binding fragment thereof that specifically binds to the amino acid sequence GIXXXF (SEQ ID NO:1), wherein X can be any amino acid or to amino acid sequence LFPAP (SEQ ID NO:28).

The term "isolated" as used herein refer to material which is substantially or essentially free from components which normally accompany it in nature.

The term "immunoglobulin" (abbreviated as "Ig") as used herein is well-known in the art and equals the term "antibody". The term "Ig-like molecule" as used herein refers to any polypeptide comprising an antigen-binding site with at least one complementarity determining region (CDR). The term includes, but is not limited to polyclonal antibodies, monoclonal antibodies, monospecific antibodies, multispecific antibodies, humanized antibodies, chimeric antibodies, human antibodies, and single-chain antibodies (e.g., VHH). The term "Ig-like molecule" also includes antibody fragments such Fab, F(ab')$_2$, Fv, scFv, Fd, dAb, and other antibody fragments or other constructs comprising CDRs that retain antigen-binding function. Typically, such fragments would comprise an antigen-binding domain. The Ig-like molecules or antigen-binding fragments thereof may be any of the known antibody isotypes and their conformations, for example, IgA, such as IgA1 or IgA2, IgD, IgE, IgG, such as IgG1, IgG2a, IgG2b, IgG3, IgG4, or IgM class, or may constitute mixtures thereof in any combination, such as a mixture of antibodies from the IgG1 and IgG2a class. In a preferred embodiment the Ig-like molecules, antibodies or antigen-binding fragment are of the IgG4 isotype, more preferably a stabilized IgG4 with reduced dissociation of intrachain bonds resulting in the relatively high levels of IgG4 half-molecules.

Immunoglobulins or antibodies are immune system-related proteins. Each antibody consists of four polypeptides—two heavy chains and two light chains joined to form a "Y"-shaped molecule. The amino acid sequence in the tips of the "Y" varies greatly among different antibodies. This variable region, composed of 110-130 amino acids, gives the antibody its specificity for binding antigen. The variable region includes the ends of the light and heavy chains. The constant region determines the mechanism used to destroy antigen. Antibodies are divided into five major classes, IgM, IgG, IgA, IgD, and IgE, based on their heavy chain constant region structure and immune function. Also subclasses of the heavy chain are known. For example, IgG heavy chains in humans can be any of the IgG1, IgG2, IgG3 and IgG4 subclasses.

The variable region is subdivided into hypervariable (HV) and framework (FR) regions. HV regions have a high ratio of different amino acids in a given position, relative to the most common amino acid in that position. Within light and heavy chains, three HV regions exist—HV 1, 2 and 3. Four FR regions, which have more stable amino acids sequences, separate the HV regions. The HV regions directly contact a portion of the antigen's surface. For this reason, HV regions are also sometimes referred to as complementarity determining regions, or CDRs. The FR regions form a beta-sheet structure which serves as a scaffold to hold the HV regions in position to contact antigen. The term "antigen" as used herein refers to the target molecule that binds specifically to the respective antibody. Antigens usually present several surface features that can act as points of interaction for specific antibodies. Any such surface feature may constitute an epitope. Therefore, most antigens have the potential to be bound by several distinct antibodies, each of which may bind to a different epitope.

The Ig-like molecules, antibodies, or antigen-binding fragments as taught herein are capable of binding to fibronectin-EDA or solely the EDA domain of fibronectin-EDA or a part of the EDA domain of fibronectin-EDA such as a specific amino acid region, particularly the amino acid sequence GIXXXF, wherein X can be any amino acid, as set forth in SEQ ID NO:1, or the amino acid sequence LFPAP (SEQ ID NO:28).

In the present invention, the term "antigen-binding fragment" is understood as a part or portion of an Ig-like molecule, e.g., antibody, as taught herein, which at least comprises a domain specifically binding to the amino acid sequence as set forth in SEQ ID NO:1, SEQ ID NO:2 and/or SEQ ID NO:28. Antigen-binding fragments may be obtained via chemical or enzymatic treatment of an intact or complete Ig-like molecule, e.g., antibody. Alternatively, antigen-binding fragments may be obtained using standard molecular biology techniques and protocols. Non-limiting examples of antigen-binding fragments of Ig-like molecules include Fab, Fab', F(ab')2, and Fv fragments; diabodies; linear antibodies and single-chain antibody molecules.

In an embodiment, the antigen-binding fragment comprises at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, or at least 150 contiguous amino acid residues of the amino acid sequence of an Ig-like molecule that specifically binds to the EDA domain of fibronectin-EDA as taught herein, preferably the N-terminal portion of an antibody specifically binding to the EDA domain of fibronectin-EDA, more preferably to the amino acid sequence as set forth in SEQ ID NO:1, SEQ ID NO:2 and/or 28. The antigen-binding fragment preferably retains the antigen-binding specificity of the Ig-like molecule.

In a preferred embodiment, the antigen-binding fragment comprises all three CDRs, i.e. CDR1, CDR2, and CDR3, of both the heavy and light chains. In an even more preferred embodiment, the antigen-binding fragment comprises the entire variable domain of both the heavy and light chains.

Preferably, the Ig-like molecule, e.g. an antibody or antigen-binding fragment thereof binds specifically to the EDA domain of fibronectin-EDA. In a preferred embodiment, the Ig-like molecule, e.g. an antibody or antigen-binding fragment thereof specifically binds to a part of the EDA domain of fibronectin-EDA, wherein said part has the amino acid sequence as set forth in SEQ ID NO 1. "An antibody or antigen-binding fragment thereof that binds fibronectin-EDA" as used herein refers to an antibody or antigen-binding fragment thereof that specifically bind to the EDA domain of fibronectin. Such antibody or fragment does not bind fibronectin lacking the type III repeat extra domain A (EIIIA; EDA).

The skilled person is aware of the meaning of the term 'specifically binding'. The term "specifically binding" as used herein means that an Ig-like molecule or antibody or a fragment thereof as taught herein exhibits appreciable binding affinity for an antigen or a particular epitope and, preferably, does not exhibit significant cross-reactivity. "Appreciable" binding affinity includes binding with an affinity of at least $10^6$ M$^{-1}$, preferably at least $10^7$ M$^{-1}$, more preferably at least $10^8$ M$^{-1}$, yet more preferably at least $10^9$ M$^{-1}$, or even yet more preferably at least $10^{10}$ M$^{-1}$. An antibody that "does not exhibit significant cross-reactivity" is one that will not appreciably bind to an undesirable entity or tissue where fibronectin-EDA expression is absent. Specific binding can be determined according to any art-recognized means for determining such binding. For example, specific binding may be determined according to Scatchard analysis and/or competitive binding assays or other assays accepted in the field.

In an embodiment of the invention, the Ig-like molecules as taught herein are antibodies, preferably monoclonal antibodies. The term "monoclonal antibody" is well known in the art. It is understood to refer to an antibody that is the product of a single cloned antibody-producing cell. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that is capable of producing the antibody. Monoclonal antibodies can be produced by a variety of routine techniques.

The Ig-like molecules, antibodies or antigen-binding fragments thereof as taught herein may be of any immunoglobulin isotype, such as IgG, IgM, IgA, IgD, and IgE. In a preferred embodiment, the Ig-like molecules, antibodies or antigen-binding fragments thereof as taught herein are IgG, such as IgG1, IgG2, IgG3 or IgG4, preferably IgG4. In an embodiment, the monoclonal antibodies or antigen-binding fragments thereof as taught herein are from mammalian origin such as from human, non-human primates, sheep, rabbits, pigs, dogs, horses, cow, chicken, and murine and other mammals.

The antibody or antigen-binding fragment thereof as taught herein may also be a hybrid antibody, e.g., a chimeric, or humanized monoclonal antibody. In the present invention, the term "hybrid antibody" refers to an antibody in which one or more regions of the antibody are derived from an antibody derived from a first species (for instance a mouse) and one or more regions of the antibody are from an antibody derived from a second, different species (for instance a human). In chimeric antibodies typically non-human (e.g., mouse) constant regions of the antibody are substituted by human constant regions.

A humanized antibody is understood to refer to an antibody where at least one of the heavy and light chain is humanized, i.e. at least one of the heavy and light chain comprises a variable region wherein one or more, preferably all, of the framework regions are primarily human. The hypervariable (CDR) regions of the humanized antibody may be derived from a non-human source, typically of a rodent (for instance a mouse). The humanized antibody may optionally comprise at least a portion of an Ig constant region (Fc), preferably that of a human Ig molecule.

Chimeric and humanized antibodies may be prepared by methods well known in the art including CDR grafting approaches (see, e.g., U.S. Pat. Nos. 5,843,708; 6,180,370; 5,693,762; 5,585,089; 5,530,101), chain shuffling strategies (see e.g., U.S. Pat. No. 5,565,332; Rader et al., Proc. Natl. Acad. Sci. USA (1998) 95:8910-8915), molecular modelling strategies (U.S. Pat. No. 5,639,641), and the like. For instance, a best-fit human heavy and light chain is selected based on 3D models and CDR lengths of a non-human antibody. Subsequently, amino acids in the framework regions that differ between the human and non-human antibody and that may influence antigen binding are identified. The use of chimeric or humanized antibodies or antigen-binding fragments thereof may minimize or eliminate the occurrence or risk of immune-rejections or other adverse immune responses in humans. In addition generally a longer half-life in the circulation is achieved when chimeric, humanized or human antibodies are used because of reduced clearance when compared to non-human antibodies.

In a particularly preferred embodiment, an antibody of the invention is a humanized antibody. A humanized antibody according in accordance with the invention preferably comprises a human heavy chain and a light chain constant region, and more preferably further comprises human heavy chain and light chain framework regions. As examples, the present invention provides humanized antibodies of murine antibodies 27A12.70 and 33E3.10. Germline genes VK2-29 and JK4 are used as acceptor sequences for the light chain of humanized antibody 27A12.70 and germline genes VH4-31 and JH4 are used as acceptor sequence for the heavy chain of humanized antibody 27A12.70. SEQ ID NO:34 and SEQ ID NO:35 provide the sequences of the heavy chain and light chain, respectively, of humanized antibody 27A12.70. Germline genes VK1-12 and JK4 are used as acceptor sequences for the light chain of humanized antibody 33E3.10 and germline genes VH3-23 and JH4 are used as acceptor sequence for the heavy chain of humanized antibody 33E3.10. SEQ ID NO:36 and SEQ ID NO:37 provide the sequences of the heavy chain and light chain, respectively, of humanized antibody 33E3.10.

A particularly preferred antibody according to the invention is a humanized antibody of the IgG4 subtype. It is known in the art that IgG4 antibodies behave differently in vivo than other IgG subtype antibodies. IgG4 molecules occurs both in a form in which the inter-heavy chain disulphide bonds have been formed and in form in which one or both of the bonds have not been formed. The IgG4 form in which the inter-heavy chain disulphide bonds are lacking consists of one heavy chain and one light chain, which is also referred to as a half-molecule. It is believed the cause of this flexibility of IgG4 lies in the core sequence of the IgG4 hinge region. This region consists of Cys-Pro-Ser-Cys, whereas the corresponding sequence in IgG1 and IgG2 is Cys-Pro-Pro-Cys. The result of the IgG4 flexibility is that in vivo IgG4 is present in several forms, including half-molecules, monospecific antibodies and bispecific antibodies which have formed as a result of the association of two IgG4 molecules with different antigen specificity. For therapeutic use of an antibody formation of half-molecules and bispecific antibodies is unfavourable because in vivo stability of the antibody is desired. Therefore, stabilized IgG4 molecules have been designed which have reduced half-molecule formation and exchange in vivo. In a preferred embodiment, a humanized IgG4 antibody according to the invention is a stabilized IgG4 antibody. The term "stabilized IgG4 antibody" as used herein refers to an IgG4 antibody which has been modified to reduce half-molecule formation and exchange. Examples of suitable stabilized IgG4 antibodies are antibodies, wherein arginine at position 409 in the heavy chain constant region of human IgG4, (Kabat numbering, Kabat et al. Sequences of Proteins of Immunological interest, 5th Ed. Public Health Service, National Institute of Health, Bethesda, Md., 1991) is substituted with lysine, threonine, methionine, or leucine and/or wherein the hinge region of the IgG4 comprises a Cys-Pro-Pro-Cys sequence.

The amino acid sequences of the heavy chain and light chain of preferred stabilized humanized IgG4 having the heavy and light chain CDRs of antibody 27A12.70 are shown in SEQ ID NO:34 and SEQ ID NO:35, respectively, and that of a preferred humanized IgG4 having the heavy and light chain CDRs of antibody 33E3.10 in SEQ ID NO:36 and SEQ ID NO:37, respectively. The amino acid sequence of the constant regions and framework regions of one or more of these preferred stabilized IgG4 heavy chain and light chain are in a preferred embodiment used to humanized the other antibodies disclosed herein.

Provided is therefore a humanized antibody or antigen-binding fragment thereof specifically binding to an amino acid sequence as set forth in SEQ ID NO:1 or SEQ ID NO:2, wherein the antibody or fragment thereof comprises a heavy chain and a light chain, wherein said heavy chain has an amino acid sequence as shown in SEQ ID NO:34 and said light chain has an amino acid sequence as shown in SEQ ID NO:35. Further provided is a humanized antibody or antigen-binding fragment thereof specifically binding to an amino acid sequence as set forth in SEQ ID NO:28, wherein the antibody or fragment thereof comprises a heavy chain and a light chain, wherein said heavy chain has an amino acid sequence as shown in SEQ ID NO:36 and said light chain has an amino acid sequence as shown in SEQ ID NO:37.

Further provided is a humanized antibody or antigen-binding fragment thereof specifically binding to an amino acid sequence as set forth in SEQ ID NO:1, SEQ ID NO:2 or SEQ ID NO:28, wherein the antibody or fragment thereof comprises a heavy chain and a light chain, wherein said heavy chain comprises a humanized variable region comprising one or more, preferably all, of the framework regions of an IgG4 heavy chain as set forth in SEQ ID NO:34 or SEQ ID NO:36 and wherein said light chain comprises a humanized variable region comprising one or more, preferably all, of the framework regions of an IgG4 light chain as set forth in SEQ ID NO:35 or SEQ ID NO:37. Further provided is a humanized antibody or antigen-binding fragment thereof specifically binding to an amino acid sequence as set forth in SEQ ID NO:1, SEQ ID NO:2 or SEQ ID NO:28, wherein the antibody or fragment thereof comprises a heavy chain and a light chain, wherein said heavy chain comprises a constant region of an IgG4 heavy chain as set forth in SEQ ID NO:34 or SEQ ID NO:36 (preferably amino acids 118-444 of SEQ ID NO:34 or amino acids 112-438 of SEQ ID NO:36) and said light chain comprises a constant region of an IgG4 light chain as set forth in SEQ ID NO:35 or SEQ ID NO:37 (preferably amino acids 114-219 of SEQ ID NO:35 or amino acids 109-214 of SEQ ID NO:37). Further, said heavy chain and/or light chain may comprise a variable region comprising one or more, preferably all, of the framework regions of an IgG4 heavy chain as set forth in SEQ ID NO:34 or SEQ ID NO:36 and/or a variable region comprising one or more, preferably all, of the framework regions of an IgG4 light chain as set forth in SEQ ID NO:35 or SEQ ID NO:37. Said antibody further preferably comprise heavy chain and light chain CDRs of antibody 27A12.70, 29E7.35, 17G8.72 or 33E3.10. The CDR sequences are shown in SEQ ID NO:3-8 (27A12.70), SEQ ID NO:9-14 (29E7.35), SEQ ID NO:15-20 (17G8.72) and SEQ ID NO:29-33 (33E3.10).

Further provided is therefore a humanized antibody that binds fibronectin-EDA or an antigen-binding fragment thereof for use in improving angiogenesis, preferably for use in improving angiogenesis in ischemic tissue, in fibrotic tissue, in pressure-overload conditions, in wound tissue and/or upon organ or tissue transplantation, wherein said antibody or fragment specifically bind to an amino acid sequence as set forth in SEQ ID NO:1, SEQ ID NO:2 or SEQ ID NO:28, wherein the antibody or fragment thereof comprising a heavy chain and a light chain, wherein said heavy chain comprises a constant region of an IgG4 heavy chain as set forth in SEQ ID NO:34 or SEQ ID NO:36 and said light chain comprises a constant region of an IgG4 light chain as set forth in SEQ ID NO:35 or SEQ ID NO:37. Further, said heavy chain and/or light chain, preferably both, may comprise a variable region comprising one or more, preferably all, of the framework regions of an IgG4 heavy chain as set forth in SEQ ID NO:34 or SEQ ID NO:36 and/or a variable region comprising one or more, preferably all, of the framework regions of an IgG4 light chain as set forth in SEQ ID NO:35 or SEQ ID NO:37. Said antibody further preferably comprise heavy chain and light chain CDRs of antibody 27A12.70, 29E7.35, 17G8.72 or 33 E3.10.

In one aspect, an Ig-like molecule or antigen-binding fragment taught herein specifically binds to the amino acid sequence GIXXXF (SEQ ID NO:1), wherein the X may be any amino acid.

In one embodiment, the amino acid at position 3 of SEQ ID NO:1 may be any amino acid. Alternatively, the amino acid at position 3 of SEQ ID NO:1 may be selected from histidine, arginine, lysine, and alanine. More preferably, the amino acid at position 3 of SEQ ID NO:1 is histidine.

Similarly, the amino acid at position 4 of SEQ ID NO:1 may be any amino acid. The amino acid at position 4 of SEQ ID NO:1 is preferably selected from glutamic acid and alanine. In a preferred embodiment, the amino acid at position 4 of SEQ ID NO:1 is glutamic acid.

The amino acid at position 5 of SEQ ID NO:1 may be any amino acid. Preferably, the amino acid at position 5 of SEQ ID NO:1 is a small amino acid selected from the group consisting of leucine and alanine. In a preferred embodiment, the amino acid at position 5 of SEQ ID NO:1 is leucine.

In a more preferred embodiment, the Ig-like molecules or antigen-binding fragments thereof specifically bind to the amino acid sequence GIHELF (SEQ ID NO:2). The present inventor found that Ig-like molecules or fragments thereof as taught herein bind with high affinity to the amino acid sequence as set forth in SEQ ID NO:2. The present inventor also found that Ig-like molecules, antibodies and fragments thereof as taught herein resulted in increased survival and improved cardiac function after myocardial infarction. It was further found that the Ig-like molecules, antibodies and fragments thereof as taught herein are further preferred because they do not influence the amount myofibroblasts in the heart tissue and doe not interfere with collagen production. This is advantageous because it is important to have a firm collagen based scar in this tissue to prevent rupture of the infarcted area. As demonstrated in Example 5, treatment with an antibody that binds fibronectin-EDA of the invention did not affect proper scar formation. In addition, it was found that anti-fibronectin EDA treatment delays clearance of acellular matrix. The formation of such provisional acellular matrix is crucial for hemodynamic compensation for non-viable tissue and scar formation after MI. During wound healing the provisional matrix is slowly degraded and replaced by a firm collagen-based scar.

Under non-ischemic conditions, the absence of EDA also protected against adverse remodeling after pressure-overload of the heart in mice. Both cardiac function and heart/body weight (marker for degree of heart failure and subsequent congestion) was significantly improved in EDA deficient mice. These data demonstrate that anti-EDA treatment in pressure-overload conditions (e.g. hypertension, valvular disease and non-ischemic cardiomyopathy) is of therapeutic value.

The present invention also provides an Ig-like molecule, antibody or antigen-binding fragment thereof comprising a heavy chain variable region comprising a complementarity determining region (CDR)1 having the amino acid sequence shown in SEQ ID NO:3 or an amino acid sequence as shown in SEQ ID NO:3, wherein at most 2, preferably at most 1 amino acid is substituted, a CDR2 having the amino acid sequence shown in SEQ ID NO:4 or an amino acid sequence as shown in SEQ ID NO:4, wherein at most 2, preferably at most 1 amino acid is substituted, and a CDR3 having the amino acid sequence shown in SEQ ID NO:5 or an amino acid sequence as shown in SEQ ID NO:5, wherein at most 3, such as at most 2, preferably at most 1 amino acid is substituted.

For example, it was found that the threonine at position 5 of SEQ ID NO:3 may also be an alanine. Additionally, it was found that tyrosine at position 4 of SEQ ID NO:4 may also be phenylalanine, and that isoleucine at position 7 of SEQ ID NO:4 may also be serine. Finally, it was found that lysine at position 2 of SEQ ID NO:5 may also be alanine, that threonine at position 3 of SEQ ID NO:5 may also be arginine, and that phenylalanine at position 5 of SEQ ID NO:5 may also be tyrosine.

Also provided is an Ig-like molecule, antibody or antigen-binding fragment thereof comprising:
a heavy chain variable region comprising:
- a CDR1 having the amino acid sequence GYSIX$_1$SGYSWH, wherein X$_1$ is selected from T and A (SEQ ID NO:21);
- a CDR2 having the amino acid sequence YIHX$_2$SGX$_3$ANYNPSLKS, wherein X$_2$ is selected from Y and F, and wherein X$_3$ is selected from S and I (SEQ ID NO:22);
- a CDR3 having the amino acid sequence EX$_4$X$_5$GXGFDY, wherein X$_4$ is selected from K and A, X$_5$ is selected from T and R, and X$_6$ is selected from F and Y (SEQ ID NO:23).

The invention also provides an Ig-like molecule, antibody or antigen-binding fragment thereof comprising a light chain variable region comprising a CDR1 having the amino acid sequence shown in SEQ ID NO:6 or an amino acid sequence as shown in SEQ ID NO:6, wherein at most 3, such as at most 2, preferably at most 1 amino acid is substituted, a CDR2 having the amino acid sequence shown in SEQ ID NO:7 or an amino acid sequence as shown in SEQ ID NO:7, wherein at most 2, preferably at most 1 amino acid is substituted, and a CDR3 having the amino acid sequence shown in SEQ ID NO:8 or an amino acid sequence as shown in SEQ ID NO:8, wherein at most 3, such as at most 2, preferably at most 1 amino acid is substituted.

For example, it was found that the leucine at position 6 of SEQ ID NO:6 may also be an isoleucine, that the histidine at position 8 of SEQ ID NO:6 may also be an arginine, and that the histidine at position 16 of SEQ ID NO:6 may also be a threonine. Additionally, it was found that the serine at position 1 of SEQ ID NO:8 may also be a phenylalanine, that the serine at position 3 of SEQ ID NO:8 may also be a glycine, and that the alanine at position 4 of SEQ ID NO:8 may also be a serine.

Also provided is an Ig-like molecule, antibody or antigen-binding fragment thereof comprising:
a light chain variable region comprising:
  a CDR1 having the amino acid sequence RSSQSX$_7$VX$_8$SNGNTYLX$_9$, wherein X$_7$ is selected from L and I, X$_8$ is selected from H and R, and X$_9$ is selected from H and T (SEQ ID NO: 24);
  a CDR2 having the amino acid sequence KVSNRFS (SEQ ID NO: 25);
  a CDR3 having the amino acid sequence X$_{10}$QX$_{11}$X$_{12}$HVPPT, wherein X$_{10}$ is selected from S and F, X$_{11}$ is selected from S and G, and X$_{12}$ is selected from A and S (SEQ ID NO:26).

In a preferred embodiment, such Ig-like molecule, antibody or antigen-binding fragment thereof comprises a heavy chain variable region comprising a CDR1 having the amino acid sequence shown in SEQ ID NO:3 or an amino acid sequence as shown in SEQ ID NO:3, wherein at most 2, preferably at most 1 amino acid is substituted, a CDR2 having the amino acid sequence shown in SEQ ID NO:4 or an amino acid sequence as shown in SEQ ID NO:4, wherein at most 2, preferably at most 1 amino acid is substituted, and a CDR3 having the amino acid sequence shown in SEQ ID NO:5 or an amino acid sequence as shown in SEQ ID NO:5, wherein at most 3, such as at most 2, preferably at most 1 amino acid is substituted; and a light chain variable region comprising a CDR1 having the amino acid sequence shown in SEQ ID NO:6 or an amino acid sequence as shown in SEQ ID NO:6, wherein at most 3, such as at most 2, preferably at most 1 amino acid is substituted, a CDR2 having the amino acid sequence shown in SEQ ID NO:7 or an amino acid sequence as shown in SEQ ID NO:7, wherein at most 2, preferably at most 1 amino acid is substituted, and a CDR3 having the amino acid sequence shown in SEQ ID NO:8 or an amino acid sequence as shown in SEQ ID NO:8, wherein at most 3, such as at most 2, preferably at most 1 amino acid is substituted. The present inventor found that the Ig-like molecules, antibodies or antigen-binding fragments thereof of the present embodiment are particularly suitable for treating, preventing or preventing the progression of cardiac and vascular remodelling, myocardial infarction- and pressure-overload-related complications. Specifically, the Ig-like molecules, antibodies or antigen-binding fragments thereof of the present embodiment were found to be particularly effective in increasing survival and improving cardiac function after myocardial infarction. Further, the Ig-like molecules, antibodies or antigen-binding fragments thereof of the invention are particularly preferred because they delay clearance of acellular matrix and do not affect proper scar formation, which is important to prevent dilatation and rupture of the heart after myocardial infarction. In addition, the Ig-like molecules, antibodies or antigen-binding fragments thereof of the invention are preferred because they also improve angiogenesis in the infarct and borderzone after myocardial infarction thus contributing to improved wound healing and preventing adverse remodeling.

In another preferred embodiment, such Ig-like molecule, antibody or antigen-binding fragment thereof comprises a heavy chain variable region comprising:
  a CDR1 having the amino acid sequence GYSIX$_1$SGYSWH, wherein X$_1$ is selected from T and A (SEQ ID NO:21);
  a CDR2 having the amino acid sequence YIHX$_2$SGX$_3$ANYNPSLKS, wherein X$_2$ is selected from Y and F, and wherein X$_3$ is selected from S and I (SEQ ID NO:22); and
  a CDR3 having the amino acid sequence EX$_4$X$_5$GXGFDY, wherein X$_4$ is selected from K and A, X$_5$ is selected from T and R, and X$_6$ is selected from F and Y (SEQ ID NO:23);
and a light chain variable region comprising:
  a CDR1 having the amino acid sequence RSSQSX$_7$VX$_8$SNGNTYLX$_9$, wherein X$_7$ is selected from L and I, X$_8$ is selected from H and R, and X$_9$ is selected from H and T (SEQ ID NO:24);
  a CDR2 having the amino acid sequence KVSNRFS (SEQ ID NO: 25); and
  a CDR3 having the amino acid sequence X$_{10}$QX$_{11}$X$_{12}$HVPPT, wherein X$_{10}$ is selected from S and F, X$_{11}$ is selected from S and G, and X$_{12}$ is selected from A and (SEQ ID NO:26).

In an embodiment such Ig-like molecule, antibody or antigen-binding fragment thereof comprises a heavy chain variable region comprising:
  a CDR1 having the amino acid sequence shown in SEQ ID NO:3;
  a CDR2 having the amino acid sequence shown in SEQ ID NO:4; and
  a CDR3 having the amino acid sequence shown in SEQ ID NO:5;
and a light chain variable region comprising:
  a CDR1 having the amino acid sequence shown in SEQ ID NO:6;
  a CDR2 having the amino acid sequence shown in SEQ ID NO:7; and
  a CDR3 having the amino acid sequence shown in SEQ ID NO:8.

In another embodiment, such Ig-like molecule, antibody or antigen-binding fragment thereof comprises a heavy chain variable region comprising:
  a CDR1 having the amino acid sequence shown in SEQ ID NO:9;
  a CDR2 having the amino acid sequence shown in SEQ ID NO:10; and
  a CDR3 having the amino acid sequence shown in SEQ ID NO:11;
and a light chain variable region comprising:
  a CDR1 having the amino acid sequence shown in SEQ ID NO:12;
  a CDR2 having the amino acid sequence shown in SEQ ID NO:13; and
  a CDR3 having the amino acid sequence shown in SEQ ID NO:14.

In yet another embodiment, the Ig-like molecule, antibody or antigen-binding fragment thereof comprises a heavy chain variable region comprising:
  a CDR1 having the amino acid sequence shown in SEQ ID NO:15;
  a CDR2 having the amino acid sequence shown in SEQ ID NO:16; and
  a CDR3 having the amino acid sequence shown in SEQ ID NO:17;
and a light chain variable region comprising:
  a CDR1 having the amino acid sequence shown in SEQ ID NO:18;
  a CDR2 having the amino acid sequence shown in SEQ ID NO:19; and
  a CDR3 having the amino acid sequence shown in SEQ ID NO:20.

In another aspect, an Ig-like molecule, antibodies or antigen-binding fragments thereof as taught herein specifically bind to the amino acid sequence LFPAP (SEQ ID NO:28). The present inventor found that Ig-like molecules or fragments thereof as taught herein bind with high affinity to the amino acid sequence as set forth in SEQ ID NO:28. The present inventor also found that Ig-like molecules taught herein resulted in increased survival after myocardial infarction.

The present invention also provides an Ig-like molecule, antibody or antigen-binding fragment thereof comprising a heavy chain variable region comprising a CDR1 having the amino acid sequence shown in SEQ ID NO:29 or an amino acid sequence as shown in SEQ ID NO:29, wherein at most 2, preferably at most 1 amino acid is substituted, a CDR2 having the amino acid sequence shown in SEQ ID NO:30 or an amino acid sequence as shown in SEQ ID NO:30, wherein at most 2, preferably at most 1 amino acid is substituted, and a CDR3 having the amino acid sequence SHY.

Additionally, the present invention provides an Ig-like molecule, antibody or antigen-binding fragment thereof comprising a light chain variable region comprising a CDR1 having the amino acid sequence shown in SEQ ID NO:31 or an amino acid sequence as shown in SEQ ID NO:31, wherein at most 2, preferably at most 1 amino acid is substituted, a CDR2 having the amino acid sequence shown in SEQ ID NO:32 or an amino acid sequence as shown in SEQ ID NO:32, wherein at most 2, preferably at most 1 amino acid is substituted, and a CDR3 having the amino acid sequence shown in SEQ ID NO:33 or an amino acid sequence as shown in SEQ ID NO:33, wherein at most 2, preferably at most 1 amino acid is substituted.

In an embodiment, the Ig-like molecule, antibody or antigen-binding fragment thereof comprises a heavy chain variable region comprising a CDR1 having the amino acid sequence shown in SEQ ID NO:29 or an amino acid sequence as shown in SEQ ID NO:29, wherein at most 2, preferably at most 1 amino acid is substituted, a CDR2 having the amino acid sequence shown in SEQ ID NO:30 or an amino acid sequence as shown in SEQ ID NO:30, wherein at most 2, preferably at most 1 amino acid is substituted, and a CDR3 having the amino acid sequence SHY, and further comprises a light chain variable region comprising a CDR1 having the amino acid sequence shown in SEQ ID NO:31 or an amino acid sequence as shown in SEQ ID NO:31, wherein at most 2, preferably at most 1 amino acid is substituted, a CDR2 having the amino acid sequence shown in SEQ ID NO:32 or an amino acid sequence as shown in SEQ ID NO:32, wherein at most 2, preferably at most 1 amino acid is substituted, and a CDR3 having the amino acid sequence shown in SEQ ID NO:33 or an amino acid sequence as shown in SEQ ID NO:33, wherein at most 2, preferably at most 1 amino acid is substituted.

In a suitable embodiment, additionally, the present invention provides an Ig-like molecule, antibody or antigen-binding fragment thereof comprising a light chain variable region comprising a CDR1 having the amino acid sequence shown in SEQ ID NO:31 or an amino acid sequence as shown in SEQ ID NO:31, wherein at most 2, preferably at most 1 amino acid is substituted, a CDR2 having the amino acid sequence shown in SEQ ID NO:32 or an amino acid sequence as shown in SEQ ID NO:32, wherein at most 2, preferably at most 1 amino acid is substituted, and a CDR3 having the amino acid sequence shown in SEQ ID NO:33 or an amino acid sequence as shown in SEQ ID NO:33, wherein at most 2, preferably at most 1 amino acid is substituted.

In an embodiment, the Ig-like molecule, antibody or antigen-binding fragment thereof comprises a heavy chain variable region comprising:
 a CDR1 having the amino acid sequence shown in SEQ ID NO:29;
 a CDR2 having the amino acid sequence shown in SEQ ID NO:30; and
 a CDR3 having the amino acid sequence SHY;
and/or a light chain variable region comprising:
 a CDR1 having the amino acid sequence shown in SEQ ID NO:31;
 a CDR2 having the amino acid sequence shown in SEQ ID NO:32; and
 a CDR3 having the amino acid sequence shown in SEQ ID NO:33.

The present inventor found that the Ig-like molecules, antibodies or antigen-binding fragments as taught herein were all particularly effective in increasing survival and improving cardiac function after myocardial infarction. Further, it was found that the Ig-like molecules, antibodies or antigen-binding fragments thereof as taught herein delay clearance of acellular matrix and do not affect proper scar formation, which is important to prevent dilatation and rupture of the heart after myocardial infarction.

Nucleic Acid Molecules, Vectors and Host Cells of the Invention

The present invention also relates to a (isolated) nucleic acid molecule encoding the Ig-like molecules, antibodies or antigen-binding fragments thereof as taught herein. In the present invention, the terms "nucleic acid molecule," or "polynucleotide molecule" are understood to refer to polymers of nucleotides of any length, and include DNA and RNA. The nucleotides can be deoxyribonucleotides, ribonucleotides, modified nucleotides or bases, and/or their analogues, or any substrate that can be incorporated into a polymer by DNA or RNA polymerase, or by a synthetic reaction. Methods and standard protocols for the preparation, synthesis, and production of nucleic acid molecules which are capable of encoding the Ig-like molecules, antibodies or antigen-binding fragments thereof as taught herein are well-known in the art through conventional molecular biology teachings.

In case the Ig-like molecule taught herein is an antibody comprising a light chain and a heavy chain, two nucleic acid molecules may be introduced into a host cell, i.e., one nucleic acid molecule encoding the amino acid sequence of the light chain and a second nucleic acid molecule encoding the amino acid sequence of the heavy chain. The invention may provide a set of nucleic acid molecules, said set comprising a first nucleic acid molecule encoding a light chain of an antibody, said light chain comprising a variable region and a constant region, and a second nucleic acid molecule encoding a heavy chain of an antibody, said heavy chain comprising a variable region and a constant region.

In one embodiment, the invention relates to a vector comprising the nucleic acid molecule(s) as taught herein, which is capable of encoding the Ig-like molecules, antibodies and antigen-binding fragments thereof as taught herein. The term "vector" is well-known in the art and is understood to refer to a nucleic acid molecule capable of artificially carrying or transporting foreign genetic material (i.e. nucleic acid molecule) to which it has been linked, into another cell, where it can be replicated and/or expressed. In an embodiment of the invention, certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, vectors may comprise promoters that are capable of directing the expression of genes to which they are operatively linked. Vectors may be "expression vectors". Other types of vectors include cosmids and artificial chromosomes. Methods and standard protocols for the preparation of suitable vectors comprising nucleic acid molecules which are capable of encoding the Ig-like molecules or fragments thereof as taught herein are also well known to the skilled person.

In an embodiment, the vector(s) is/are preferably (a) gene therapy vector(s).

The invention also relates to a host cell comprising and optionally expressing the nucleic acid molecule(s) or the vector(s) of the invention. Preferably, the host cell is a mammalian host cell. Mammalian host cells are well-known in the art and are commercially available. Non-limiting examples of mammalian host cells are Chinese hamster ovary (CHO) cells, NS0 murine myeloma cells, and PER.C6® human cells.

In a preferred embodiment, the mammalian host cell is a hybridoma. Methods and protocols to produce and maintain immortalized B cells in culture medium for the production of antibodies or Ig-like molecules or fragments thereof as taught herein are well-known in the art.

Pharmaceutical Compositions

The present invention also provides a pharmaceutical composition comprising an agent selected from the group consisting of (a) an Ig-like molecule, antibody or antigen-binding fragment thereof as taught herein, (b) a nucleic acid comprising a nucleic acid molecule encoding an Ig-like molecule, antibody or antigen-binding fragment thereof as taught herein, (c) a vector comprising the nucleic acid molecule encoding an Ig-like molecule, antibody, or antigen-binding fragment thereof as taught herein, and (d) a host cell expressing the nucleic acid of (b) or the vector of (c) as taught herein; and a pharmaceutically acceptable diluent or carrier.

In the present invention, the term "pharmaceutically acceptable" refers to those compositions or combinations of agents, materials, or compositions, and/or their dosage forms, which are within the scope of sound medical judgment, suitable for use in contact with the tissues of human beings and animals without excessive toxicity, irritation, allergic response, or other problem or complication, commensurate with a reasonable benefit/risk ratio. Furthermore, the term "pharmaceutically acceptable diluent or carrier" refers to a pharmaceutically acceptable material, composition or vehicle, such as a liquid or solid filler, diluent, excipient, solvent or encapsulating material, involved in carrying or transporting the subject chemical from one organ, or portion of the body, to another organ, or portion of the body. Other examples of materials widely used in medicine are stents, included but not limited to polymer-based or absorbable (i.e. biodegradable) stents. In the art, these stents are called drug-eluting stents. In the present invention, the stents are covered with or include the pharmaceutical composition in order to have the pharmaceutical composition released to the site of interest (e.g. coronary arteries in case of myocardial infarction, carotid artery or its distal branches in case of ischemic brain injury/stroke). Other non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The pharmaceutical composition may be administered by any suitable routes and mode. As will be appreciated by the person skilled in the art, the route and/or mode of administration will vary depending upon the desired results.

The pharmaceutical compositions according to the invention may be formulated in accordance with routine procedures for administration by any routes, such as parenteral, topical, oral, sublingual, transdermal, or by inhalation or via drug-eluting stents. The compositions may be in the form of tablets, capsules, powders, drug-eluting stents, granules, lozenges, creams or liquid preparations, such as sterile parenteral solutions or suspensions or in the form of a spray, aerosol or other conventional method for inhalation.

The pharmaceutical compositions of the present invention include those suitable for oral, nasal, topical (including buccal and sublingual), rectal, vaginal and/or parenteral administration.

In an embodiment, the pharmaceutical composition is administered parenterally.

The phrases "parenteral administration" and "administered parenterally" as used herein mean modes of administration other than enteral and topical administration, usually by injection, and include, without limitation, intravenous, intramuscular, intraarterial, intracoronary, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

In an embodiment the pharmaceutical composition is administered by intravenous injection or infusion.

Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical composition of the invention is contemplated. Preferably, the carrier is suitable for parenteral administration, e.g. intravenous injection or infusion.

Pharmaceutical compositions typically must be sterile and stable under the conditions of manufacture and storage. The composition can be formulated as a solution, micro-emulsion, liposome, or other ordered structure suitable to high drug concentration. Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Prolonged absorption of the injectable compositions can be brought about by including in the composition an agent that delays absorption, for example, monostearate salts and gelatin.

Sterile injectable solutions can be prepared by incorporating the Ig-like molecules, or antibodies, or antigen-binding fragments thereof as taught herein in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, the preferred methods of preparation are vacuum drying and freeze-drying (lyophilisation) that yield a powder of the active ingredient plus any additional desired ingredient from a previously sterile-filtered solution thereof.

Dosage regimens may be adjusted to provide the optimum desired therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, (b) the limitations inherent in the art of compounding such an active compound for the treatment of sensitivity in individuals, and (c) duration and level of expression of fibronectin-EDA in the related disease entity. For example, fibronectin-EDA expression reaches a peak at 2 to 3 weeks and reduces to baseline levels 5 to 6 weeks after acute myocardial infarction. Depending on the half-life of the anti-fibronectin-EDA compound (e.g. the Ig-like molecules, antibodies or antigen-binding fragment thereof as taught herein), the compound will be administered once, twice, three times or more frequent if desired to cover the entire expression duration of fibronectin-EDA.

Actual dosage levels of the Ig-like molecules or antibodies or antigen-binding fragments thereof as taught herein in the pharmaceutical compositions of the present invention may be varied so as to obtain an amount of Ig-like molecules or antibodies or antigen-binding fragments thereof which is effective ("effective amount") to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion, the duration of the treatment, other drugs, compounds and/or materials used in combination with the particular compositions employed, the age, sex, weight, condition, general health and prior medical history of the patient being treated, and like factors well known in the medical arts.

Methods and Uses of the Invention

The present invention also relates to a method for improving the intrinsic angiogenic response in fibronectin-EDA-mediated wound healing after ischemic injury. Such method comprises administering to a subject in need thereof a therapeutically effective amount of antibody that binds fibronectin-EDA or an antigen-binding fragment thereof. Further provided is an antibody that binds fibronectin-EDA or an antigen-binding fragment thereof for use in stimulating angiogenesis. As demonstrated in the Example 5, the present inventor found that treatment with anti-fibronectin-EDA antibodies after myocardial infarction increases blood vessel formation in the heart, in particular in both the infarcted area of the heart and in the border zone of infarcted and unaffected area of the heart. Further, an in vitro spouting assay shows that fibronectin-EDA is capable of inhibiting sprouting of endothelial cells. These findings collectively indicate that fibronectin-EDA inhibits angiogenesis in the infarcted heart. Without wishing to be bound by theory, it is believed that fibronectin-EDA inhibits endothelial cell sprouting by binding to al integrins on these cells and that the increase in vessel formation caused by anti-fibronectin-EDA antibodies is due to the prevention of this inhibition. Hence, the present inventor found that anti-fibronectin-EDA antibodies can be used to prevent the inhibitory effects of fibronectin-EDA on angiogenesis after tissue injury. This is in particular surprising since the use of anti-fibronectin-EDA antibodies as anti-tumour agents is currently considered. Fibronectin-EDA is found to be highly upregulated around tumour vasculature and in contrast to the findings of the present inventor, fibronectin-EDA is thought to associate with angiogenesis in tumours.

In addition to the heart following myocardial infarction, fibronectin-EDA can be upregulated in other ischemic tissue, where improvement of the angiogenic response generally has a beneficial effect after ischemic injury.

Provided is therefore a method for improving angiogenesis in a subject in need thereof, comprising administering to said subject a therapeutically effective amount of an antibody that binds fibronectin-EDA or an antigen-binding fragment thereof. Also provided is an antibody that binds fibronectin-EDA or an antigen-binding fragment thereof for use in improving angiogenesis. Angiogenesis is preferably improved in fibronectin-EDA-mediated wound healing after ischemic injury.

As used herein the term "improving angiogenesis" indicates that there is an increase in the level of angiogenesis in tissue, preferably after injury, following administration of an antibody that binds fibronectin-EDA according to the invention as compared the level of angiogenesis in said tissue, preferably after injury, wherein fibronectin-EDA is expressed but wherein an antibody that binds fibronectin-EDA according to the invention is absent. Hence, such antibody according to the invention induces angiogenesis as compared to a situation wherein said antibody is absent, but preferably wherein fibronectin-EDA is expressed. Preferably, angiogenesis is improved in tissue following injury, such as in ischemic tissue, wounds, fibrotic tissue and/or upon organ or tissue transplantation. Preferably, angiogenesis is improved in a subject suffering from ischemic disease, in particular from cardiac ischemia, peripheral ischemia and/or peripheral arterial disease, in fibrotic disease, in pressure-overload conditions, in wounds and/or upon organ or tissue transplantation, most preferably in a subject suffering from ischemic disease. Angiogenesis is preferably improved in ischemic tissue, such as cardiac ischemic tissue or peripheral ischemic tissue, in fibrotic tissue, in pressure-overload conditions, in wound tissue and/or upon organ or tissue transplantation. Most preferably angiogenesis is improved in ischemic tissue. The term "ischemic disease" as used herein refers to diseases whereby one or more organs or tissues are affected by ischemia. Examples of ischemic diseases are cardiac ischemia, peripheral ischemia, and peripheral arterial disease. Examples of cardiac ischemia or causes thereof include, but are not limited to, myocardial infarction, mitral valve disease, chronic atrial fibrillation and cardiomyopathies in which thrombi are prone to develop. "Peripheral ischemia" as used herein refers to a condition of decreased blood supply to one or more limbs, which may be connected to peripheral arterial disease. Examples of causes of peripheral ischemia include embolism, thrombosis, dissection, venous occlusion, atherosclerosis, aneurysm and trauma. "Pressure-overload conditions" is a term well known in the art and relates to Preferred but non-limiting examples of pressure-overload conditions are hypertension, valvular disease and non-ischemic cardiomyopathy.

In a preferred embodiment, an Ig-like molecule or antigen-binding fragment thereof according to the present invention is used for stimulating angiogenesis as described herein. Hence, provided is an isolated immunoglobulin (Ig)-like molecule or antigen-binding fragment thereof specifically binding to an amino acid sequence as set forth in SEQ ID NO:1, SEQ ID NO:2 or SEQ ID NO:28 for use in stimulating angiogenesis. Preferably an Ig-like molecule, antibody or antigen-binding fragment thereof selected from the group consisting of:

Ig-like molecule, antibody or antigen-binding fragment thereof comprising a heavy chain variable region comprising a CDR1 having the amino acid sequence shown in SEQ ID NO:3; a CDR2 having the amino acid sequence shown in SEQ ID NO:4; and a CDR3 having the amino acid sequence shown in SEQ ID NO:5; and a light chain variable region comprising a CDR1 having the amino acid sequence shown in SEQ ID NO:6; a CDR2 having the amino acid sequence shown in SEQ ID NO:7; and a CDR3 having the amino acid sequence shown in SEQ ID NO:8;

an Ig-like molecule, antibody or antigen-binding fragment thereof comprising a heavy chain variable region comprising a CDR1 having the amino acid sequence shown in SEQ ID NO:9; a CDR2 having the amino acid sequence shown in SEQ ID NO:10; and a CDR3 having the amino acid sequence shown in SEQ ID NO:11; and a light chain variable region comprising a CDR1 having the amino acid sequence shown in SEQ ID NO:12; a CDR2 having the amino acid sequence shown in SEQ ID NO:13; and a CDR3 having the amino acid sequence shown in SEQ ID NO:14;

Ig-like molecule, antibody or antigen-binding fragment thereof comprising a heavy chain variable region comprising a CDR1 having the amino acid sequence shown in SEQ ID NO:15; a CDR2 having the amino acid sequence shown in SEQ ID NO:16; and a CDR3 having the amino acid sequence shown in SEQ ID NO:17; and a light chain variable region comprising a CDR1 having the amino acid sequence shown in SEQ ID NO:18; a CDR2 having the amino acid sequence shown in SEQ ID NO:19; and a CDR3 having the amino acid sequence shown in SEQ ID NO:20;

Ig-like molecule or antigen-binding fragment thereof according to claim 10 comprising a heavy chain variable region comprising a CDR1 having the amino acid sequence shown in SEQ ID NO:29; a CDR2 having the amino acid sequence shown in SEQ ID NO:30; and a CDR3 having the amino acid sequence SHY; and/or a light chain variable region comprising a CDR1 having the amino acid sequence shown in SEQ ID NO:31; a CDR2 having the amino acid sequence shown in SEQ ID NO:32; and a CDR3 having the amino acid sequence shown in SEQ ID NO:33;

is used for improving angiogenesis, preferably for improving angiogenesis is a subject suffering from ischemic disease, in fibrotic disease, in pressure-overload conditions, in wounds and/or upon organ or tissue transplantation. More preferably such Ig-like molecule, antibody or antigen-binding fragment thereof is used from improving angiogenesis in ischemic tissue, such as cardiac ischemic tissue or peripheral ischemic tissue, in fibrotic tissue, in pressure-overload conditions, in wound tissue and/or upon organ or tissue transplantation, most preferably in ischemic tissue. Preferably such antibody is a humanized antibody, preferably a humanized stabilized IgG4 antibody as described herein.

Further provided is a method for improving angiogenesis in a subject in need thereof, comprising administering to said subject a therapeutically effective amount of a therapeutically effective amount of an agent selected from the group consisting of (a) an Ig-like molecule, antibody or antigen-binding fragment thereof as taught herein, (b) a nucleic acid comprising (a) nucleic acid molecule(s) encoding an Ig-like molecule, antibody or antigen-binding fragment thereof as taught herein, (c) one or more vector(s) comprising the nucleic acid molecule(s) as taught herein and (d) a host cell expressing the nucleic acid molecule(s) as taught herein.

Also provided is an agent selected from the group consisting of (a) an Ig-like molecule, antibody or antigen-binding fragment thereof as taught herein, (b) a nucleic acid comprising (a) nucleic acid molecule(s) encoding an Ig-like molecule, antibody or antigen-binding fragment thereof as taught herein, (c) one or more vector(s) comprising the nucleic acid molecule(s) as taught herein and (d) a host cell expressing the nucleic acid molecule(s) as taught herein for use in improving angiogenesis in a subject in need thereof.

The present invention further provides an antibody that binds fibronectin-EDA or an antigen-binding fragment thereof for use in stimulating angiogenesis as described herein and a method for stimulating angiogenesis comprising administering to a subject in need thereof a therapeutically effective amount of an antibody that binds fibronectin-EDA or an antigen-binding fragment thereof.

The present invention also relates to a method of treating, preventing or preventing progression of adverse cardiac and vascular remodelling and myocardial infarction- and pressure-overload-related complications. Such method as taught herein comprises administering to a subject in need thereof, a therapeutically effective amount of an agent selected from the group consisting of (a) an Ig-like molecule, antibody or antigen-binding fragment thereof as taught herein, (b) a nucleic acid comprising (a) nucleic acid molecule(s) encoding an Ig-like molecule, antibody or antigen-binding fragment thereof as taught herein, (c) one or more vector(s) comprising the nucleic acid molecule(s) as taught herein and (d) a host cell expressing the nucleic acid molecule(s) as taught herein. As used herein, the term "effective amount" refers to a quantity sufficient to achieve a desired therapeutic and/or prophylactic effect, e.g., an amount which results in the treatment, prevention of, or prevention of progression of adverse cardiac remodelling and/or a disease or condition associated with, related to or resulting from myocardial infarction and/or pressure-overload, such as heart failure or one or more symptoms associated with heart failure.

The Ig-like molecules, antibodies or antigen-binding fragments as taught herein may be administered to a subject having one or more signs or symptoms of myocardial infarction and/or heart failure, such as chest pain, dyspnea, edema and cardiomegaly. For example, a "therapeutically effective amount" of the Ig-like molecules, antibodies or antigen-binding fragments as taught herein refers to levels in which the physiological effects of a disease or condition associated with, related to or resulting from myocardial infarction, pressure-overload and/or adverse cardiac remodelling, such as heart failure are, at a minimum, ameliorated. The skilled person will be capable of determining when such disease or condition has been treated, prevented, or when its progression has been prevented.

In an embodiment, an effective amount of the Ig-like molecule, antibody, or antigen-binding fragment thereof as taught herein, such as a monoclonal antibody, may be in the range of about 0.1 µg/kg to about 10 g/kg, such as about 1 µg/kg to about 1 g/kg, about 10 µg/kg to about 100 mg/kg, or about 0.1 mg/kg to about 50 mg/kg.

The Ig-like molecules, antibodies or antigen-binding fragments thereof as taught herein may be administered once in a single dosage, or may be administered several times after myocardial infarction. For example, Ig-like molecules, antibodies or antigen-binding fragments thereof as taught herein may be administered intravenously, once immediately after the myocardial infarction (i.e., within 48 hours of the myocardial infarction), followed by one or more intravenous administrations on the days following the first administration of the binding member of the invention. The Ig-like molecules, antibodies or antigen-binding fragments thereof as taught herein may be administered with an interval ranging from about 2 hours to about 14 days, such as about 4 hours to about 10 days, about 6 hours to about 8 days, about 8 hours to about 6 days, about 12 hours to about 4 days, or about 24 hours to about 2 days to achieve optimal therapeutic or preventive effect.

In one embodiment, therapeutic benefits are observed following treatment of subjects according to the method as taught herein. For instance, therapeutic benefits may be exemplified by observing: 1) prevention of the progression of myocardial infarct- and pressure-overload-related conditions and adverse cardiac remodelling in a subject, and/or 2) decreased or lower levels of complications relating to or resulting from myocardial infarction, pressure-overload and adverse cardiac remodelling in a subject, and/or 3) lower risk of developing or suffering from complications relating to or resulting from myocardial infarction, pressure-overload and adverse cardiac remodelling in a subject, and/or 4) halted the progression of myocardial infarct- and pressure-overload-related conditions and adverse cardiac remodelling in a subject, and/or 5) increased survival following myocardial infarction, pressure-overload and adverse cardiac remodelling in a subject.

In the present invention, disease conditions relating to or resulting from myocardial infarction, pressure-overload and adverse cardiac remodelling include conditions or diseases such as heart failure; remote myocardial fibrosis; aneurysm or rupture of the ventricle; mitral regurgitation, particularly if the infarction is large and likely to cause severe ventricular dilatation; and arrhythmias, such as ventricular fibrillation and ventricular tachycardia due to the ventricular enlargement, reactive and/or replacement (scar) fibrosis.

In one embodiment of the invention, the Ig-like molecules, antibodies or fragments thereof and method using them as taught herein are particularly suitable for the treatment, prevention or prevention of the progression of myocardial infarct- and pressure-overload-related conditions (e.g. heart failure; remote myocardial fibrosis; aneurysm or rupture of the ventricle; mitral regurgitation, particularly if the infarction is large and likely to cause severe ventricular dilatation; and arrhythmias, such as ventricular fibrillation and ventricular tachycardia due to the ventricular enlargement, reactive and replacement (scar) fibrosis).

The Ig-like molecules, antibodies or fragments thereof may also be suitable for the treatment, prevention or prevention of the progression of adverse tissue remodelling, such as fibrosis and reduced cardiac function that result from hypertension and/or aortic valve stenosis; allograft rejection that results after heart transplantation; pulmonary hypertension and lung dysfunction that result from lung fibrosis, joint dysfunction that results from rheumatoid arthritis and/or osteoarthritis, seizures, paralysis and/or paresis, and infarction of the brain that result from an ischemic stroke.

In one embodiment of the invention, other therapeutic benefits may be exemplified by observing: 1) reduced heart failure, or reduced fibrosis or reduced risk for arrhythmias in a subject suffering from hypertension and/or aortic stenosis, and/or 2) improved cardiac function, or reduced fibrosis, or reduced risk for arrhythmias in a subject suffering from allograft rejection after heart transplantation, and/or 3) reduced infarct size, or less severe paralysis and/or paresis, or improved neurological condition in a subject suffering from ischemic stroke, and/or 4) reduced risk for developing lung fibrosis in a subject exposed to certain drugs (amiodarone, bleomycin, methotrexate, nitrofurantoin, busulfan), or radiation, or sarcoidosis or other connective tissue diseases, and/or 5) reduced pain or improved joint function in a subject suffering from osteo- or rheumatoid arthritis, and/or 6) reduced metastasis, or improved local function, or improved survival in a subject suffering from cancer.

In the present invention, the term "heart failure" is understood to refer to any condition characterized by decreased cardiac output and/or abnormal filling pressures in the ventricles. In these situation, the hearth is unable to pump blood at an adequate rate or in an adequate volume and/or in adequate force (i.e. systolic heart failure) or exhibits increased ventricular stiffness and/or disturbed ventricular relaxation (i.e. diastolic heart failure). In heart failure, blood perfusion of organs is hampered thereby deteriorating organ function (e.g. kidneys or liver failure). In addition, blood can back up into the lungs, causing the lungs to become congested with fluid. Typical symptoms of heart failure include shortness of breath (dyspnea), fatigue, weakness, difficulties breathing when lying flat, and swelling of the legs, ankles or abdomen (edema).

In the present invention, the terms "treating", "preventing", or "preventing progression of" are understood to not only encompasses the onset of adverse cardiac remodelling, but also encompasses the situation in which adverse cardiac remodelling has commenced but is halted from continuing further. Thus, it encompasses the situation in which full-blown development of myocardial infarction- and/or pressure-overload-related complications is prevented, even if such myocardial infarction- and/or pressure-overload-related complications have already started to develop. For example, cardiac dilatation that has already commenced can be stopped by the therapeutic intervention using the Ig-like molecules, or antibodies or antigen-binding fragment thereof as taught herein. Such method is encompassed by the present invention. As adverse remodelling is reversible, adverse remodelling-related complications, herein also referred to as "myocardial infarction and/or pressure-overload-related complications", can also be treated using the method of the present invention.

In the present invention, the term "subject" is understood to refer to any vertebrate animal, but will typically pertain to a mammal, for example a human patient, a domesticated animal (such as dog or cat), a farm animal (such as horse, cow, or sheep) or a laboratory animal (such as rat, mouse, non-human primate or guinea pig). In certain examples, the subject is human.

In one embodiment, the subject is selected from the group consisting of horse, dog and human. In another embodiment of the invention, the Ig-like molecules, or antibodies or fragment thereof as taught herein, the pharmaceutical composition as taught herein, and the method of the invention as taught herein may be used to prevent or treat complications related to myocardial infarction, pressure-overload and adverse cardiac remodelling and/or to increase survival or decrease mortality following myocardial infarction, pressure-overload and adverse cardiac remodelling in dogs and horses, particularly racing dogs and horses.

In a preferred embodiment, the subject is human, particularly a human subject at risk of developing adverse cardiac remodelling and/or a human subject having suffered a myocardial infarction, pressure-overload and adverse cardiac remodelling and/or a human subject suffering from complications related to myocardial infarction, pressure-overload and adverse cardiac remodelling. In another embodiment, the human subject is at risk of suffering or developing fibronectin-EDA-mediated adverse tissue remodelling in the lungs (e.g. dyspnea, pulmonary hypertension and lung dysfunction that result from lung fibrosis), in joints (e.g. joint dysfunction that results from rheumatoid and/or osteoarthritis), in the brain (e.g. seizures, paralysis and/or paresis, and infarction of the brain that result from an ischemic stroke). The present inventor found that the Ig-like molecules, antibodies or antigen-binding fragments thereof as taught herein increased survival and improved cardiac function following myocardial infarction and pressure overload, presumably by preventing, treating and/or preventing progression of adverse cardiac remodelling in a subject.

Methods of carrying out the conventional techniques used in the present invention will be evident to the skilled person. The practice of conventional techniques in molecular biology, biochemistry, computational chemistry, cell culture, recombinant DNA, bioinformatics, genomics, sequencing and related fields are well-known to those of skill in the art and are discussed, for example, in the following literature references: Sambrook et al., Molecular Cloning. A Laboratory Manual, 2nd Edition, Cold Spring Harbor Laboratory Press, Cold Spring Harbor, N.Y., 1989; Ausubel et al., Current Protocols in Molecular Biology, John Wiley & Sons, New York, 1987 and periodic updates; and the series Methods in Enzymology, Academic Press, San Diego.

In this document and in its claims, the verb "to comprise" and its conjugations is used in its non-limiting sense to mean that items following the word are included, but items not specifically mentioned are not excluded. In addition, the verb "to consist" may be replaced by "to consist essentially of" meaning that a composition of the invention may comprise additional component(s) than the ones specifically identified, said additional component(s) not altering the unique characteristics of the invention.

The term "and/or" as used herein refers to a situation wherein one or more of the stated cases may occur, alone or in combination with at least one of the stated cases, up to with all of the stated cases.

The term "at least" refers to a situation wherein a particular value is the same as said particular value or more. For example, "at least 2" is understood to be the same as "2 or more" i.e., 2, 3, 4, 5, 6, 7, 8, 9, 10, 11, 12, 13, 14, 15, . . . , etc.

The indefinite article "a" or "an" thus usually means "at least one". It is further understood that, when referring to "sequences" herein, generally the actual physical molecules with a certain sequence of subunits (e.g. amino acids) are referred to.

FIGURES

Figure 1:
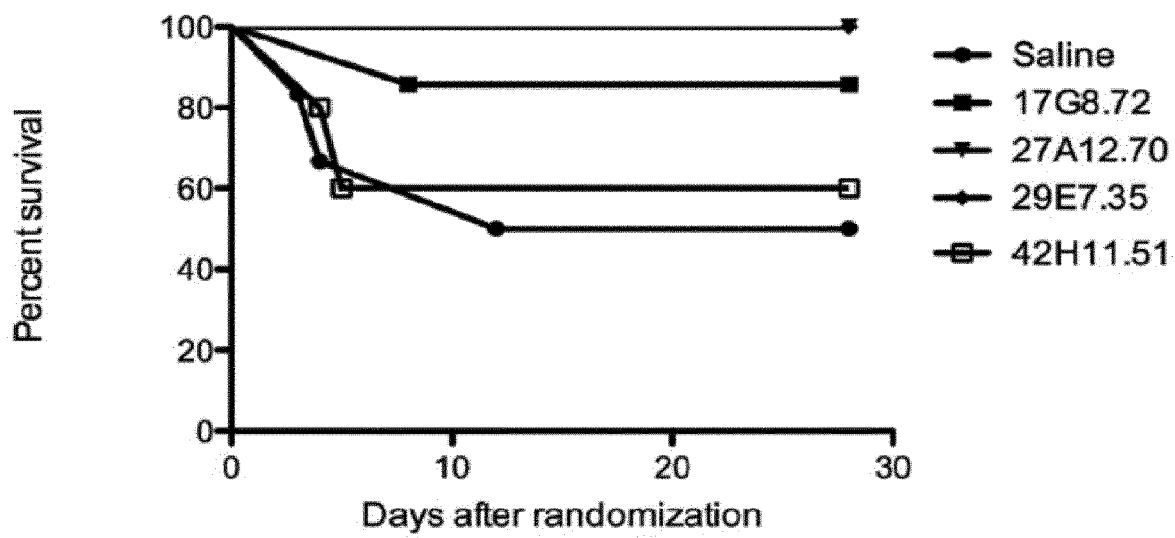
FIG. 1 depicts the percentage of survival following myocardial infarction observed over a period of 30 days for mice treated with various antibodies directed against the EDA domain of the fibronectin-EDA (i.e. 17G8.72, 27A12.70, 29E7.35, and 42H11.51) relative to mice treated with saline.

FIGS. 5A-5D: Improved cardiac function after MI with anti-EDA treatment. MRI images of A) a saline treated and B) an anti-EDA treated mouse heart. C) End-diastolic volume (EDV) increase after MI. Anti-EDA treatment shows attenuated increase in EDV compared to saline *$p=0.011$ and # $p=0.014$ and isotype control treated animals. D) End-systolic volume (ESV) increase after MI. compared to saline *$p=0.011$ and #$p=0.014$ isotype treated animals; $n=14$ in saline, $n=9$ in anti-EDA treated animals and $n=5$ in isotype control treated animals.

FIGS. 6A-6E: Anti-EDA treatment reduces blood leukocyte levels after 7 days of MI. A) Ly-6G+ neutrophils were significantly reduced in the anti-EDA treated group compared to control treated animals. B) CD3+ T-cells were non-significantly reduced after anti-EDA treatment. C) Ly-6C+/Ly-6G-monocytes and D) Ly-6C-/Ly-6G-monocytes were non-significantly reduced after anti-EDA treatment. E) CD49d expression was significantly increased on Ly-6C-/Ly-6G-monocytes after anti-EDA treatment. $N=8$ in control group, $N=5$ in anti-EDA group. Data is expressed as mean±SEM.

FIGS. 7A-7E: Inflammatory cytokines are decreased in the infarct area; however this does not affect leukocyte numbers. A) The pro-inflammatory cytokines IL-1b ($p=0.03$), GM-CSF ($p=0.04$), TNF-α ($p=ns$), MIP-1b ($p=ns$), RANTES ($p=0.01$), IL-4 ($p=0.02$) are decreased in the infarcted area of anti-EDA treated animals. The anti-inflammatory cytokine IL-10 is decreased ($p=ns$) and IL-17 is increased ($p=0.03$) in the infarcted area of anti-EDA treated animals. P values are not corrected for multiple testing. B) Example of Ly-6G neutrophil staining in the infarcted area. C) Quantification of neutrophil staining D) Example of Mac-3 macrophage staining in the infarcted area. E) Quantification of neutrophil staining $N=8$ in control group, $N=5$ in anti-EDA group. Data is expressed as mean±SEM.

FIGS. 8A-8D: Scar formation is not affected by anti-EDA treatment. A) Example of polarized light picture of picrosirius red staining in the infarcted area. B) Quantification of picrosirius red staining C) Quantification of mRNA levels of Col1 in the infarcted area. D) Quantification of mRNA levels of Col3 in the infarcted area. N=8 in control group, N=5 in anti-EDA group. Data is expressed as mean±SEM.

FIGS. 9A-9I: Anti-EDA treatment increases small vessel formation in border and infarct zone. A) CD31 vessel staining in the border zone of a control heart. B) CD31 vessel staining in the border zone of an anti-EDA treated heart. C) Quantification of total vessels in the border zone. There is an increase in total vessel number in the anti-EDA treated group (p<0.0001) D) Vessels are subdivided in classes based on diameter. The increase in total vessel number in the anti-EDA treated group is mainly due to an increase in small vessels 5-10 µm (p<0.0001) E) Quantification of total vessels in the infarct zone. There is an increase in total vessel number in the anti-EDA treated group (p=0.05). F) Vessels are subdivided in classes based on diameter. The increase in total vessel number in the anti-EDA treated group is mainly due to an increase in small vessels 10-16 um (p=0.01) G) Example of a positive control of sprouting assay H) Example of EDA inhibition in sprouting assay. I) Quantification of relative sprouting. Negative control is set to 1. N=8 in control group, N=5 in anti-EDA group. Data is expressed as mean±SEM.

FIGS. 10A-10H: There is a delayed clearance of acellular matrix upon anti-EDA treatment. A) Representative image of acellular matrix in control animal after 7 days of MI. B) Representative image of acellular matrix in anti-EDA treatment animal after 7 days of MI. C) Quantification of acellular matrix. There is more acellular matrix present in the anti-EDA treated group. (p<0.05) D) Zymogram showing MMP2 activity in heart tissue from control and anti-EDA treated animals. E) Quantification of total MMP2 activity. There is a decrease in MMP2 activity in the anti-EDA treated animals. F) Quantification of different MMP2 forms. There is a decrease in all different MMP2 forms in the anti-EDA treated animals. G) Quantification of periostin staining in the infarct area of control and anti-EDA treated animals. There is a decrease in periostin staining in the anti-EDA treated group. H) Quantification of fibroblast adhesion assay. Fibroblast adhere more to EDA-his fragment coating compared to III4-his fragment coating or no coating. This adhesion to EDA-his fragments can be inhibited by the anti-EDA antibody and not by isotype control. N=1. N=8 in control group, N=5 in anti-EDA group. Data is expressed as mean±SEM.

Figure 11:
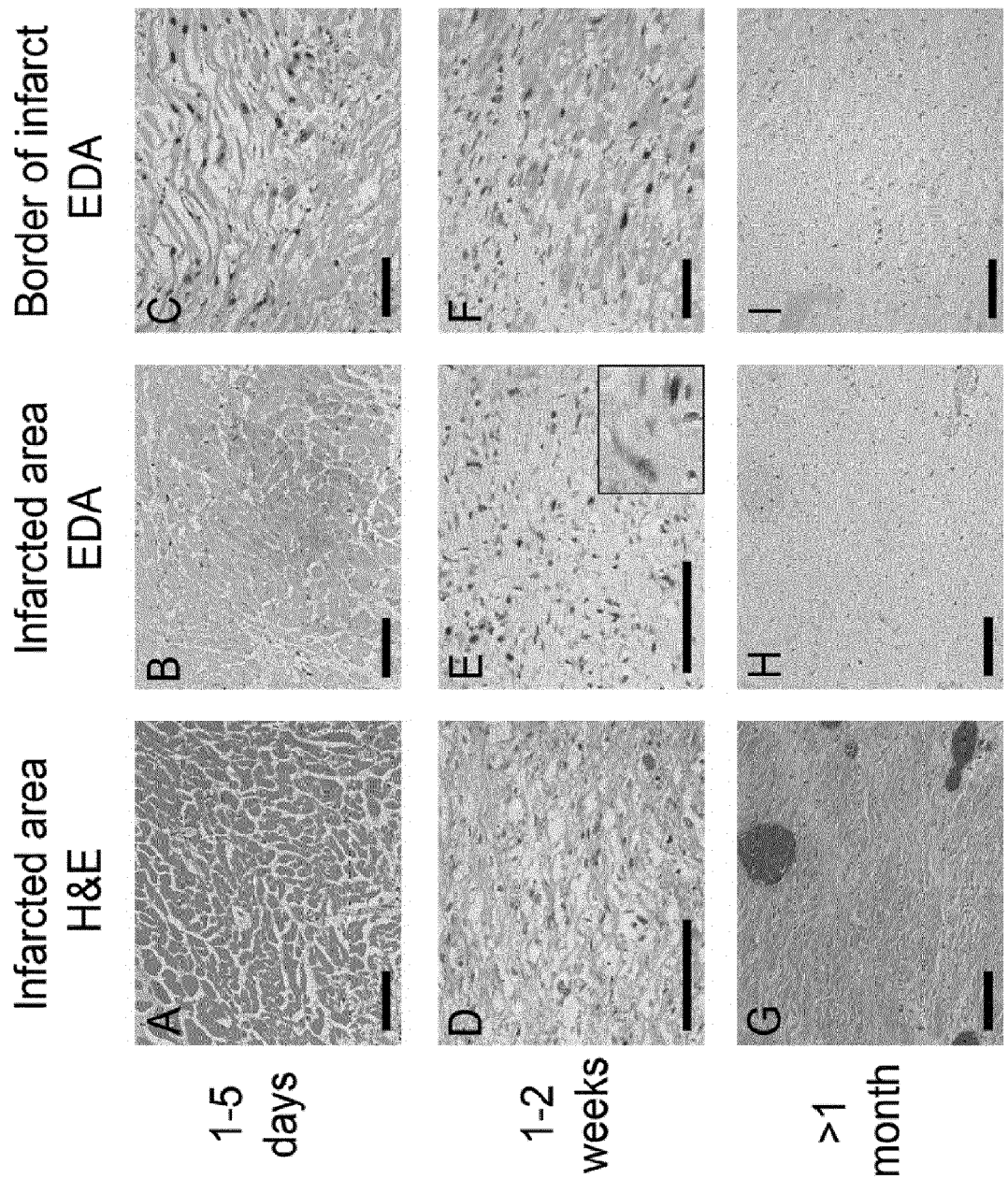

FIG. 11: EDA immunohistochemical staining in infarcted human myocardium. A) Myocardial infarction with coagulation necrosis of cardiomyocytes and infiltration of some neutrophil granulocytes. B) EDA immunostain of necrotic myocardium showing weak red staining in the infarcted area. C) EDA immunostain at the border of the infarcted area showing cytoplasmatic and nuclear staining (in red) in cardiomyocytes surrounding the infarct. D) Young granulation tissue with numerous fibroblasts. E) EDA immunostain showing strong cellular staining of fibroblasts. Inlay higher magnification of the EDA positive fibroblasts. F) EDA immunostain of myocardium surrounding the granulation tissue with weak cytoplasmatic and strong nuclear staining of part of the surrounding cardiomyocytes. G) Scar tissue with collagenous connective tissue with some fibroblasts. H) and I) Absent EDA immunostaining of the scar and surrounding myocardium. All bars are 100 µm. Representative pictures of 3 patients per time point; H&E=Hematoxylin and eosin staining.

Figure 12A:
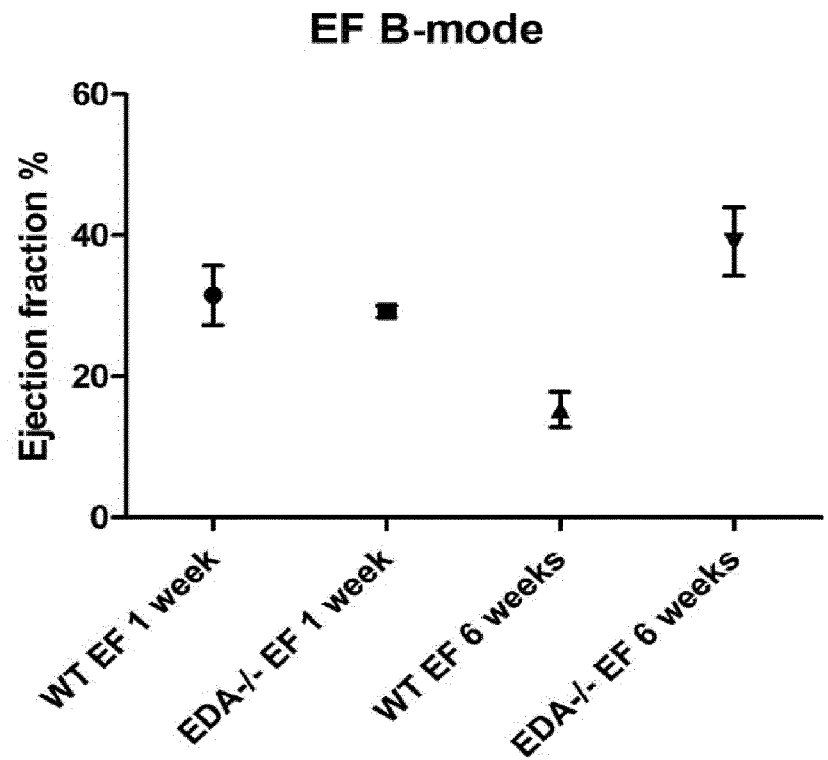
Figure 12B:
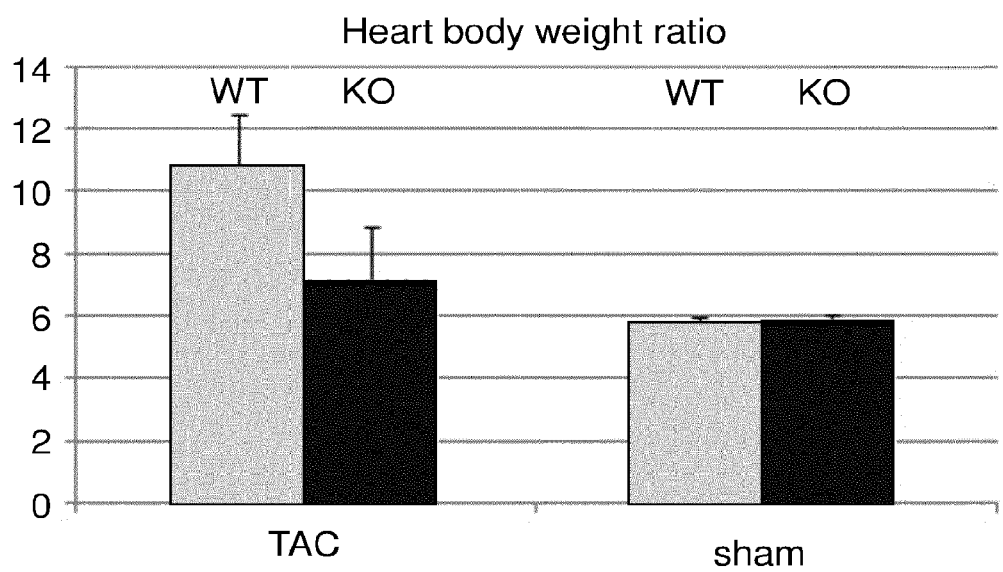

FIGS. 12A-12B. A) Ejection fraction (EF) and B) heart/body weight ratio 6 weeks after pressure-overload induced by transaortic constriction (TAC) in mice. Differences between EDA-deficient (KO; EDA-/-) and wild-type (WT) mice are at p<0.05 level. (EDA-deficient mice are described in Arslan F. et al. Circ. Res., March 2011; 108: 582-592 and WO2012/057613, Transaortic constriction (TAC) in the mouse is a commonly used experimental model for pressure overload-induced cardiac hypertrophy and heart failure).

SEQUENCES

```
SEQ ID NO: 1: Amino acid sequence of the epitope GIXXXF

SEQ ID NO: 2: Amino acid sequence of the epitope GIHELF

SEQ ID NO: 3: CDR1 of heavy chain variable region (antibody 27A12.70)
GYSITSGYSWH SEQ ID NO: 4: CDR2 of heavy chain variable region (antibody 27A12.70)
YIHYSGIANYNPSLKS SEQ ID NO: 5: CDR3 of heavy chain variable region (antibody 27A12.70)
EKTGFFDY SEQ ID NO: 6: CDR1 of light chain variable region (antibody 27A12.70)
RSSQSLVHSNGNTYLH SEQ ID NO: 7: CDR2 of light chain variable region (antibody 27A12.70)
KVSNRFS SEQ ID NO: 8: CDR3 of light chain variable region (antibody 27A12.70)
SQSAHVPPT SEQ ID NO: 9: CDR1 of heavy chain variable region (antibody 29E7.35)
GYSITSGYSWH SEQ ID NO: 10: CDR2 of heavy chain variable region (antibody 29E7.35)
YIHYSGSANYNPSLKS SEQ ID NO: 11: CDR3 of heavy chain variable region (antibody 29E7.35)
EKTGFFDY
```

-continued

SEQ ID NO: 12: CDR1 of light chain variable region (antibody 29E7.35)
RSSQSLVHSNGNTYLH SEQ ID NO: 13: CDR2 of light chain variable region (antibody 29E7.35)
KVSNRFS SEQ ID NO: 14: CDR3 of light chain variable region (antibody 29E7.35)
SQSAHVPPT SEQ ID NO: 15: CDR1 of heavy chain variable region (antibody 17G8.7VL)
GYSIASGYSWH SEQ ID NO: 16: CDR2 of heavy chain variable region (antibody 17G8.7VL)
YIHFSGSANYNPSLKS SEQ ID NO: 17: CDR3 of heavy chain variable region (antibody 17G8.7VL)
EARGYFDY SEQ ID NO: 18: CDR1 of light chain variable region (antibody 17G8.7VL)
RSSQSIVRSNGNTYLT SEQ ID NO: 19: CDR2 of light chain variable region (antibody 17G8.7VL)
KVSNRFS SEQ ID NO: 20: CDR3 of light chain variable region (antibody 17G8.7VL)
FQGSHVPPT SEQ ID NO: 21: CDR1 of the heavy chain variable region (consensus)
GYSIX$_1$SGYSWH
X$_1$ = T or A SEQ ID NO: 22: CDR2 of the heavy chain variable region (consensus)
YIHX$_2$SGX$_3$ANYNPSLKS
X$_2$ = Y or F; and X$_3$ = S or I SEQ ID NO: 23: CDR3 of the heavy chain variable region (consensus)
EX$_4$X$_5$GX$_6$FDY
X$_4$ = K or A; and X$_5$ = T or R; and X$_6$ = F or Y SEQ ID NO: 24: CDR1 of the light chain variable region (consensus)
RSSQSX$_7$VX$_8$SNGNTYLX$_9$
X$_7$ = L or I; and X$_8$ = H or R; and X$_9$ = H or T SEQ ID NO: 25: CDR2 of the light chain variable region (consensus)
KVSNRFS SEQ ID NO: 26: CDR3 of the light chain variable region (consensus)
X$_{10}$QX$_{11}$X$_{12}$HVPPT
X$_{10}$ = S or F; and X$_{11}$ = S or G; and X$_{12}$ = A or S SEQ ID NO: 27 (immunizing peptide)
TYSSPEDGIHELFPAPDGEEDTAELQGGC SEQ ID NO: 28: Amino acid sequence of the epitope on the EDA domain of fibronectin-EDA for antibody 33E3.10)
LFPAP SEQ ID NO: 29: CDR1 of heavy chain variable region (antibody 33E3.10)
GFTFSNSAMT SEQ ID NO: 30: CDR2 of heavy chain variable region (antibody 33E3.10)
SISGGGTTYYPDSVKG CDR3 of heavy chain variable region (antibody 33E3.10)
SHY SEQ ID NO: 31: CDR1 of light chain variable region (antibody 33E3.10)
KASQNVVTNVA SEQ ID NO: 32 CDR2 of light chain variable region (antibody 33E3.10)
SASYRYS SEQ ID NO: 33: CDR3 of light chain variable region (antibody 33E3.10)
QQYNSYPYT SEQ ID NO: 34: Humanized heavy chain of antibody 27A12.70
QVQLQESGPGLVKPSQTLSLTCTVSGYSITSGYSWHWIRQHPGKKLEWMGYIHYSGIANYNPSLKSRITISRDTSKNQFSLKL
SSVTAADTAVYYCATEKTGFFDYWGQGTLVTVSSASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKRVESKYGPPCPPCPAPEAAGGPSVFLFPPKPKDTLM ISRTPEVTCVVVDVSQEDPEVQFNWYVDGVEVHNAKTKPREEQFNSTYRVVSVLTVLHQDWLNGKEYKCKVSNKGLPSSIEKT ISKAKGQPREPQVYTLPPSQEEMTKNQVSLTCLVKGFYPSDIAVEWESNGQPENNYKTTPPVLDSDGSFFLYSRLTVDKSRWQ

EGNVFSCSVMHEALHNHYTQKSLSLSLGK

SEQ ID NO: 35: Humanized light chain of antibody 27A12.70
DVVMTQTPLSLSVTPGQPASISCRSSQSLVHSNGNTYLHWYLQKPGQSPQLLIYKVSNRFSGVPDRFSGSGSGTDFTLKISRV EAEDVGVYYCSQSAHVPPTFGGGTKVEIKRTVAAPSVFIFPPSDEQLKSGTASVVCLLNNFYPREAKVQWKVDNALQSGNSQE

SVTEQDSKDSTYSLSSTLTLSKADYEKHKVYACEVTHQGLSSPVTKSFNRGEC

SEQ ID NO: 36: Humanized heavy chain of antibody 33E3.10
EVQLLESGGGLVQPGGSLRLSCAASGFTFSNSAMTWVRQAPGKRLEWVASISGGGTTYYPDSVKGRFTISRDNSKNTLYLQMN SLRAEDTAVYYCARSHYWGQGTLVTVSSASTKGPSVFPLAPCSRSTSESTAALGCLVKDYFPEPVTVSWNSGALTSGVHTFPA VLQSSGLYSLSSVVTVPSSSLGTKTYTCNVDHKPSNTKVDKRVESKYGPPCPPCPAPEAAGGPSVFLFPPKPKDTLMISRTPE VTCVVVDVSQEDPEVQFNWYVDGVEVHNAKTKPREEQFNSTYRVVSVLTVLHQDWLNGKEYKCKVSNKGLPSSIEKTISKAKG QPREPQVYTLPPSQEEMTKNQVSLTCLVKGFYPSDIAVEWESNGQPENNYKTTPPVLDSDGSFFLYSRLTVDKSRWQEGNVFS

CSVMHEALHNHYTQKSLSLSLGK

SEQ ID NO: 37: Humanized light chain of antibody 33E3.10
DIQMTQSPSSVSASVGDRVTITCKASQNVVTNVAWYQQKPGKSPKALIYSASYRYSGVPSRFSGSGSGTDFTLTISSLQPEDF ATYFCQQYNSYPYTFGGGTKVEIKRTVAAPSVFIFPPSDEQLKSGTASVVCLLNNFYPREAKVQWKVDNALQSGNSQESVTEQ

DSKDSTYSLSSTLTLSKADYEKHKVYACEVTHQGLSSPVTKSFNRGEC

SEQ ID NO: 38: heavy chain variable region (antibody 27A12.70)
DVQLQESGPDLVKPSQSLSLTCTVTGYSITSGYSWHWIRQFPGNKLEWMGYIHYSGIANYNPSLKSRISITRDTSKNHFFLQL

NSVTTEDTATYYCATEKTGFFDYWGQGTTLTVSS

SEQ ID NO: 39: light chain variable region (antibody 27A12.70)
DVVMTQTPLSLPVSLGDQASISCRSSQSLVHSNGNTYLHWYLQKPGQSPKLLIYKVSNRFSGVPDRFSGSGSGTDFTLKISRV

EAEDLGVYFCSQSAHVPPTFGGGTKLEIKR

SEQ ID NO: 40: heavy chain variable region (antibody 29E7.35)
AVQLQESGPDLVKPSHSLSLTCTVTGYSITSGYSWHWIRQFPGNKLEWMGYIHYSGSANYNPSLKSRFSITRDTSKNQFFLQL

NSVTTEDTATYYCATEKTGFFDYWGQGTTLTVSS

SEQ ID NO: 41: light chain variable region (antibody 29E7.35)
DVVMTQTPLSLPVSLGDQASISCRSSQSLVHSNGNTYLHWYLQKPGQSPKLLIYKVSNRFSGVPDRFSGSGSGTDFTLKISRV

EAEDLGVYFCSQSAHVPPTFGGGTKLEIKR

SEQ ID NO: 42: heavy chain variable region (antibody 17G8.7VL)
DVQLQESGPDLVKPSQSLSLTCTVTGYSIASGYSWHWIRQFPGNKLEWMGYIHFSGSANYNPSLKSRISITRDTSKNQFFLQL

NSVTTEDTATYYCASEARGYFDYWGQGTTLTVSS

SEQ ID NO: 43: light chain variable region (antibody 17G8.7VL)
DVLMTQTPLSLPVSLGDQASISCRSSQSIVRSNGNTYLTWYLQKPGQSPKLLIYKVSNRFSGVPDRFSGSGSGTDFTLKISRV

EAEDLGVYFCFQGSHVPPTFGSGTKLEIKR

SEQ ID NO: 44: heavy chain variable region (antibody 33E3.10)
EVKLVESGGGLVKPGGSLKLSCAASGFTFSNSAMTWVRQTPEKRLEWVASISGGGTTYYPDSVKGRFTISRDNARNILYLQMS

SLRSEDTAIYYCARSHYWGQGTTLTVSS

SEQ ID NO: 45: light chain variable region (antibody 33E3.10)
DIVMTQSQKFMSTSIGDRVSVTCKASQNVVTNVAWYQQKPGQSPKALIYSASYRYSGVPDRFTGSGSGTDFTLTISNVQSEDL

AEYFCQQYNSYPYTFGGGTKLEIKR

EXAMPLES

Example 1

Methods
Peptide Synthesis and Screening Assays

Linear and CLIPS peptides were synthesized based on the amino acid sequence of the target peptide (i.e. TYSSPEDGIHELFPAPDGEEDTAELQGGC (SEQ ID NO: 27)) using standard Fmoc-chemistry and deprotected using trifluoric acid with scavengers. The linear and CLIPS peptides were short fragments of various length, which may possibly contain the epitope. The constrained CLIPS peptides were synthesized on chemical scaffold in order to reconstruct conformational epitopes, using Chemically Linked Peptides on Scaffolds (CLIPS) technology. For example, the single looped peptides were synthesized containing a dicysteine, which was cyclized by treating with alpha, alpha'-dibromoxylene. The size of the loop was varied by introducing cysteine residues at variable spacing. If other cysteines besides the newly introduced cysteines were present, they were replaced by alanine. The side-chains of the multiple cysteines in the peptides were coupled to CLIPS templates by reacting onto credit-card format polypropylene PEPSCAN cards (455 peptide formats/card) with a 0.5 mM solution of CLIPS template such as 1,3-bis (bromomethyl) benzene in ammonium bicarbonate (20 mM, pH 7.9)/acetonitrile (1:1 (v/v)). The cards were gently shaken in the solution for 30 to 60 minutes while completely covered in solution. Finally, the cards were washed extensively with excess of $H_2O$ and sonicated in disrupt-buffer containing 1 percent SDS/0.1 percent beta-mercaptoethanol in PBS (pH 7.2) at 70° C. for 30 minutes, followed by sonication in $H_2O$ for another 45 minutes.

The binding of antibody to each peptide was tested in a PEPSCAN-based ELISA. The 455-well credit card format polypropylene cars containing the covalently linked peptides were incubated with primary antibody solution consisting of 0.05 micrograms antibody/mL diluted in blocking solution, i.e., 4% horse serum, 5% ovalbumin (w/v) in PBS/0.1% Tween. After washing, the peptides were incubated with a 1/1000 dilution of antibody peroxidase conjugate for one hour at 25° C. After washing, the peroxidase substrate 2,2'-azino-di-3-ehtylbenzthiazoline sulfonate (ABTS) and 2 microliters of 3 percent $H_2O_2$ were added. After one hour, the colour development was measured. The colour development was quantified with a charge coupled device (CCD)-camera and an image processing system (as firstly described in Slootstra et al. Mol Divers. 1996 February; 1(2):87-96).

Data Calculation
Raw Data: Optical Density (Arbitrary OD Units)

The raw data were optical values obtained by a CCD-camera. The values mostly ranged from 0 to 3000, a log scale similar to 1 to 3 of a standard 96-well plate ELISA-reader. First, the CCD camera made a picture of the card prior to peroxidase coloring and then again after the peroxidase colouring. These two pictures were subtracted from each other providing raw data. The raw data were copied into the Peplab™ database. The cards were manually inspected to correct for false-positives (e.g., presence of an air bubble).

Results

The epitopes for antibodies 27A12.70, 29E7.35, 17G8.72, 42H11.51 and 33E3.10 were mapped using the CLIPS™ technology (Timmerman et al. J Mol Recognit. 2007 September-October; 20(5):283-99.) with overlapping 7 to 14-mer linear and CLIPS peptides of which the sequence was based on the peptide used for immunization (SEQ ID NO:27). The epitope for antibodies 27A12.70, 29E7.35, 17G8.72, and 42H11.51 was found to consist of amino acids GIHELF. The epitope for antibody 33E3.10 was found to consist of amino acids LFPAP.

Additionally, alanine-scanning mutagenesis was performed to determine the key amino acids within the epitope for the antibodies 27A12.70, 29E7.35, 17G8.72, and 42H11.51 using a 13-mer peptide ranging from $Tyr^{36}$ through $Pro^{48}$. Alanine-scanning mutagenesis revealed that $Gly^{42}$, $Ile^{43}$ and $Phe^{47}$ are the crucial amino acids within the epitope GIHELF.

Example 2

Animals and Experimental Design

Male Balb/C wild-type mice (10-12 weeks, 25-30 g) received standard diet and water ad libitum. Myocardial infarction was induced by left coronary artery ligation, just below the left atrial appendage. All animal experiments were performed in accordance with the national guidelines on animal care and with prior approval by the Animal Experimentation Committee of Utrecht University.

Myocardial Infarction In Vivo

Mice (Balb/C) were anesthetized with a mixture of Fentanyl (Jansen-Cilag) 0.05 mg/kg, Dormicum (Roche) 5 mg/kg and medetomidine 0.5 mg/kg through an intraperitoneal injection. Core body temperature was maintained around 37° C. during surgery by continuous monitoring with a rectal thermometer and automatic heating blanket. Mice were intubated and ventilated (Harvard Apparatus Inc.) with 100% oxygen. The left coronary artery (LCA) was permanently ligated using an 8-0 vicryl suture. Ischemia was confirmed by bleaching of the myocardium and ventricular tachyarrhythmia. In sham operated animals the suture was placed beneath the LCA without ligating. The chest wall was closed and the animals received subcutaneously Antisedan (Pfizer) 2.5 mg/kg, Anexate (Roche) 0.5 mg/kg and Temgesic (Schering-Plough) 0.1 mg/kg.

Mice underwent cardiac function and geometry assessment 28 days after myocardial infarction. Mice were given intravenously 250 microliters (µl) of saline (control) or antibody solution via the tail vein. The animals were randomized to receive saline, 27A12.70 (10 mg/kg), 29E7.35 (10 mg/kg), 17G8.72 (10 mg/kg), 42H11.51 (10 mg/kg) or 33E3.10 (10 mg/kg) monoclonal antibody 2 days after infarction. The bolus injections were repeated at day 4 and day 5 post-infarction. The 2nd and 3rd antibody injections were given at a dosage of 10 mg/kg.

Results
Percentage of Survival
Antibodies 27A12.70, 29E7.35, 17G8.72, 42H11.51

No differences were observed between the different groups of mice at baseline (t=0). However, a differential survival profile emerged depending on the antibody tested. The antibodies tested increased survival of mice following myocardial infarction relative to the control situation (saline). Mice treated with the antibodies 27A12.70 and 29E7.35 displayed the highest percentage of survival after myocardial infarction over 30 days follow-up after myocardial infarct (FIG. 1). Specifically, it was observed that the percentage of survival for mice treated with antibodies 27A12.70 and 29E7.35 was significantly improved over the percentage of survival for mice in the control group (saline), where only 50% of mice survived after a period of 30 days post myocardial infarction. Additionally, survival of mice treated with antibodies 17G8.72 and 42H11.51 was improved compared to mice in the control group (saline).

Antibody 33E3.10

Figure 3:
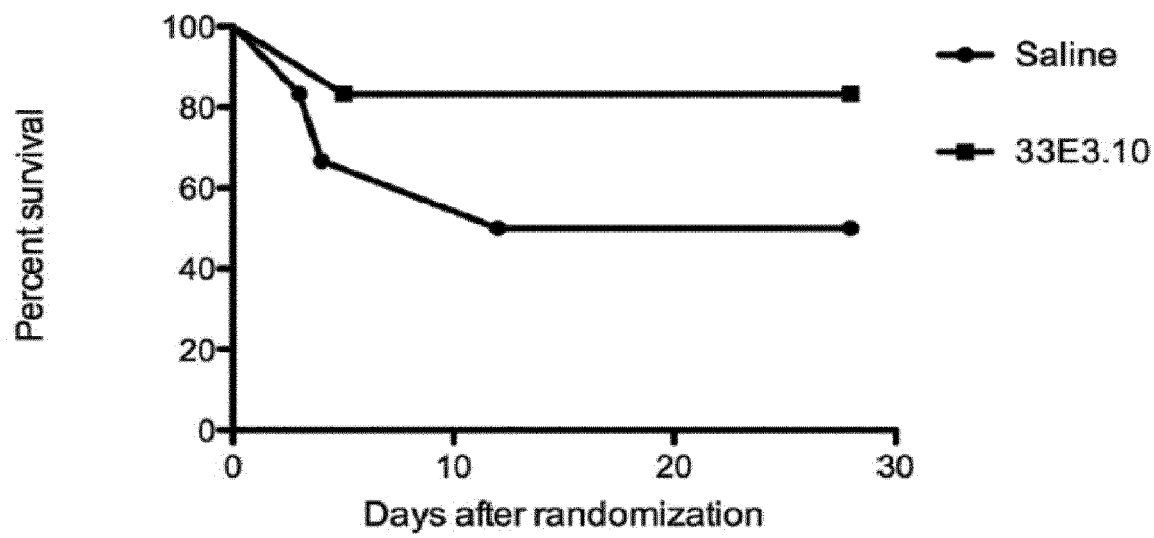
FIG. 3 depicts the percentage of survival following myocardial infarction observed over a period of 30 days for mice treated with antibody 33E3.10, which is directed against the EDA domain of fibronectin-EDA, relative to mice treated with saline.

No differences were observed between the two groups of mice at baseline (t=0). However, a differential survival profile emerged depending on the antibody tested. The antibodies tested increased survival of mice following myocardial infarction relative to the control situation (saline). Mice treated with the antibody 33E3.10 displayed increased survival after myocardial infarction over 30 days follow-up after myocardial infarct (FIG. 3). Specifically, it was observed that the percentage of survival for mice treated with antibody 33E3.10 was significantly improved over the percentage of survival for mice in the control group (saline), where only 50% of mice survived after a period of 30 days post myocardial infarction.

Example 3

Myocardial Infarction In Vivo

Male Balb/C wild-type mice (10-12 weeks, 25-30 g) were subjected to the procedure for induction of myocardial infarction as taught herein in example 2. They were also treated with the same antibodies.

Echocardiography

Mice underwent serial assessments of cardiac dimensions and function by high resolution echocardiography (Vevo 2100, FUJIFILM VisualSonics, Inc., Toronto, Canada) under isoflurane anaesthesia 28 days after myocardial infarction. Long axis and short axis images with 1.0 mm interval between the slices were obtained and used to compute end-diastolic volume (EDV, largest volume) and end-systolic volume (ESV, smallest volume). The ejection fraction (EF) was calculated as 100*(EDV−ESV)/EDV.

Results

Antibodies 27A12.70, 29E7.35, 17G8.72, 42H11.51

Figure 2:
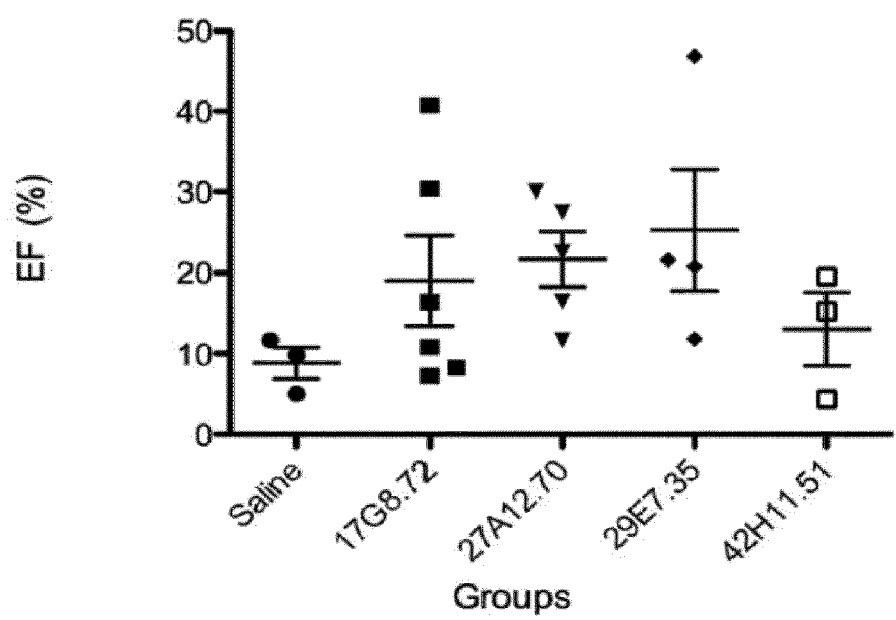
FIG. 2 depicts the ejection fraction (EF) following myocardial infarction for mice treated with various antibodies directed against the EDA domain of the fibronectin-EDA (i.e. 17G8.72, 27A12.70, 29E7.35, and 42H11.51).

The results showed that relative to mice treated with saline, mice treated with antibodies 27A12.70, 29E7.35, 17G8.72 and 42H11.51 displayed improved heart function following myocardial infarction, as indicated by an increase in ejection fraction (EF), with the highest improvement as shown by the higher percentage of EF measurement displayed upon treatment with antibodies 27A12.70 and 29E7.35 (FIG. 2).

Antibody 33E3.10

Figure 4:
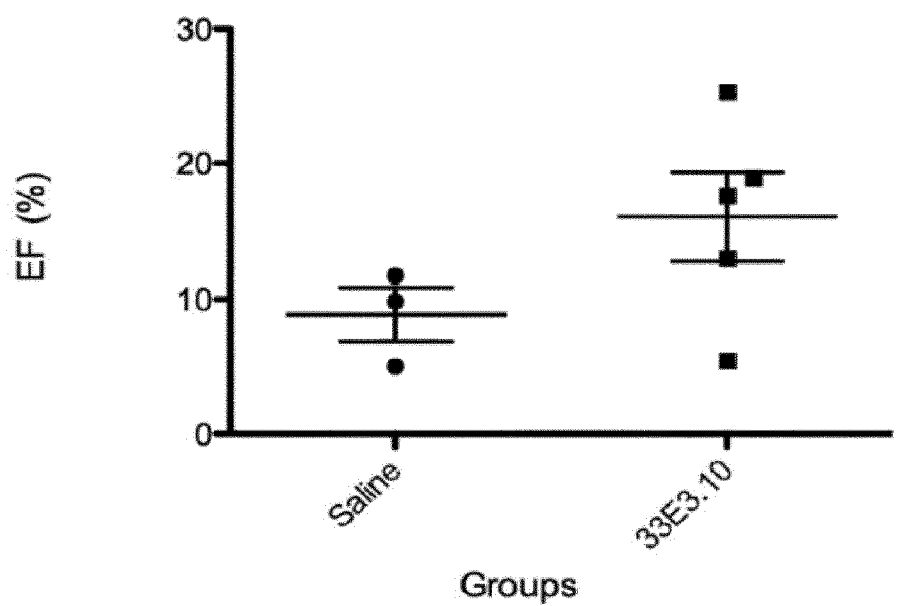
FIG. 4 depicts the ejection fraction (EF) following myocardial infarction for mice treated with antibody 33E3.10, which is directed against the EDA domain of the fibronectin-EDA.

The results showed that relative to mice treated with saline, mice treated with antibody 33E3.10 displayed improved heart function following myocardial infarction, as indicated by an increase in ejection fraction (EF), with the highest improvement as shown by the higher percentage of EF measurement displayed upon treatment with antibody 33E3.10 (FIG. 4).

Example 4

Methods

Peptide synthesis, screening assays and data calculation for alanine-scan of fibronectin-EDA epitope are performed as described in Example 1. Peptides based on TYSSPEDGIHELFP were synthesized wherein in each peptide one amino acid is replaced by an alanine. The peptides were tested for binding by antibodies 27A12.70, 29E7.35, 17G8.72 and 42H11.51.

Results

Results are displayed in the table below.

| Peptide | Replaced amino acid | Antibody binding (arbitrary optical density units) | | | |
|---|---|---|---|---|---|
| | | 17G8.72 | 27A12.70 | 29E7.35 | 42H11.51 |
| TYSSPEDGIHELFP | none | 2087 | 2681 | 2754 | 2845 |
| AYSSPEDGIHELFP | T | 2146 | 2709 | 2779 | 2859 |
| TASSPEDGIHELFP | Y | 2668 | 2786 | 2841 | 2865 |
| TYASPEDGIHELFP | S | 2501 | 2719 | 2735 | 2867 |
| TYSAPEDGIHELFP | S | 2098 | 2680 | 2631 | 2853 |
| TYSSAEDGIHELFP | P | 2091 | 2712 | 2656 | 2866 |
| TYSSPADGIHELFP | E | 2481 | 2693 | 2627 | 2835 |
| TYSSPEAGIHELFP | D | 2646 | 2751 | 2724 | 2834 |
| TYSSPEDAIHELFP | G | 89 | 122 | 81 | 433 |
| TYSSPEDGAHELFP | I | 66 | 91 | 74 | 120 |
| TYSSPEDGIAELFP | H | 2563 | 2405 | 1798 | 2869 |
| TYSSPEDGIHALFP | E | 2101 | 2204 | 302 | 2842 |
| TYSSPEDGIHEAFP | L | 1552 | 1783 | 194 | 2819 |
| TYSSPEDGIHELAP | F | 106 | 249 | 124 | 2642 |

-continued

| Peptide | Replaced amino acid | Antibody binding (arbitrary optical density units) | | | |
| --- | --- | --- | --- | --- | --- |
| | | 17G8.72 | 27A12.70 | 29E7.35 | 42H11.51 |
| TYSSPEDGIHELFA | P | 2164 | 2601 | 2596 | 2869 |
| Epitope | | GIHELF | GIHELF | GIHELF | GIHEL |
| Crucial amino acids | | G, I, F | G, I, F | G, I, E, L, F | G, I |

Example 5

Methods
Animals and Experimental Design

Male Balb/C wild-type (WT) (10-12 wks, 25-30 g) received standard diet and water ad libitum. Myocardial infarction was induced by left coronary artery ligation, just below the left atrial appendage as described in Example 2. Animals were randomized to anti-EDA IgG1 antibody (20 mg/kg; 250 µL) directed against the epitope GIXXXF or saline control. Another group with isotype control (20 mg/kg; 250 µL) was also included at a different time point. Treatment or placebo was initiated intravenously 3 days after MI. A researcher blinded to treatment assessed heart function and geometry. All animal experiments are performed in accordance with the national guidelines on animal care and with prior approval by the Animal Experimentation Committee of Utrecht University.

Anti-EDA IgG1 Monoclonal Antibody

IgG1 and IgG2b isotypes were separately purified from conditioned hybridoma medium by differential pH elution from Protein A Sepharose, and purified IgG1 was used in experiments described in this study.

Infarct Size & Cardiac Magnetic Resonance Imaging

Infarct size was assessed in a subset of mice prior to compound infusion using late Gadolinium enhancement magnetic resonance imaging (LGE-MRI), 3 days after MI. Local and global cardiac function as well as left ventricular geometry was assessed by high resolution MRI (9.4T, Bruker, Rheinstetten, Germany).

Flow Cytometry

Blood was collected in EDTA tubes 7 days after MI. Fifty (50) µL of blood was added to 100 µL of antibody mixture and incubated for 30 min in the dark at RT. After red blood cell lysis using Optilyse buffer (Beckman Coulter) for 10 min the samples were measured on the Gallios (Beckman Coulter).

Quantitative PCR

Isolated total RNA from mouse hearts was reverse transcribed to cDNA using the iScript™ cDNA synthesis kit (Bio-Rad) following the manufacturer's guidelines. Quantitative PCR was performed using the SYBR green (Bio-Rad) method on the iQ™5 Real-Time PCR Detection System (Bio-Rad). The following sets of primers were used in the study: collagen I pro-alpha I chain (forward), (reverse); collagen III pro-alpha I chain (forward), (reverse); TIMP-1 (forward), (reverse); TIMP-2 (forward), (reverse), MMP-2 (forward), (reverse); P0 (forward), (reverse), RPL27 (forward), (reverse), EDA-FN (forward), (reverse), total FN (forward), (reverse). Each sample was run in duplicate. Gene expression levels were normalized to P0 and RPL27 using the protocol described in (Willems, Leyns, & Vandesompele, Anal Biochem. 2008 Aug. 1; 379(1):127-9). To assess qPCR efficiency, a standard curve with 5 different cDNA dilutions was included.

Zymography

MMP activity in the infarcted myocardium and in collagen pads was examined by gelatin zymography. Running gel (2.68 ml 30% (bis)acrylamide (Bio-Rad), 4.82 ml 2 mg/ml porcine skin gelatin solution (Sigma-Aldrich), 2.5 ml Tris-HCl 1.5 M pH 8.8 (Roche), 100 µl 10% SDS (Sigma-Aldrich) 50 µl APS and 17.8 µl of TEMED (GE Life Sciences, Pittsburgh, US)) and stacking gel (0.67 ml 30% (bis)acrylamide, 3.04 ml aqua dest, 1.25 ml Tris-HCl 0.5 M pH 6.8, 50 µl 10% SDS, 25 µl APS, and 8.8 µl of TEMED)) were poured. Myocardial samples were homogenized in Roche lysis buffer. The protein concentration was measured using BCA Protein Assay Kit (Thermo Scientific).The myocardial extracts at 5 µg were mixed in a ratio 1:4 with Laemlli buffer and loaded on the gels. The gels were run at 30 mA through stacking phase and at 60 mA for running phase. After running the gels were washed 2×15 min in 2.5% Triton X-100 to remove SDS. Then, gels were incubated overnight in Brij-solution (50 mM Tris-HCl pH 7.4; 10 mM CaCl2) (Merck, Whitehouse Station, USA); 0.05% Brij35 (Sigma-Aldrich)). After incubation, the gels were stained with Coomassie blue (0.1% Coomassie Brilliant blue R-250 (Bio-Rad), 25% methanol and 15% acetic acid (both from Sigma-Aldrich)) and subsequently destained (in 25% methanol and 15% acetic acid) until clear bands appeared against blue background. Pictures were taken on a Chemidoc XRS+. Images were analyzed using ImageLab (Bio-Rad).

Cell Culture

Human mammary endothelial cells (HMECs) were cultured in MCDB131 medium (10372-019,Gibco) supplemented with 10% FBS, pen/strep, 50 mM Hydrocortison, 50 mM epidermal growth factor and L-glutamine. Cells were subcultured every three days. The NIH3T3 fibroblast cell line was used for adhesion studies. Cells were cultured in DMEM medium (41965, Gibco) supplemented with 10% FBS and pen/strep. Cells were subcultured every three days.

Sprouting Assay

Cytex beads were coated with HMECs and placed in matrigel (Corning). Bare MCDB131 medium was used as a negative control, full MCDB131 as positive control. EDA fragments and III4 fragments were added in a concentration of 1 µM. Pictures were taken at 48 hours and quantified using photoshop and ImageJ.

Cell Adhesion Assay

Ninety-six (96) wells plate was coated with 1 µM of EDA-his or III4-his fragments for 1 hour at 37° C., then blocked with PBS 1% BSA. NIH3T3 0.5×10^5 cells were added per well in bare DMEM and incubated for 1 hour at 37° C. After washing of unattached cells, the attached cells were fixed and stained using 0.5% crystal violet 1% formaldehyde, 20% methanol. The plate was read with a microplate reader at 540 nm.

Protein Purification

BL21 pLysS *E. coli* were transformed with 1 μl of the DNA constructs and plated on Yeast tryptone ampicillin/chloramphenicol plates overnight. The next day all the colonies were scraped off and grown in LB medium with Amp/Chlor till an OD of 0.6-0.8 was reached. IPTG was added to start the production of the protein. After 24 hours, bacteria were pelleted and lysed, using lysis buffer and sonication steps. Debris was pelleted and supernatant was used for further processing. Ni-NTA beads were used for his purification. Briefly, Ni-NTA beads were incubated ON with supernatant at 4° C. Beads were poured into columns on the ACTA system. After a couple of washes, bound EDA-his or III4-his was eluted using 300 mM imidazole. Fractions containing EDA-his or III4-his were collected and injected on a gel filtration column. Proteins were separated based on size and eluted in HEPES buffer. Fractions containing EDA-his or III4-his were pooled and concentrated using Vivaspin 5 kD concentration columns. Fragment concentration was assessed using BCA kit. LAL assays were performed to check for endotoxins. Fragments were used with a concentration lower than <0.1 EU per uM.

Histology

Upon termination, hearts were excised and fixated in 4% formaldehyde and embedded in paraffin. Paraffin sections were stained for Ly-6G (for neutrophils; rat anti-mouse Ly-6G, Abcam, Cambridge, United Kingdom), MAC-3 (for macrophages; rat anti-mouse MAC-3, BD Pharmingen, Breda, the Netherlands) and CD31 (for vessels, Santa Cruz, Heidelberg, Germany).

Before staining, sections were deparaffinized and endogenous peroxidase was blocked by 30 minutes incubation in methanol containing 1.5% H2O2. Antigen retrieval was performed by 20 minutes boiling in citrate buffer (MAC-3 and CD31) or by 15 minutes incubation at 37° C. in a 0.08% pepsin solution (Ly-6G).

For MAC-3 staining, sections were pre-incubated with normal goat serum and incubated overnight at 4° C. (MAC-3, 1:30; CD163, 1:500). For CD31 staining, sections were incubated overnight at RT with the primary antibody (1:1500). Sections were then incubated for 1 hour at RT with a biotin labeled secondary goat antibody and 1 hour incubation with streptavidin-horseradish peroxidase at RT. All sections were developed with AEC.

For Ly-6G, sections were incubated for 1 hour at RT with the primary antibody (1:100). Sections were then incubated for 30 minutes with Powervision poly-HRP anti-rabbit IgG (ImmunoVision Technologies, Daily City, USA). The staining was immediately visualized with Vector NovaRED™ substrate kit following the manufacturer's instructions (Vector Laboratories Inc., Burlingame, USA).

All sections were counterstained with Mayer's hematoxylin stain.

Quantification of collagen density was performed using Picrosirius Red staining of 4% formalin fixated and paraffin embedded heart sections. Collagen density analysis was done with circularly polarized light after conversion into grey values and digital image microscopy. Grey values below 30 were considered as background signal of the image Human EDA Staining after Acute MI Myocardial tissue was obtained during autopsy of patients who died due to a myocardial infarction, and was retrieved from the Pathology archive. The study met the criteria of the code of proper use human tissue that is used in the Netherlands. To visualize EDA, sections were incubated with our monoclonal mouse-anti EDA antibody (dilution 1/800) after boiling in citrate buffer (pH 6.0). Poly AP-Anti-Mouse IgG (Immunologic, Duiven, the Netherlands) was used as secondary antibody and the signal was visualized using Liquid permanent red (Dako, Glostrup, Denmark).

Statistics

Data are represented as Mean±SEM. One-way ANOVA with post-hoc 2-sided Dunnett t-test adjustment (saline was set as control) was used for multiple comparisons between groups. Mann-Whitney U test was used to compare the difference in survival between anti-EDA and saline treated animals. All statistical analyses were performed using SPSS 15.1.1. and p<0.05 was considered significant.

Results

Figure 5A:
Figure 5B:
Figure 5C:
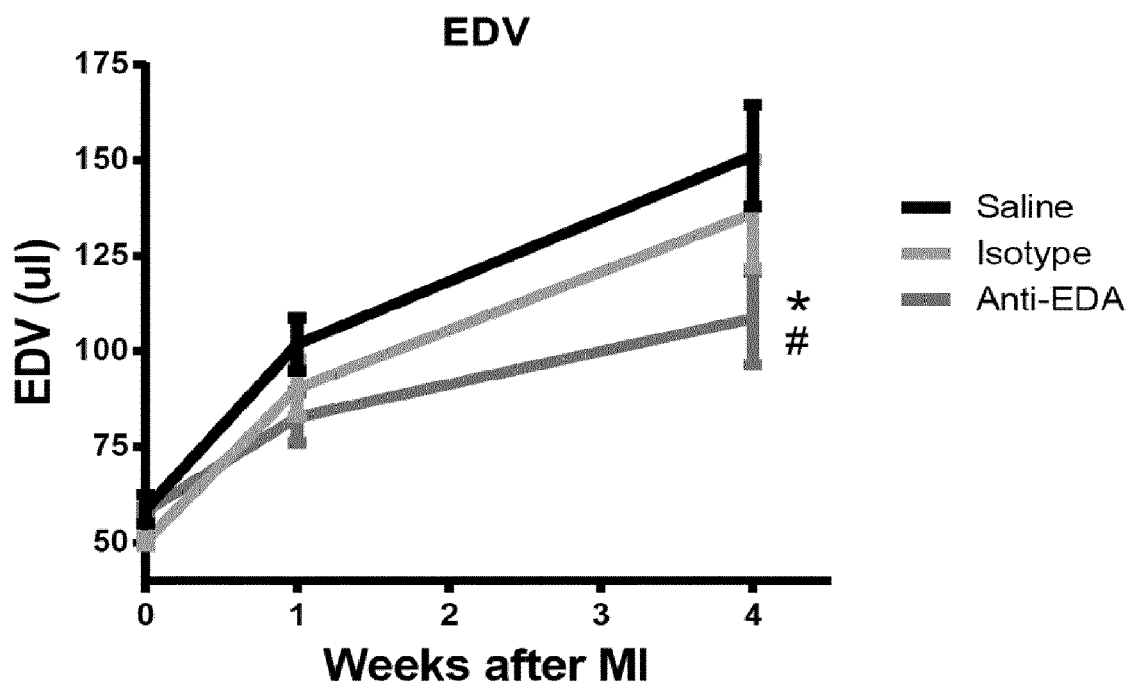
Figure 5D:
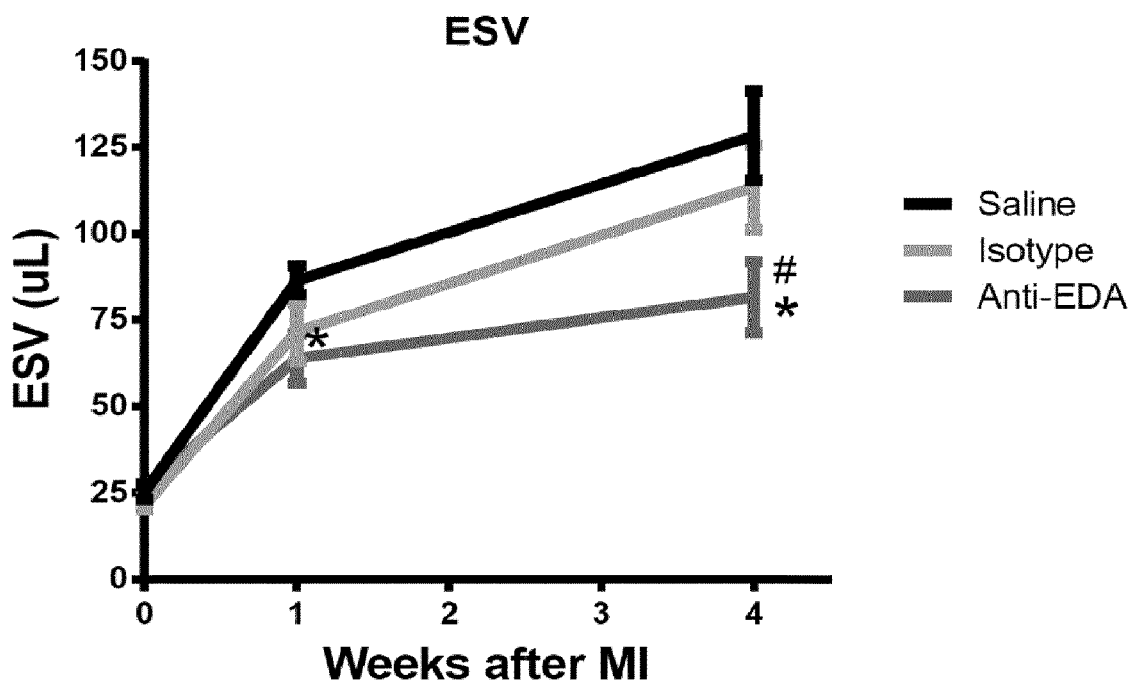

Anti-EDA Treatment Improves Survival and Prevents Adverse Remodeling after Myocardial Infarction Baseline MRI assessment of cardiac function and dimensions revealed no differences between the treatment groups. Infarct size was 42±3% prior to compound infusion (FIG. 5A). During the study period of 28 days, 3/9 of anti-EDA treated mice were found dead, while 9/14 saline treated animals died during follow-up (p=0.06). Pathological analysis revealed only 2 ruptures (both in saline group), while in the remaining cadavers excessive lung congestion was noticeable. Serial MRI assessments of cardiac function and geometry showed a significantly preserved left ventricular function as well as dimension in anti-EDA treated animals compared to both saline and isotype control (FIG. 5; Table 1).

TABLE 1

Cardiac function and geometry after acute MI

| | Saline | | | Anti-EDA | | | | |
|---|---|---|---|---|---|---|---|---|
| | Baseline | 7 days MI | 28 days MI | Baseline | 7 days MI | †p | 28 days MI | †p |
| EDV, μL | 58.7 ± 3.8 | 101.9 ± 6.9* | 151.2 ± 13.4** | 58.2 ± 1.0 | 82.8 ± 6.7*† | 0.052 | 106.5 ± 10.2**† | 0.021 |
| ESV, μL | 25.1 ± 2.2 | 86.3 ± 4.3* | 128.3 ± 12.9** | 26.4 ± .7 | 63.8 ± 7.2*† | 0.011 | 81.6 ± 10.4**† | 0.014 |
| EF, % | 57.1 ± 3.2 | 14.7 ± 2.8* | 15.7 ± 2.0** | 54.7 ± 1.3 | 23.6 ± 3.0* | NS | 24.4 ± 2.5**† | 0.067 |
| WT septum (remote, mm) | 0.90 ± 0.02 | 0.70 ± 0.03* | 0.91 ± 0.04 | 0.99 ± 0.01 | 0.97 ± 0.02*† | 0.01 | 0.94 ± 0.03 | NS |
| WT free wall (infarct, mm) | 0.93 ± 0.02 | 0.57 ± 0.04* | 0.56 ± 0.03** | 0.91 ± 0.01 | 0.65 ± 0.06* | NS | 0.60 ± 0.04** | NS |

TABLE 1-continued

Cardiac function and geometry after acute MI

| | Saline | | | Anti-EDA | | | | |
| --- | --- | --- | --- | --- | --- | --- | --- | --- |
| | Baseline | 7 days MI | 28 days MI | Baseline | 7 days MI | †p | 28 days MI | †p |
| SWT septum (remote, %) | 49.2 ± 2.0 | 49.7 ± 5.0 | 42.4 ± 3.7 | 50.9 ± 2.9 | 32.0 ± 2.4*† | 0.006 | 27.8 ± 8.6** | NS |
| SWT free wall (infarct, %) | 54.8 ± 2.3 | −23.7 ± 4.7* | −26.5 ± 3.5** | 51.1 ± 5.0 | −8.2 ± 4.6*† | 0.047 | −7.8 ± 3.1**† | 0.002 |

Data are represented as Mean ± SEM.
*p-values are compared to baseline and below 0.05 level;
†p-value compared to saline treatment.
BPM = beats per minute, EDV = end-diastolic volume, ESV = end-systolic volume, EF = ejection fraction, WT = wall thickness, SWT = systolic wall thickening, NS = not significant.

Figure 6A:
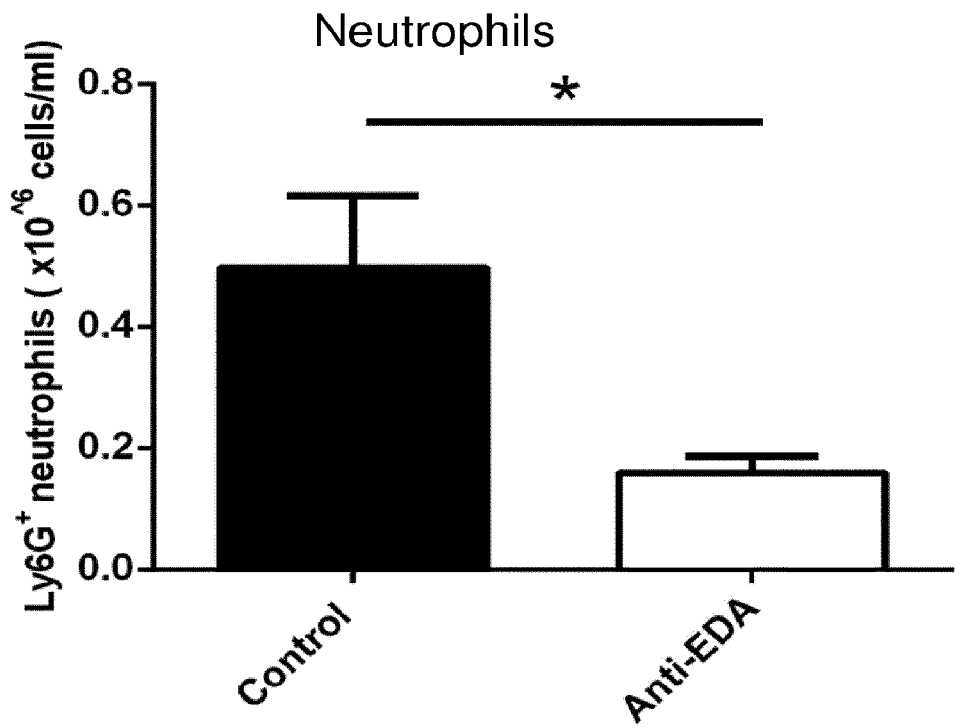
Figure 6B:
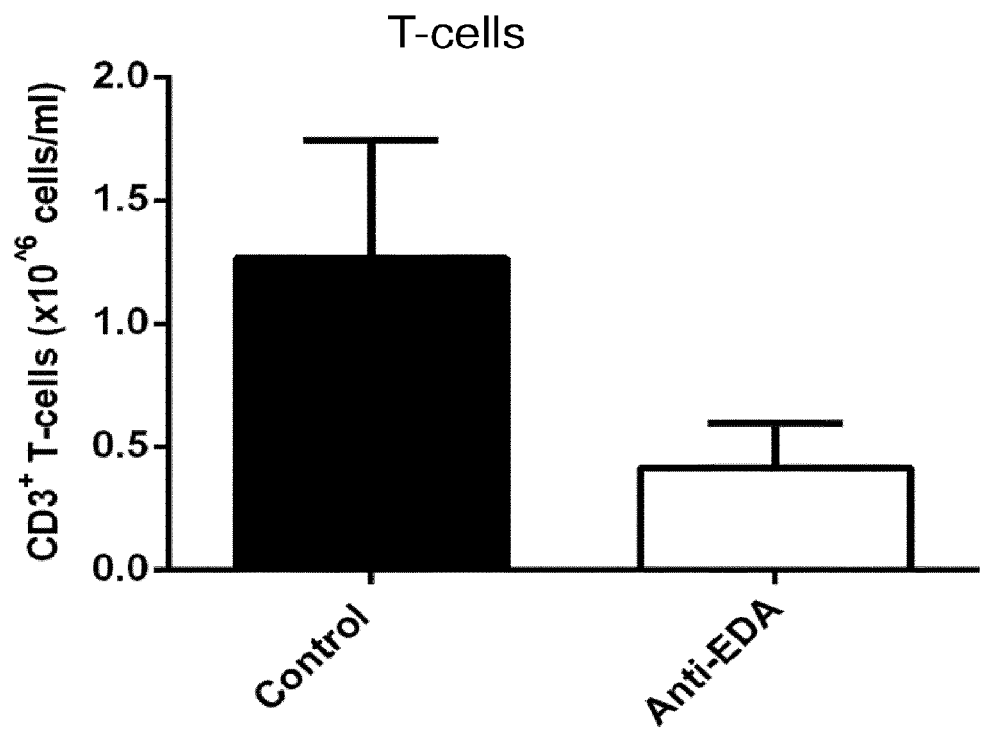
Figure 6C:
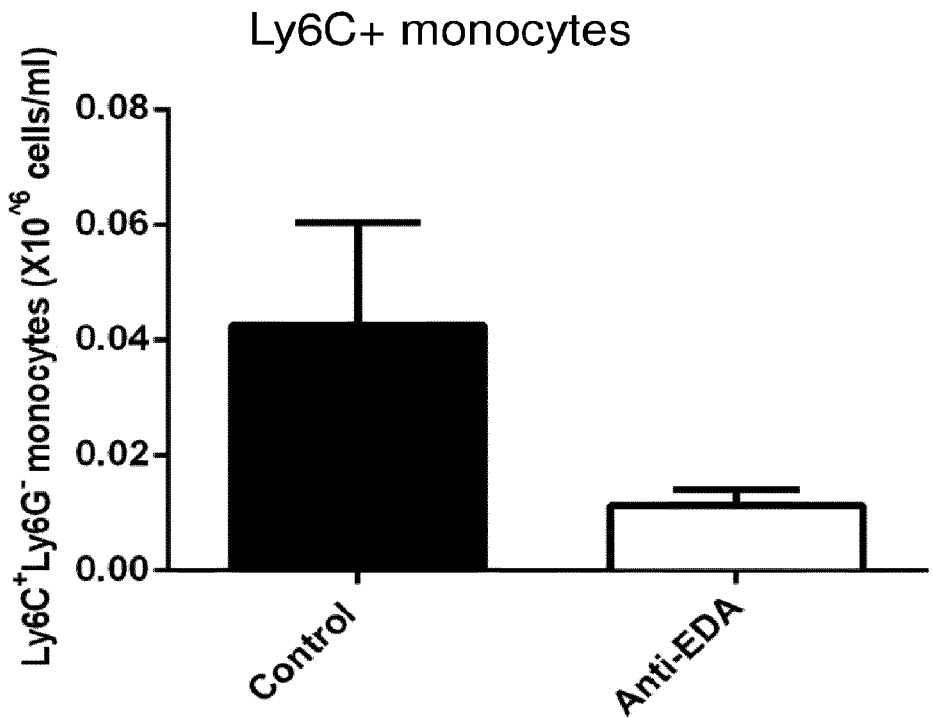
Figure 6D:
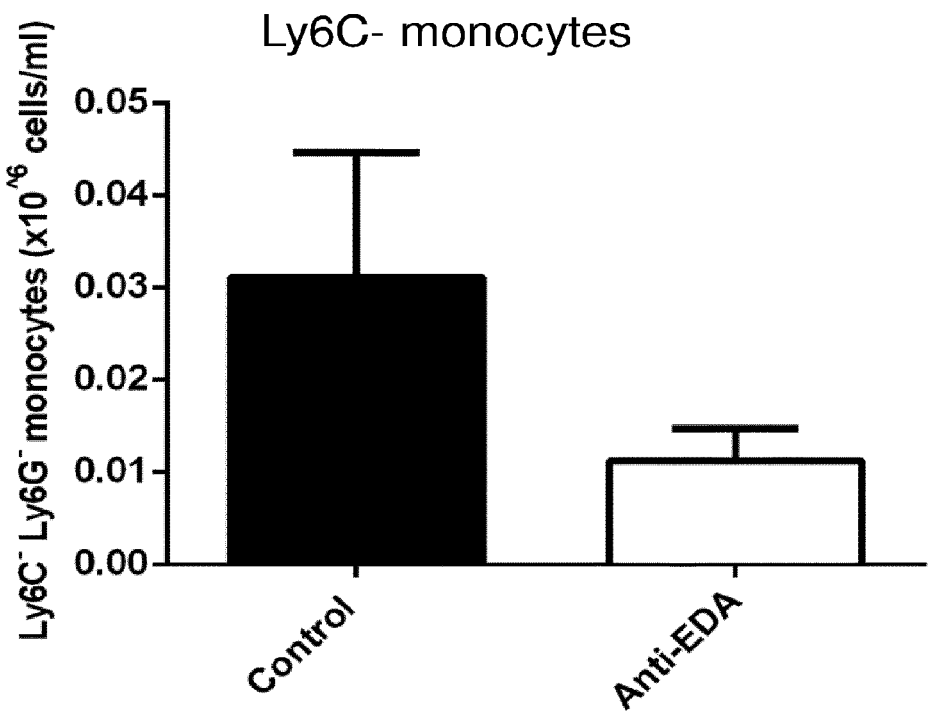
Figure 6E:
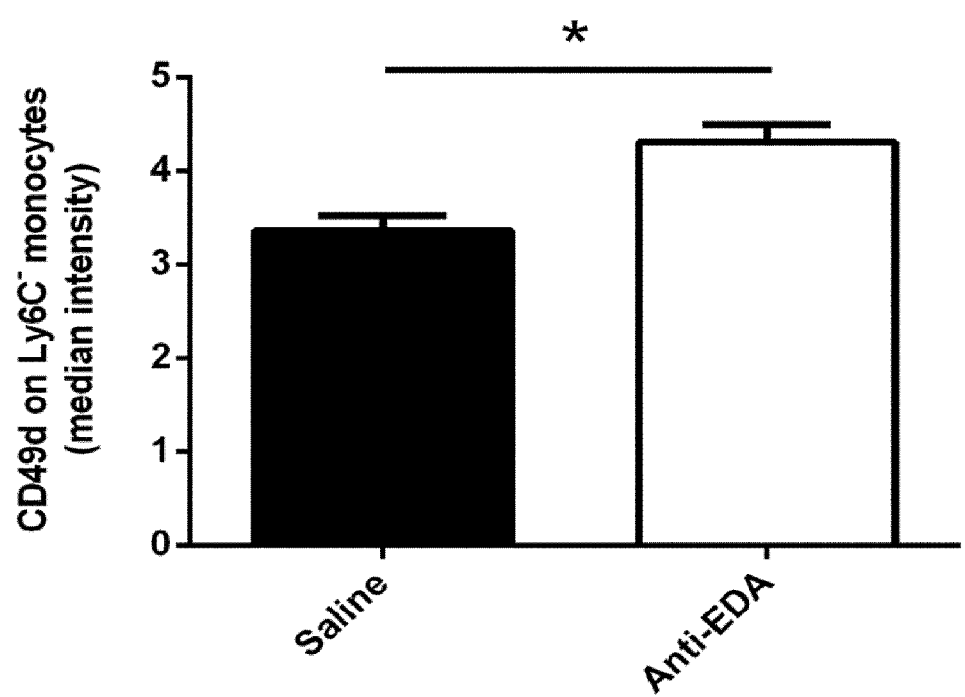

Circulating Leukocyte Numbers are Decreased in Anti-EDA Treated Mice/Anti-EDA Treatment Reduces Leukocyte Numbers in Peripheral Blood after MI Leukocyte subset numbers in the blood were assessed using flow cytometry 7 days after MI. Anti-EDA treated mice showed a significant reduction in neutrophils and a trend towards reduced T-cell number after anti-EDA treatment (FIGS. 6a and b). The inflammatory Ly6C$^{pos}$ monocyte subset and the anti-inflammatory Ly6C$^{neg}$ monocyte subset were both not significantly decreased after anti-EDA treatment (FIGS. 6c and d).

Figure 7A:
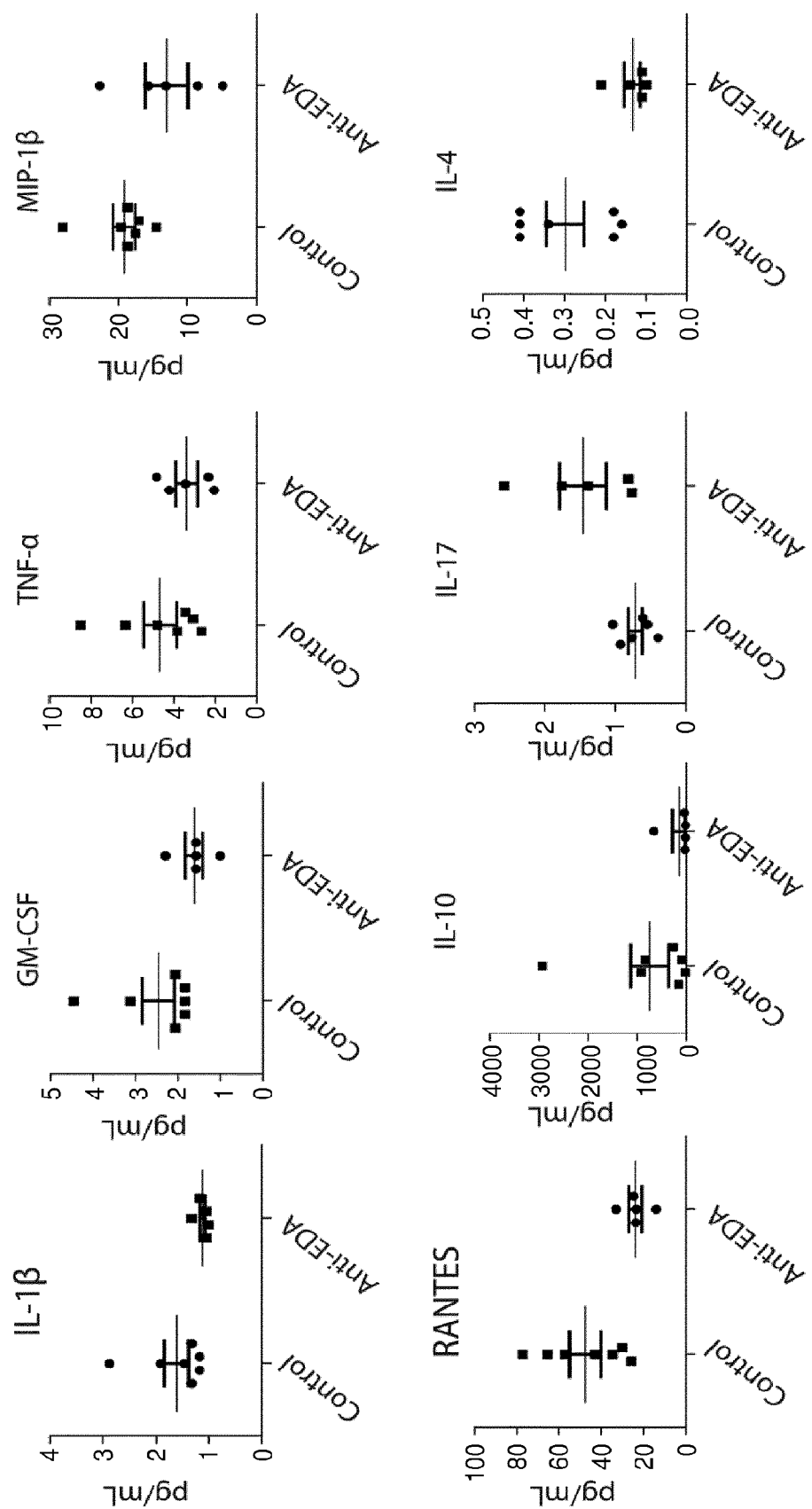
Figure 7B:
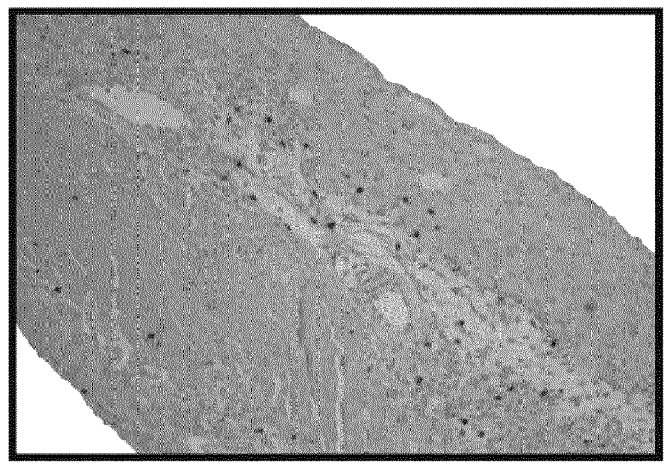
Figure 7C:
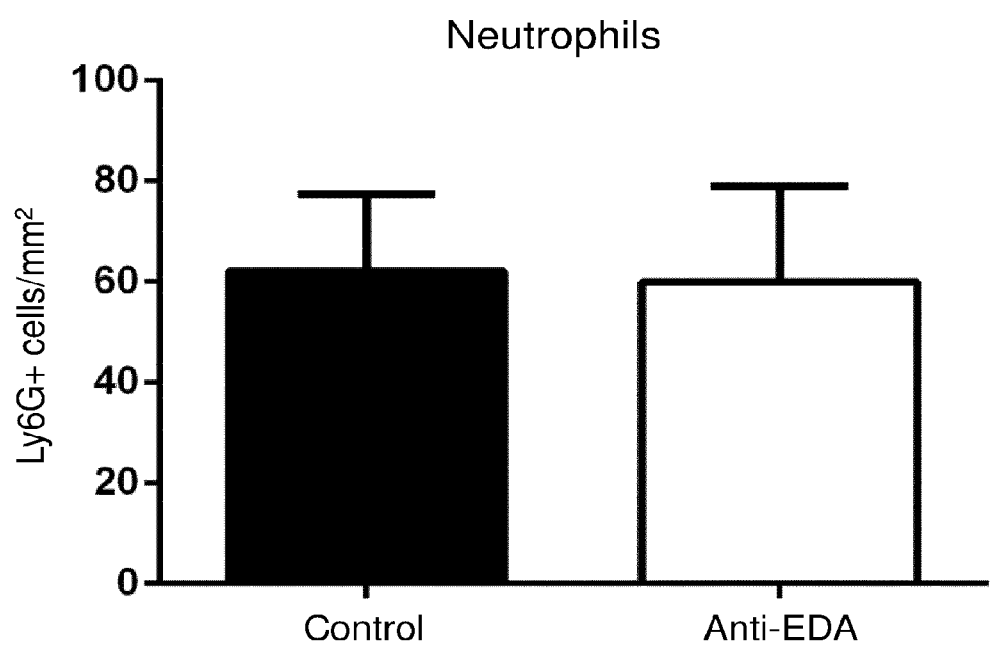
Figure 7D:
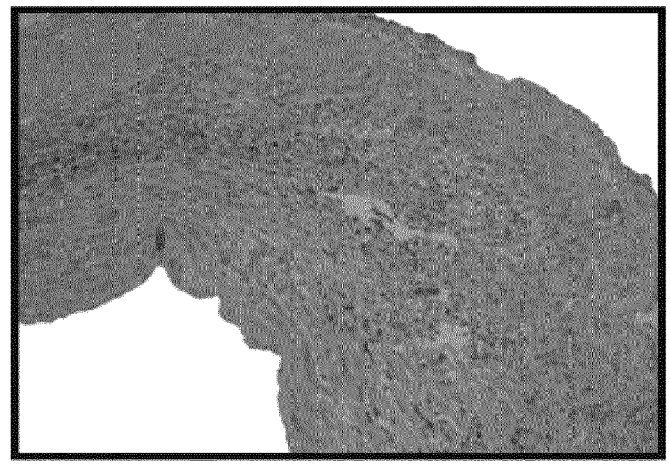
Figure 7E:
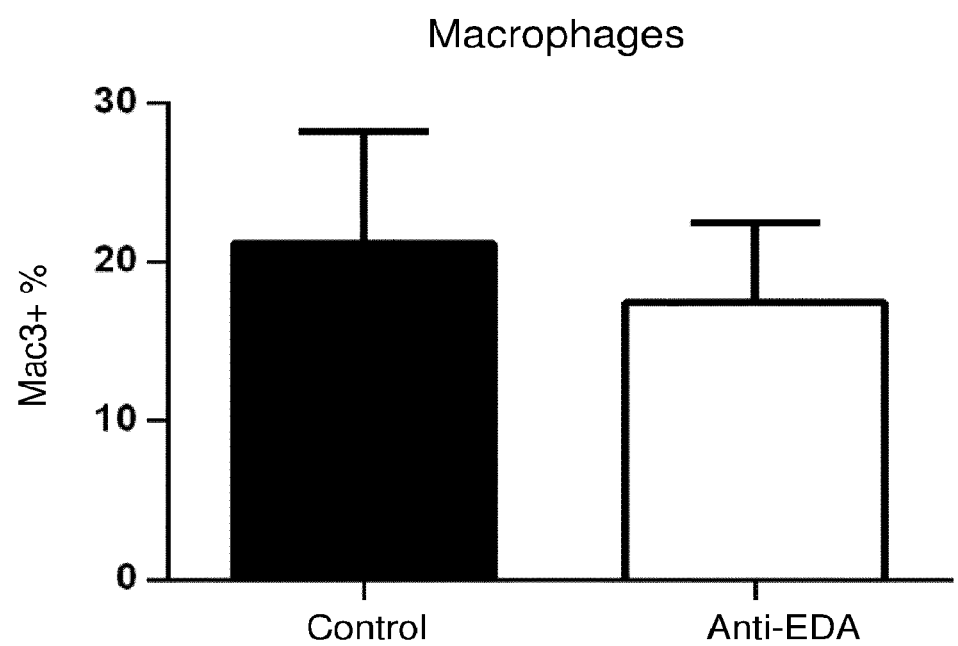

Anti-EDA Treatment Reduces Cytokine Burst but not Leukocyte Numbers in the Infarcted Heart In the infarcted area, the inflammatory cytokines IL-1β, TNFα, GM-CSF, IL-4, RANTES, IL-10 and MIP-1α were decreased in the anti-EDA treated animals (FIG. 7a). No difference was observed in cytokine levels in the remote area of the heart (data not show). Neutrophil, T-cell and macrophage numbers were not affected by anti-EDA treatment 7 days after MI (FIG. 7b to e).

Anti-EDA Treatment does not Affect Proper Scar Formation

Figure 8A:
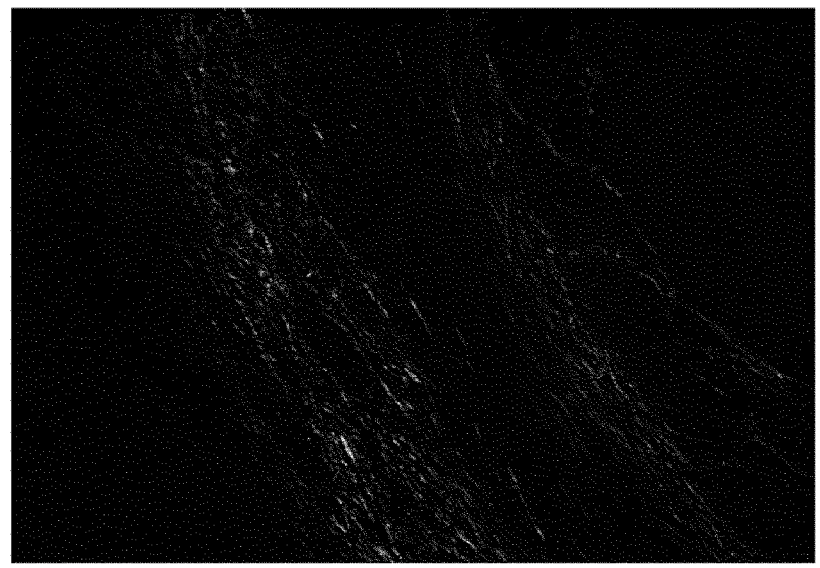
Figure 8B:
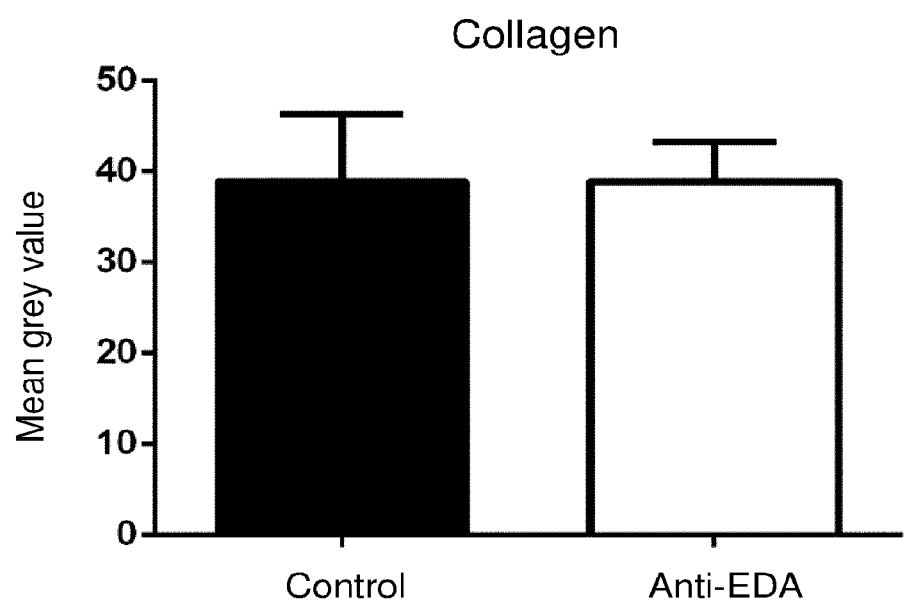
Figure 8C:
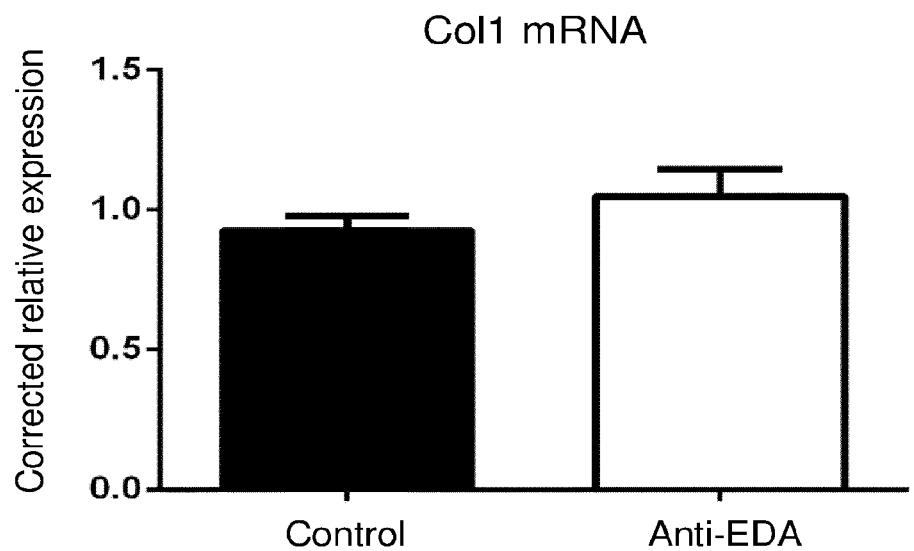
Figure 8D:
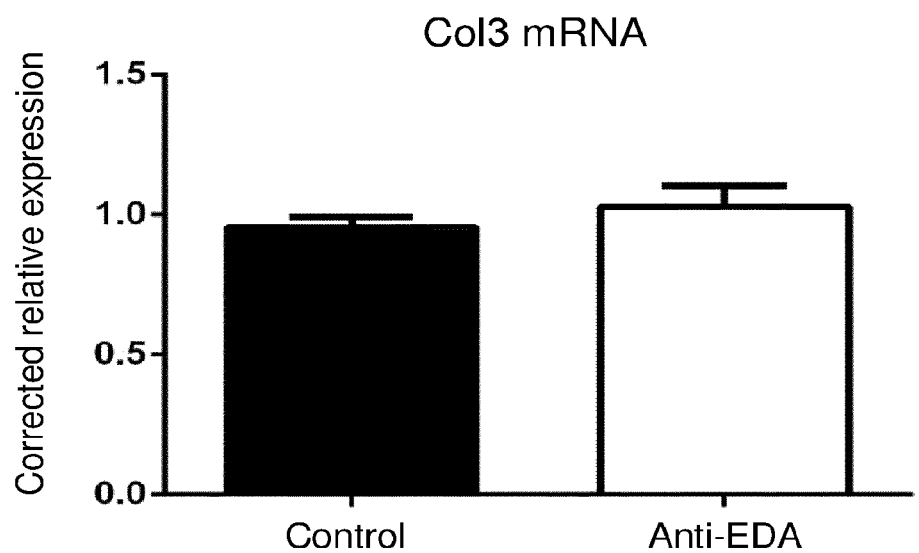
Figures 9A, 9B:
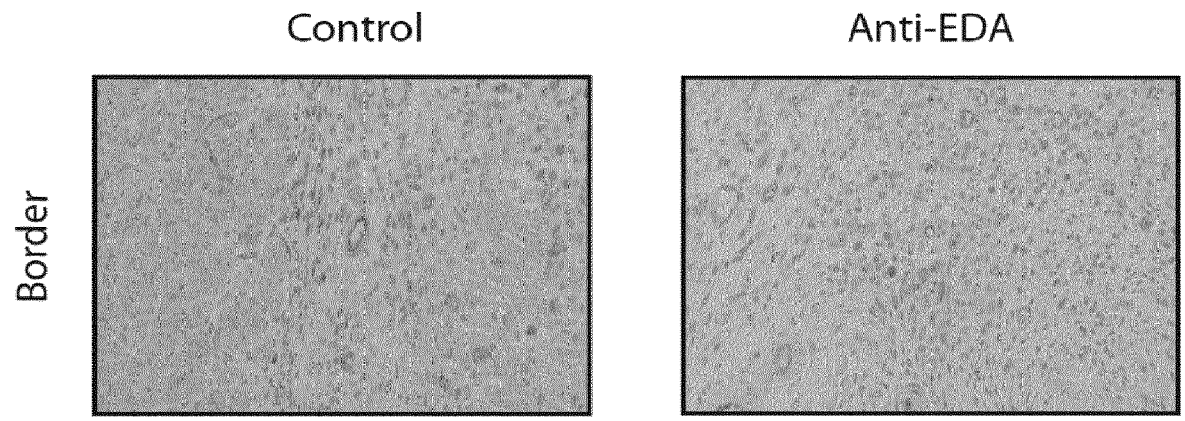
Figure 9C:
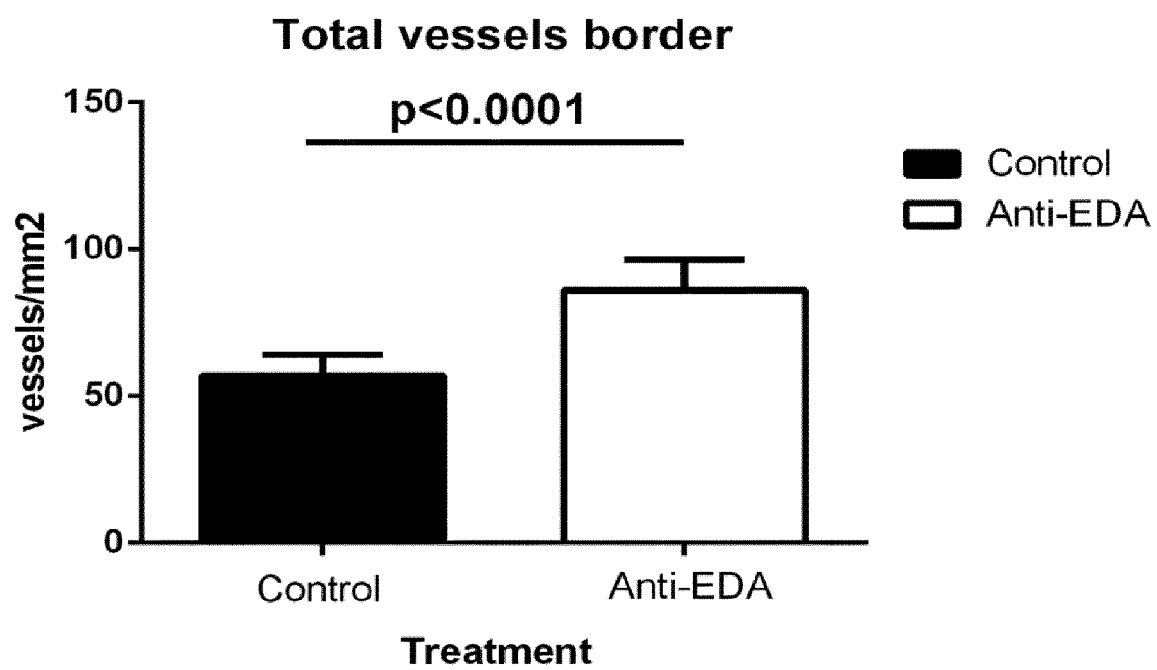
Figure 9D:
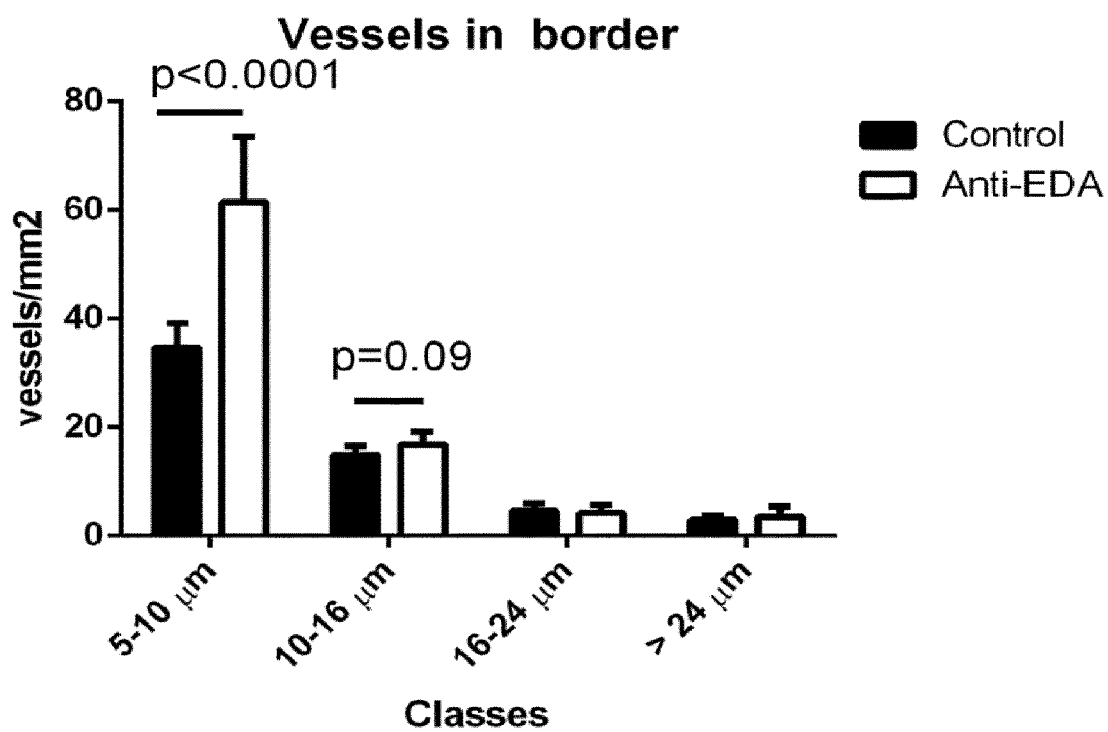
Figure 9E:
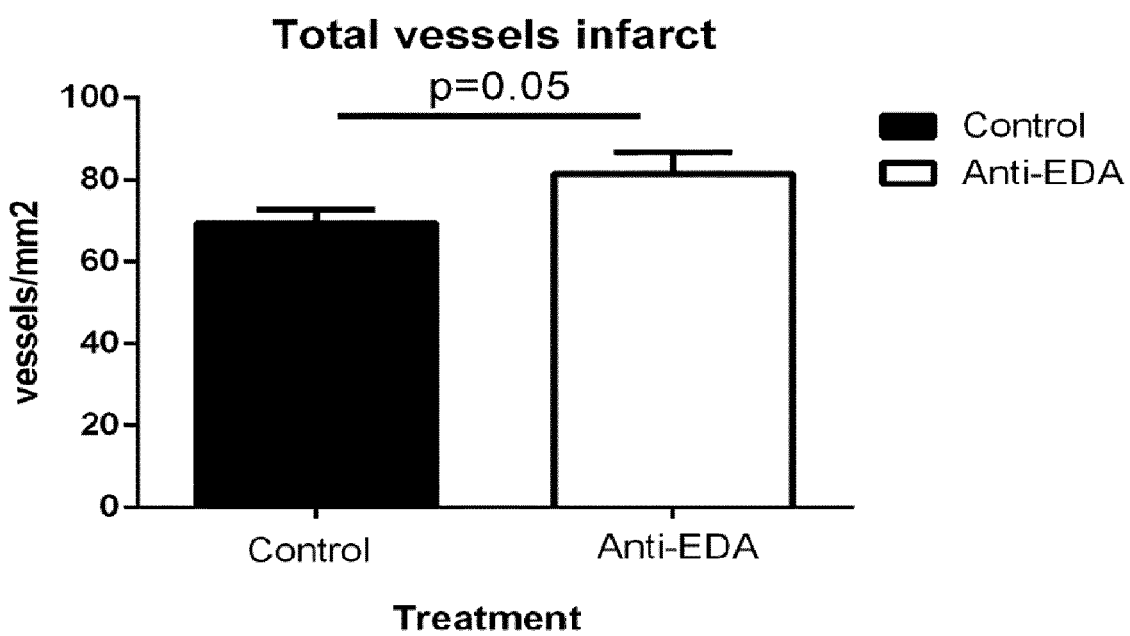
Figure 9F:
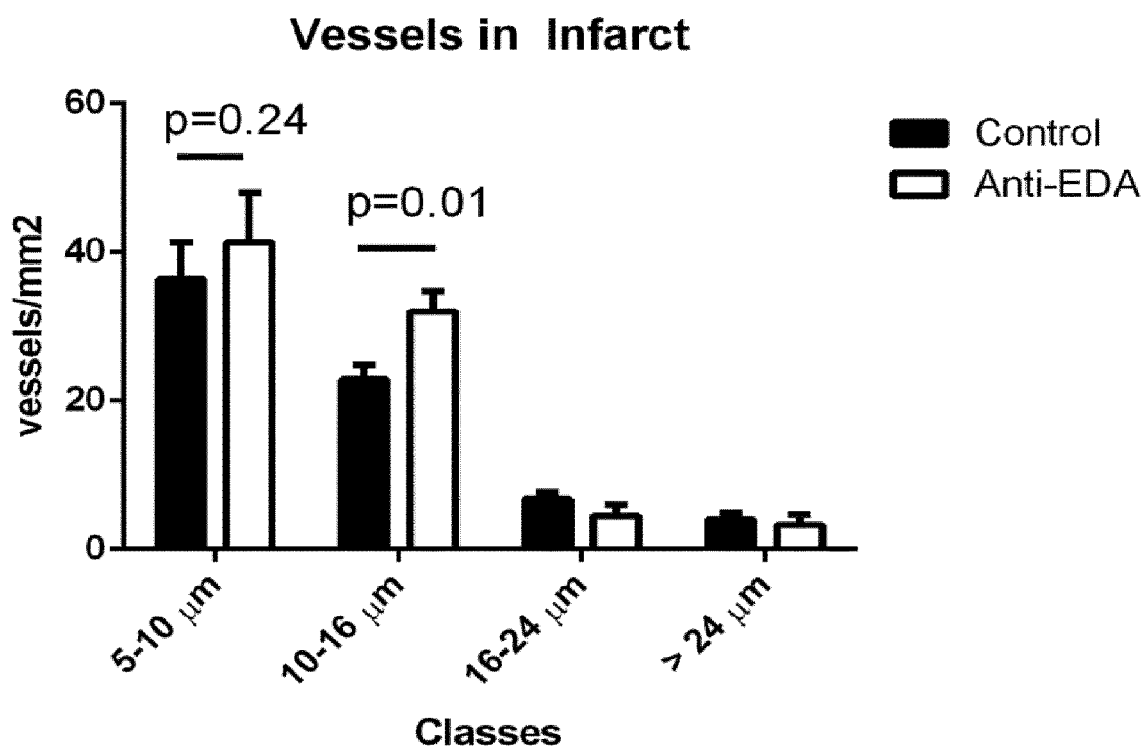
Figure 9G:
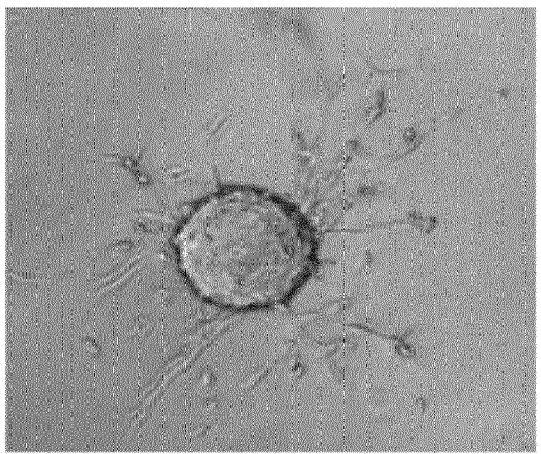
Figure 9H:
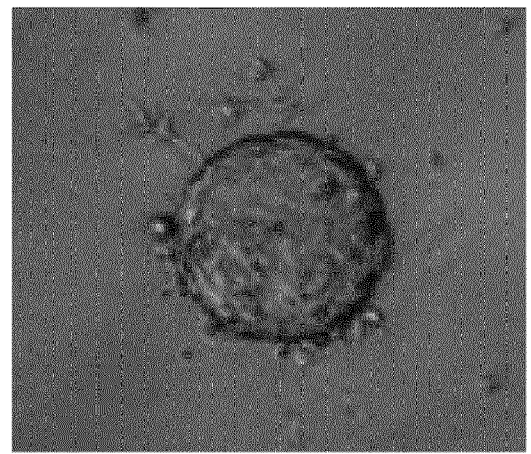
Figure 9I:
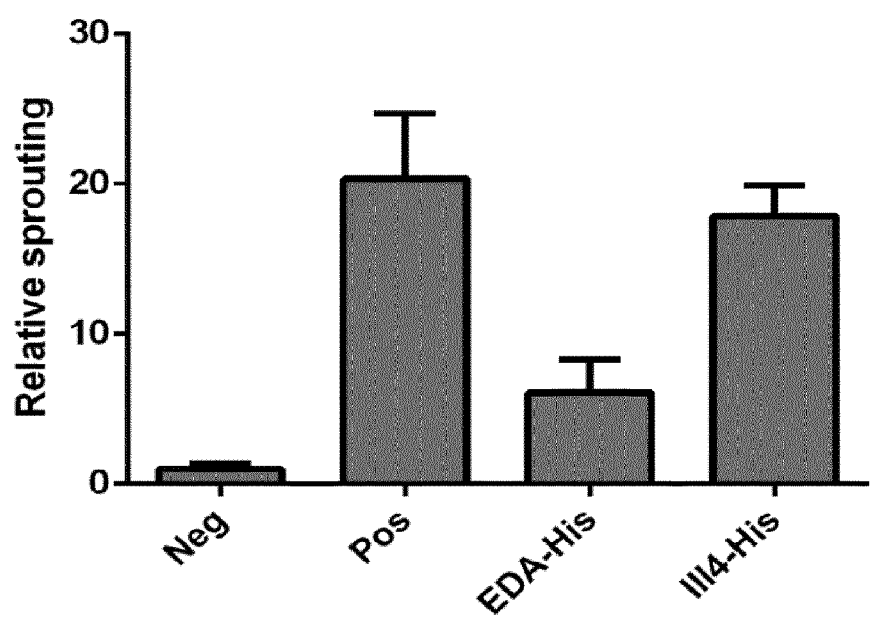

A proper scar formation is of utmost importance to prevent expansive remodeling, thinning of the scar and/or rupture of the infarcted wall after MI. In the present study, There was no difference in collagen content between control and anti-EDA treated animals 28 days after MI (FIGS. 8a and b). In line with this observation, we did not observe any difference in the total amount of myofibroblasts, the main collagen producing cells after MI (data not shown) or mRNA levels of Col1 and Col3 (FIGS. 8c and d).

Anti-EDA Treatment Increases Vessel Formation in the Heart

Upon anti-EDA treatment there were more vessels formed in both the infarct and the border zone (FIG. 9). When we subdivide the vessels in different size classes, we can clearly see that this difference is in the smallest vessels of 5-10 μm in the border zone (FIG. 9d) and in 10-16 μm vessels in the infarct area (FIG. 9f). These classes correspond to capillaries in the myocardium. In vitro 3D sprouting assays show that EDA, and not control fragment 1114, inhibits sprouting of endothelial cells (FIG. 9g to i).

Anti-EDA Treatment Delays Clearance of Acellular Matrix

Figure 10A:
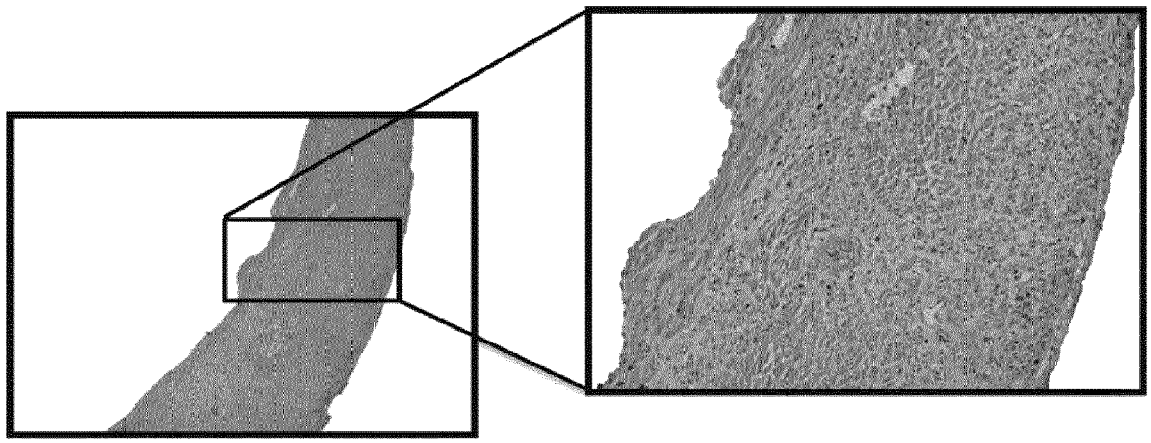
Figure 10B:
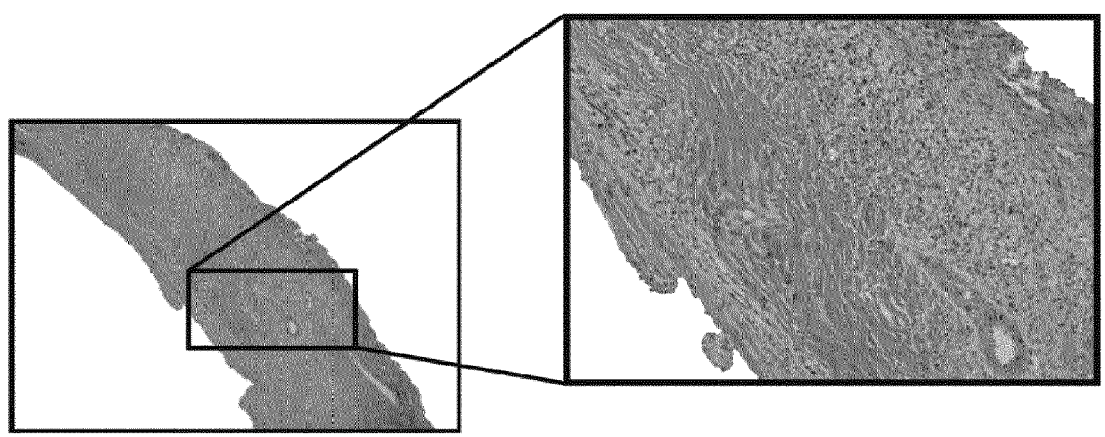
Figure 10C:
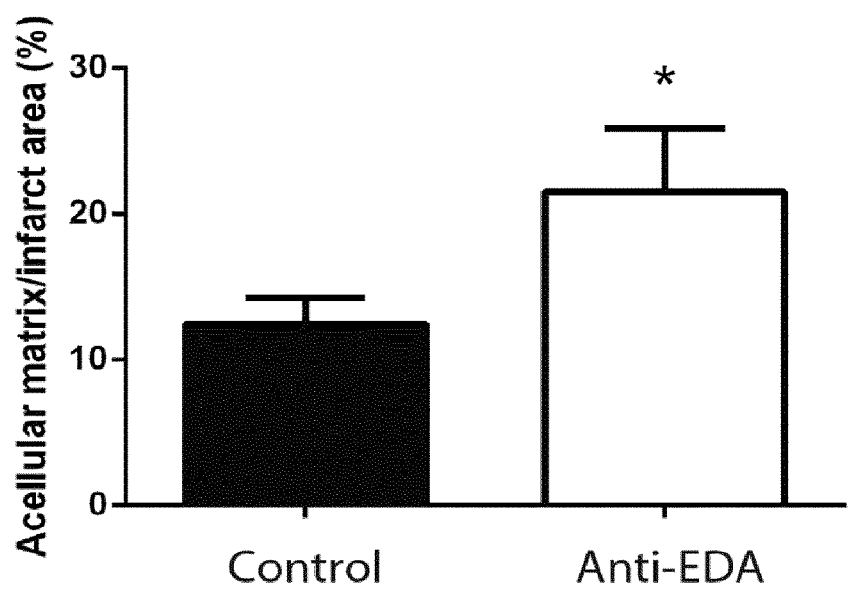
Figure 10D:
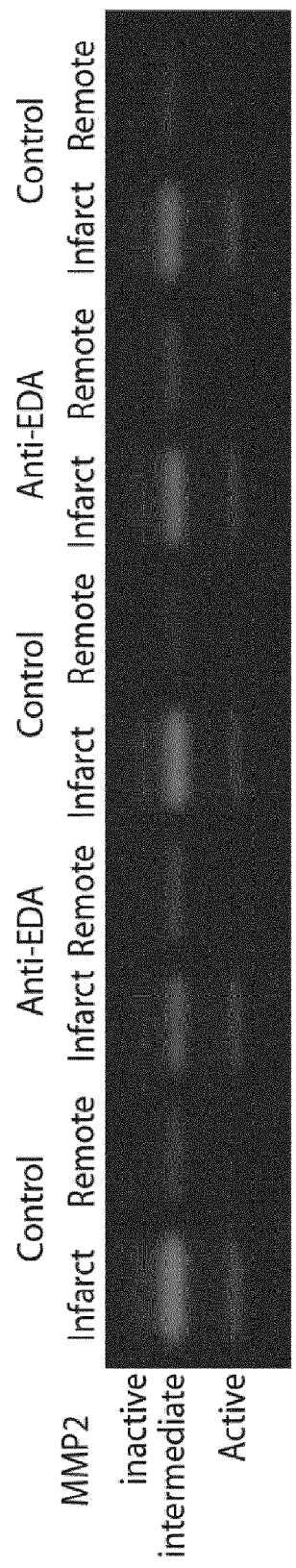
Figure 10E:
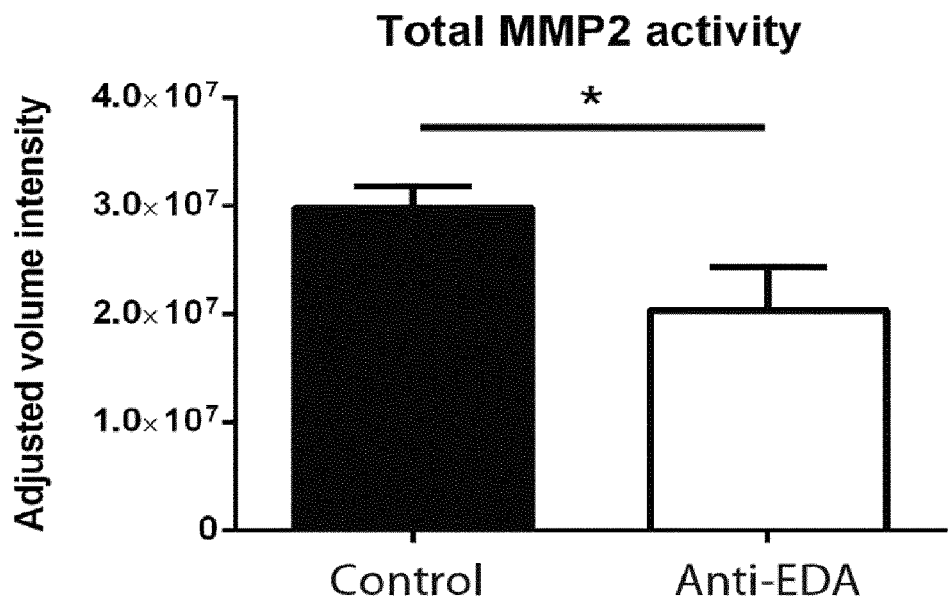
Figure 10F:
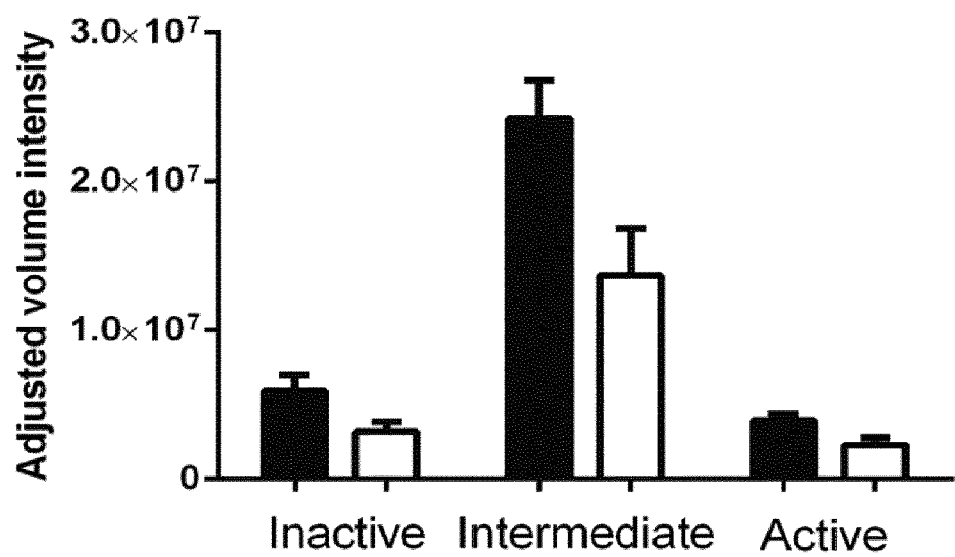
Figure 10G:
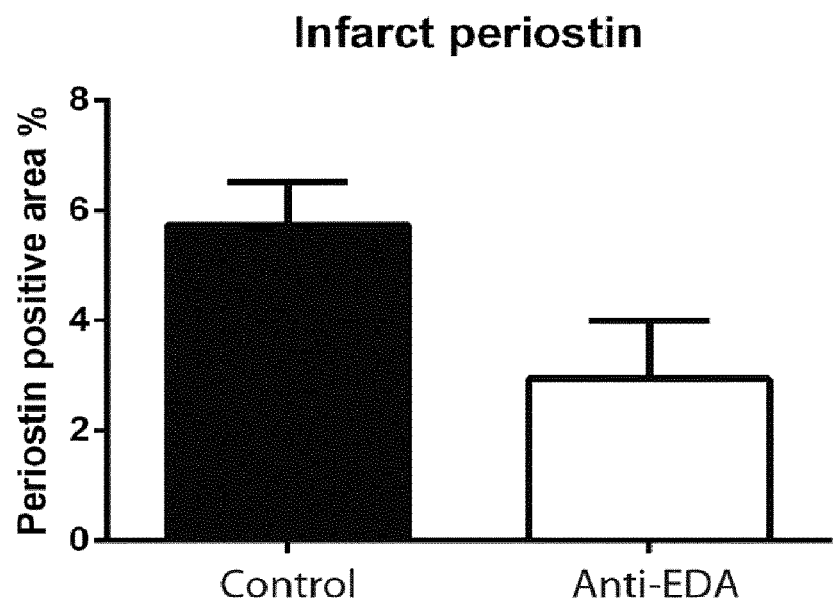
Figure 10H:
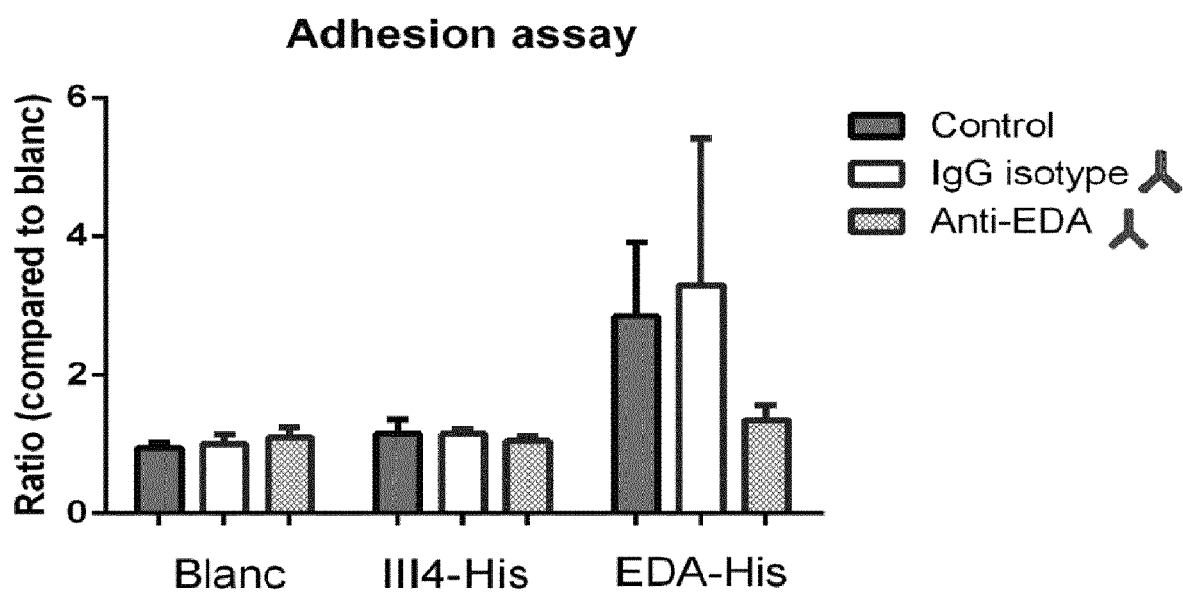

A provisional acellular matrix formation is crucial for hemodynamic compensation for non-viable tissue and scar formation after MI. During wound healing the provisional matrix is slowly degraded and replaced by a firm collagen-based scar. We observed a delayed clearance of acellular matrix in anti-EDA treated mice (FIG. 10a to c). To find an explanation for the delayed clearance of the provisional matrix we studied intrinsic MMP2 and -9 activity in the treatment groups. We found that anti-EDA treatment reduced MMP2 and -9 activity, quantified by zymography (FIG. 10d to f). No change in mRNA levels of MMP2 and -9 was observed between the groups (data not shown). Fibroblasts are the main MMP producing cells in the heart. Periostin staining can estimate the amount of mature fibroblasts in the heart. Upon anti-EDA treatment, periostin expression is reduced (FIG. 10g). Furthermore, in vitro cell adhesion assay show that fibroblast can adhere to EDA and that the anti-EDA antibody can prevent this cell adhesion (FIG. 10h).

EDA is Transiently Expressed in the Infarcted Human Heart

To date, there is no evidence of EDA expression in patients who suffered from an acute MI. We used postmortem human heart specimens to study the timeline of EDA expression in human after MI. EDA was observed in the first 2-3 weeks after an infarction in the infarcted area and in the infarct border zone (FIG. 11). EDA expression was observed in fibroblasts residing in young granulation tissue and in border zone cardiomyocytes. These findings are in line with our previous murine data, in which we show that EDA-FN is indeed temporarily expressed in the ischemic myocardium.

The invention claimed is:

1. A method of treating progression of adverse cardiac remodelling and conditions resulting from or relating to myocardial infarction, which comprises administering to a subject in need thereof, a therapeutically effective amount of an antibody or antigen-binding fragment thereof that binds the EDA domain of fibronectin-EDA, wherein said antibody or antigen-binding fragment thereof comprises
   a heavy chain variable region comprising:
      a CDR1 having the amino acid sequence shown in SEQ ID NO:9;
      a CDR2 having the amino acid sequence shown in SEQ ID NO: 10; and
      a CDR3 having the amino acid sequence shown in SEQ ID NO:11;
   and a light chain variable region comprising:
      a CDR1 having the amino acid sequence shown in SEQ ID NO:12;
      a CDR2 having the amino acid sequence shown in SEQ ID NO: 13; and
      a CDR3 having the amino acid sequence shown in SEQ ID NO:14.

2. A method of treating progression of adverse cardiac remodelling and conditions resulting from or relating to myocardial infarction, which comprises administering to a subject in need thereof, a therapeutically effective amount of an antibody or antigen-binding fragment thereof that binds the EDA domain of fibronectin-EDA, wherein said antibody or antigen-binding fragment thereof comprises a heavy chain variable region comprising:
- a CDR1 having the amino acid sequence shown in SEQ ID NO:3;
- a CDR2 having the amino acid sequence shown in SEQ ID NO:4; and
- a CDR3 having the amino acid sequence shown in SEQ ID NO:5;

and a light chain variable region comprising:
- a CDR1 having the amino acid sequence shown in SEQ ID NO:6;
- a CDR2 having the amino acid sequence shown in SEQ ID NO:7; and
- a CDR3 having the amino acid sequence shown in SEQ ID NO:8.

3. A method of treating progression of adverse cardiac remodelling and conditions resulting from or relating to myocardial infarction, which comprises administering to a subject in need thereof, a therapeutically effective amount of an antibody or antigen-binding fragment thereof that binds the EDA domain of fibronectin-EDA, wherein said antibody or antigen-binding fragment thereof comprises a heavy chain variable region comprising:
- a CDR1 having the amino acid sequence shown in SEQ ID NO:15;
- a CDR2 having the amino acid sequence shown in SEQ ID NO:16; and
- a CDR3 having the amino acid sequence shown in SEQ ID NO:17;

and a light chain variable region comprising:
- a CDR1 having the amino acid sequence shown in SEQ ID NO:18;
- a CDR2 having the amino acid sequence shown in SEQ ID NO:19; and
- a CDR3 having the amino acid sequence shown in SEQ ID NO:20.

4. The method of claim 2, wherein said antibody or antigen-binding fragment thereof comprises a heavy chain and a light chain, wherein said heavy chain has an amino acid sequence as shown in SEQ ID NO:34 and said light chain has an amino acid sequence as shown in SEQ ID NO:35.

5. The method of claim 2, wherein said antibody or antigen-binding fragment thereof is an antibody.

6. The method of claim 2, wherein said antibody or antigen-binding fragment thereof is monoclonal.

7. The method of claim 2, wherein said antibody or antigen-binding fragment thereof is humanized.

8. The method of claim 1, wherein said antibody or antigen-binding fragment thereof is an antibody.

9. The method of claim 1, wherein said antibody or antigen-binding fragment thereof is monoclonal.

10. The method of claim 1, wherein said antibody or antigen-binding fragment thereof is humanized.

11. The method of claim 3, wherein said antibody or antigen-binding fragment thereof is an antibody.

12. The method of claim 3, wherein said antibody or antigen-binding fragment thereof is monoclonal.

13. The method of claim 3, wherein said antibody or antigen-binding fragment thereof is humanized.

* * * * *